US008557516B2

(12) United States Patent
Mahajan et al.

(10) Patent No.: US 8,557,516 B2
(45) Date of Patent: Oct. 15, 2013

(54) AKT TYROSINE 176 PHOSPHORYLATION CANCER BIOMARKER

(75) Inventors: Nupam P. Mahajan, Tampa, FL (US); Kiran N. Mahajan, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 13/205,171

(22) Filed: Aug. 8, 2011

(65) Prior Publication Data

US 2012/0053225 A1    Mar. 1, 2012

Related U.S. Application Data

(63) Continuation of application No. PCT/US2010/023487, filed on Feb. 8, 2010.

(60) Provisional application No. 61/150,551, filed on Feb. 6, 2009.

(51) Int. Cl.
*C12Q 1/68* (2006.01)

(52) U.S. Cl.
USPC .............................. 435/6; 435/325; 435/375

(58) Field of Classification Search
None
See application file for complete search history.

(56) References Cited

U.S. PATENT DOCUMENTS

| 7,358,250 | B2 | 4/2008 | Farthing et al. |
|---|---|---|---|
| 2003/0175763 | A1 | 9/2003 | Degenhardt et al. |
| 2006/0030536 | A1 | 2/2006 | Yu et al. |
| 2006/0046977 | A1 | 3/2006 | Nunes et al. |
| 2007/0072851 | A1 | 3/2007 | Buchanan et al. |
| 2009/0053831 | A1* | 2/2009 | Hornbeck et al. ............ 436/536 |

FOREIGN PATENT DOCUMENTS

| WO | 2005/089443 A2 | 9/2005 |
|---|---|---|
| WO | 2006/122053 A2 | 11/2006 |
| WO | 2010/091354 A3 | 8/2010 |

OTHER PUBLICATIONS

International Search Report for International Patent Application No. PCT/US2010/023487 dated Feb. 8, 2010.
Bellacosa et al. 2005. "Activation of AKT kinases in cancer: implications for therapeutic targeting." Advances in Cancer Research. vol. 94. pp. 29-86.
Burgering et al. 1995. "Protein kinase B (c-Akt) in Phosphatidylinositol-3-OH kinase signal transduction." Nature. vol. 376. pp. 599-602.
Grandis et al. 2004. "Signaling through the epidermal growth factor receptor during the development of malignancy." Pharmacol. Ther. vol. 102. pp. 37-46.
Manser et al. 1993. "A non-receptor tyrosine kinase that inhibits the GTPase activity of p21(cdc42)." Nature. vol. 363. pp. 364-367.
Panigrahi et al. 2004. "The role of PTEN and its signalling pathways, including AKT, in breast cancer; an assessment of relationships with other prognostic factors and with outcome." J. Pathol. vol. 204. pp. 93-100.
Salomon et al. 1995. "Epidermal growth factor-related peptides and their receptors in human malignancies." Crit. Rev. Oncol. Hematol. vol. 19. pp. 183-232.
Alessi et al. 1996. Mechanism of activation of protein kinase B by insulin and IGF-1. Embo J. 15(23): 6541-6551.
Blanco-Aparicio et al. 2007. PTEN, more than the AKT pathway. Carcinogenesis. 28(7): 1379-1386.
Bose et al. 2006. The Akt pathway in human breast cancer: a tissue-array-based analysis. Mod. Pathol. 19: 238-245.
Carpten et al. 2007. A transforming mutation in the pleckstrin homology domain of AKT1 in cancer. Nature. 448: 439-444.
Chen et al. 2001. Regulation of Akt/PKB activation by tyrosine phosphorylation. The Journal of Biological Chemistry 276(34): 31858-31862.
Cheng et al. 2005. The Akt/PKB pathway: molecular target for cancer drug discovery. Oncogene. 24: 7482-7492.
Conus et al. 2002. Direct identification of tyrosine 474 as a regulatory phosphorylation site for the Akt protein kinase. J. Biol. Chem. 277(41): 38021-38028.
Datta et al. 1996. Akt is a direct target of the phosphatidylinositol 3-kinase. Activation by growth factors, v-src and v-Ha-ras, in Sf9 and mammalian cells. The Journal of Biological Chemistry. 271(48): 30835-30839.
Dong et al. 2005. PDK2: the missing piece in the receptor tyrosine kinase signaling pathway puzzle. Am. J. Physiol. Endocrinol. Metab. 289: E187-E196.
Franke et al. 1995. The protein kinase encoded by the Akt proto-oncogene is a target of the PDGF-activated phosphatidylinositol 3-kinase. Cell. 81: 727-736.
Fruman et al. 2000. Hypoglycaemia, liver necrosis and perinatal death in mice lacking all isoforms of phosphoinositide 3-kinase p85 alpha. Nature genetics 26: 379-382.
Galisteo et al. 2006. Activation of the nonreceptor protein tyrosine kinase Ack by multiple extracellular stimuli. Proc. Natl. Acad. Sci. U S A 103(26): 9796-9801.
Gami et al. 2006. Activated AKT/PKB signaling in *C. elegans* uncouples temporally distinct outputs of DAF-2/insulin-like like signaling. BMC Dev. Biol. 6(45): 1-14.
Greer et al. 2005. FOXO transcription factors at the interface between longevity and tumor suppression. Oncogene. 24: 7410-7425.
Hennessy et al. 2005. Exploiting the PI3K/AKT pathway for cancer drug discovery. Nat. Rev. Drug. Discov. 4: 988-1004.

(Continued)

*Primary Examiner* — Kimberly Chong
(74) *Attorney, Agent, or Firm* — Foley & Lardner LLP; Antoinette F. Konski; Alex Y. Nie

(57) ABSTRACT

AKT/PKB kinase is a key signaling component of one of the most frequently activated pathways in cancer and is a major target of cancer drug development. The present study uncovered that growth factors binding to RTKs lead to activation of a non-receptor tyrosine kinase, Ack1 (TNK2), which directly phosphorylates AKT at a conserved tyrosine 176 residue. Tyr176-phosphorylated AKT binds to phosphatidic acid and localizes to the plasma membrane, leading to AKT activation. Expression levels of Tyr176-phosphorylated-AKT and Tyr284-phosphorylated-Ack1 were positively correlated with the severity of disease progression, and inversely correlated with the survival of breast, prostate, lung and pancreatic cancer patients.

14 Claims, 41 Drawing Sheets

(56) References Cited

OTHER PUBLICATIONS

Huang et al. 2007. Dynamic FoxO transcription factors. J. Cell. Sci. 120: 2479-2487.
Hutchinson et al. 2001. Activation of Akt (protein kinase B) in mammary epithelium provides a critical cell survival signal required for tumor progression. Molecular and Cellular Biology 21(6): 2203-2212.
Karathanassis et al. 2002 Binding of the PX domain of p47(phox) to phosphatidylinositol 3,4-bisphosphate and phosphatidic acid is masked by an intramolecular interaction. Embo J. 21(19): 5057-5068.
Kiyono et al. 2000. Stimulation of Ras guanine nucleotide exchange activity of Ras-GRF1/CDC25(Mm) upon tyrosine phosphorylation by the Cdc42-regulated kinase ACK1. J. Biol. Chem. 275(38): 29788-29793.
Li et al. 1999. The tyrosine kinases Syk and Lyn exert opposing effects on the activation of protein kinase Akt/PKB in B lymphocytes. Proceedings of the National Academy of Sciences of the United States of America. 96: 6890-6895.
Mahajan et al. 2003. An SH2 domain-dependent, phosphotyrosine-independent interaction between Vav1 and the Mer receptor tyrosine kinase: a mechanism for localizing guanine nucleotide-exchange factor action. J. Biol. Chem. 278(43): 42596-42603.
Mahajan et al. 2005. Activated tyrosine kinase Ack1 promotes prostate tumorigenesis: role of Ack1 in polyubiquitination of tumor suppressor Wwox. Cancer Res. 65: 10514-10523.
Mahajan et al. 2007. Activated Cdc42-associated kinase Ack1 promotes prostate cancer progression via androgen receptor tyrosine phosphorylation. Proc. Natl. Acad. Sci. U S A. 104(20): 8438-8443.
Majumder et al. 2003. Prostate intraepithelial neoplasia induced by prostate restricted Akt activation: the MPAKT model. Proc. Natl. Acad. Sci. U S A. 100(13): 7841-7846.
Manning et al. 2007. AKT/PKB signaling: navigating downstream. Cell 129: 1261-1274.
Matsumoto et al. 2002. Differential mechanisms of constitutive Akt/PKB activation and its influence on gene expression in pancreatic cancer cells. Jpn. J. Cancer Res. 93: 1317-1326.
Merrick et al. 2006. Analysis of c-ErbB1/epidermal growth factor receptor and c-ErbB2/HER-2 expression in bronchial dysplasia: evaluation of potential targets for chemoprevention of lung cancer. Clin. Cancer Res. 12: 2281-2288.
Modzelewska et al. 2006. Ack1 mediates Cdc42-dependent cell migration and signaling to p130(Cas). J. Biol. Chem. 281(49): 37527-37535.
Paddison et al. 2002. Short hairpin RNAs (shRNAs) induce sequence-specific silencing in mammalian cells. Genes Dev. 16(8):948-958.
Sakurada et al. 1997. Infrequent genetic alterations of the PTEN/MMAC1 gene in Japanese patients with primary cancers of the breast, lung, pancreas, kidney, and ovary. Jpn J. Cancer Res. 88: 1025-1028.
Sarbassov et al. 2005. Phosphorylation and regulation of Akt/PKB by the rictor-mTOR complex. Science. 307: 1098-1101.
Shen et al. 2007. Activated Cdc42-associated kinase 1 is a component of EGF receptor signaling complex and regulates EGF receptor degradation. Mol. Biol. Cell. 18: 732-742.
Stemke-Hale et al. 2008. An integrative genomic and proteomic analysis of PIK3CA, PTEN, and AKT mutations in breast cancer. Cancer Res. 68: 6084-6091.
Stephens et al. 1998. Protein kinase B kinases that mediate phosphatidylinositol 3,4,5-trisphosphate-dependent activation of protein kinase B. Science. 279: 710-714.
Stokoe et al. 1997. Dual role of phosphatidylinositol-3,4,5-trisphosphate in the activation of protein kinase B. Science. 277: 567-570.
Sun et al. 2001. AKT1/PKBalpha kinase is frequently elevated in human cancers and its constitutive activation is required for oncogenic transformation in NIH3T3 cells. Am. J. Pathol. 159(2): 431-437.

Tibes et al. 2008. PI3K/AKT pathway activation in acute myeloid leukaemias is not associated with AKT1 pleckstrin homology domain mutation. Br. J. Haematol. 140: 344-347.
Van Der Horst et al. 2005. Metastatic properties and genomic amplification of the tyrosine kinase gene ACK1. Proc. Natl. Acad. Sci. U S A. 102(44): 15901-15906.
Vasudevan et al. 2009. AKT-independent signaling downstream of oncogenic PIK3CA mutations in human cancer. Cancer Cell. 16: 21-32.
Vivanco et al. 2002. The phosphatidylinositol 3-Kinase AKT pathway in human cancer. Nat. Rev. Cancer. 2: 489-501.
Webster et al. 1998. Requirement for both Shc and phosphatidylinositol 3' kinase signaling pathways in polyomavirus middle T-mediated mammary tumorigenesis. Molecular and cellular biology. 18(4): 2344-2359.
Yokoyama et al. 2003. Biochemical properties of the Cdc42-associated tyrosine kinase ACK1. Substrate specificity, autophosphorylation, and interaction with Hck. J. Biol. Chem. 278(48): 47713-47723.
Zhao et al. 2007. Phospholipase D2-generated phosphatidic acid couples EGFR stimulation to Ras activation by Sos. Nat. Cell. Biol. 9(6): 706-712.
Zhao et al. 2006. The p110alpha isoform of PI3K is essential for proper growth factor signaling and oncogenic transformation. Proc. Natl .Acad. Sci. U S A 103(44): 16296-16300.
Zhou et al. 2004. Activation of the Akt/mammalian target of rapamycin/4E-BP1 pathway by ErbB2 overexpression predicts tumor progression in breast cancers. Clin. Cancer Res. 10: 6779-6788.
Mahajan et al. 2005. Activated tyrosine kinase Ack1 promotes prostate tumorigenesis: role of Ack1 in polyubiquitination of tumor suppressor Wwox. Cancer Res 65: 10514-10523.
Mahajan, K. "Ack1 Tyrosine Kinase Activation Correlates With Pancreatic Cancer Progression", Short Communication, The American Journal of Pathology, vol. 180, No. 4, Apr. 2012, 1386-1393.
Bollag et al., "Clinical efficacy of a RAF inhibitor needs broad target blockade in BRAF-mutant melanoma." Nature 467: 596-599 (2010).
Dimauro et al., "Discovery of 4-amino-5,6-biaryl-furo[2,3-d]pyrimidines as inhibitors of Lck: development of an expedient and divergent synthetic route and preliminary SAR." Bioorganic & medicinal chemistry letters 17(8):2305-2309 (2007).
Elias, "Triple-negative breast cancer: a short review." American journal of clinical oncology 33(6):637-645 (2010).
Hereford et al., "Periodic transcription of yeast histone genes." Cell 30:305-310 (1982).
Hereford etal., "Cell-cycle regulation of yeast histone mRNA." Cell 24:367-375 (1981).
Hirai et al., "Small-molecule inhibition of Wee1 kinase by MK-1775 selectively sensitizes p53-deficient tumor cells to DNA-damaging agents." Mol Cancer Ther 8:2992-3000 (2009).
Khorgami et al., "Stent-and-glue sutureless vascular anastomosis," Medical Hypotheses 77:94-96 (2011).
Mahajan et al., "Ack1 mediated AKT/PKB tyrosine 176 phosphorylation regulates its activation." PLoS One 5(3):e9646 (2010).
Mahajan et al., "Ack1-mediated Androgen Receptor Phosphorylation Modulates Radiation Resistance in Castration-resistant Prostate Cancer." The Journal of biological chemistry 287(26):22112-22122 (2012).
Mahajan et al., "Effect of Ack1 tyrosine kinase inhibitor on ligand-independent androgen receptor activity." Prostate 70(12):1274-1285 (2010).
Mahajan et al., "PI3K-independent AKT activation in cancers: A treasure trove for novel therapeutics." J Cell Physiol 227:3178-3184 (2012).
Mahajan et al., "Shepherding AKT and androgen receptor by Ack1 tyrosine kinase." J Cell Physiol 224(2):327-333 (2010).
Manning et al., "The protein kinase complement of the human genome." Science 298(5600):1912-1934 (2002).
Marzluff et al., "Metabolism and regulation of canonical histone mRNAs: life without a poly(A) tail." Nature reviews 9:843-854 (2008).
McGowan et al., "Cell cycle regulation of human WEE1." The EMBO journal 14:2166-2175 (1995).

(56) References Cited

OTHER PUBLICATIONS

Mollapour et al., "Swe1Wee1-dependent tyrosine phosphorylation of Hsp90 regulates distinct facets of chaperone function." Mol Cell 37:333-343 (2010).

Morris et al., "Differences in breast carcinoma characteristics in newly diagnosed African-American and Caucasian patients: a single-institution compilation compared with the National Cancer Institute's Surveillance, Epidemiology, and End Results database." Cancer 110(4):876-884 (2007).

Nakanishi et al., "A comprehensive library of histone mutants identifies nucleosomal residues required for H3K4 methylation." Nature structural & molecular biology 15:881-888 (2008).

Osley et al., "Identification of a sequence responsible for periodic synthesis of yeast histone 2A mRNA." Proceedings of the National Academy of Sciences of the United States of America 79:7689-7693 (1982).

Osley et al., "Yeast Histone Genes Show Dosage Compensation," Cell 24:377-384 (1981).

Osley, "The regulation of histone synthesis in the cell cycle." Annual review of biochemistry 60:827-861 (1991).

Wei et al., "The cyclin E/Cdk2 substrate and Cajal body component p220(NPAT) activates histone transcription through a novel LisH-like domain." Molecular and cellular biology 23:3669-3680 (2003).

Zhao et al., "NPAT links cyclin E-Cdk2 to the regulation of replication-dependent histone gene transcription." Genes & development 14:2283-2297 (2000).

Lee, M.W. et al. (2008) "Akt1 inhibition by Rna interference sensitizes human non-small cell lung cancer cells to cisplatin," International Journal of Cancer 122(10):2380-2384.

Hoffman, R.L. et al. (1999) "Use of a Novel Expression System to Generate Antibodies (ab) to Specific Akt Isoforms," Society for Neuroscience 25:abstract.

Kim, D. et al. (2005) "Akt/Pkb signaling mechanisms in cancer and chemoresistance," Frontiers in Bioscience 10(1):975-987.

Pedersen, H. C. et al. (2008) "Monoclonal antibodies specific for Phospho-4E-BP1 (Thr 70) and phosphor-AFT (Ser 473) indicate prognosis in breast cancer," European Journal of Cancer, Supplement 6(7):60.

Chan, T.O. et al. (1999) "AKT/PKB and Other D3 Phosphoinositide-Regulated Kinases: Kinase Activation by Phosphoinositide-Dependent Phosphorylation," Annual Review of Biochemistry 68:965-1014.

Han, Z. et al. (2006) "Reversal of multidrug resistance of gastric cancer cells by downregulation of Akt1 with Akt1 siRNA," Journal of Experimental and Clinical Cancer Research 25(4):601-606.

Supplementary European Search Report for European Patent Application No. EP 10739230.0, mailed Jun. 17, 2013, 5 pages.

\* cited by examiner

| | | | |
|---|---|---|---|
| Seq Id. No. 1 | Homo sapiens | 167 VKEKATGRY AKILKKEVIVAKD 190 | |
| Seq Id. No. 2 | Bos taurus | 167 VKEKATGRY AKILKKEVIVAKD 190 | |
| Seq Id. No. 3 | Canis familiaris | 167 VKEKATGRY AKILKKEVIVAKD 190 | |
| Seq Id. No. 4 | Mus musculus | 167 VKEKATGRY AKILKKEVIVAKD 190 | |
| Seq Id. No. 5 | Rattus norvegicus | 167 VKEKATGRY AKILKKEVIVAKD 190 | |
| Seq Id. No. 6 | Xenopus laevis | 168 VKEKATGRY AKILKKEVIVAKD 191 | |
| Seq Id. No. 7 | Danio rerio | 163 VKEKATGRY AKILKKEVIVAKD 186 | |
| Seq Id. No. 8 | Aedes aegypti | 201 CREKTTAKL AIKILKKEVIVQKD 224 | |
| Seq Id. No. 9 | D. melanogaster | 202 CREKATAKL AIKILKKEVIIQKD 225 | |
| Seq Id. No. 10 | Bombyx mori | 165 SREKGTGKL AKILKKHLIIQKD 188 | |
| Seq Id. No. 11 | Caenorhabditis elegans | 210 CKEKRTGKL AIKILKKDVIIARE 233 | |
| Seq Id. No. 12 | S. cerevisiae | 429 VKKDTGRI AKVLSKKVIVKKN 452 | |
| Seq Id. No. 13 | H. sapiens AKT1 | 167 VKEKATGRY AKILKKEVIVAKD 190 | |
| Seq Id. No. 14 | H. sapiens AKT2 | 169 VREKATGRY AKILKKEVIIAKD 192 | |
| Seq Id. No. 15 | H. sapiens AKT3 | 165 VREKASGKY AKILKKEVIIAKD 188 | |

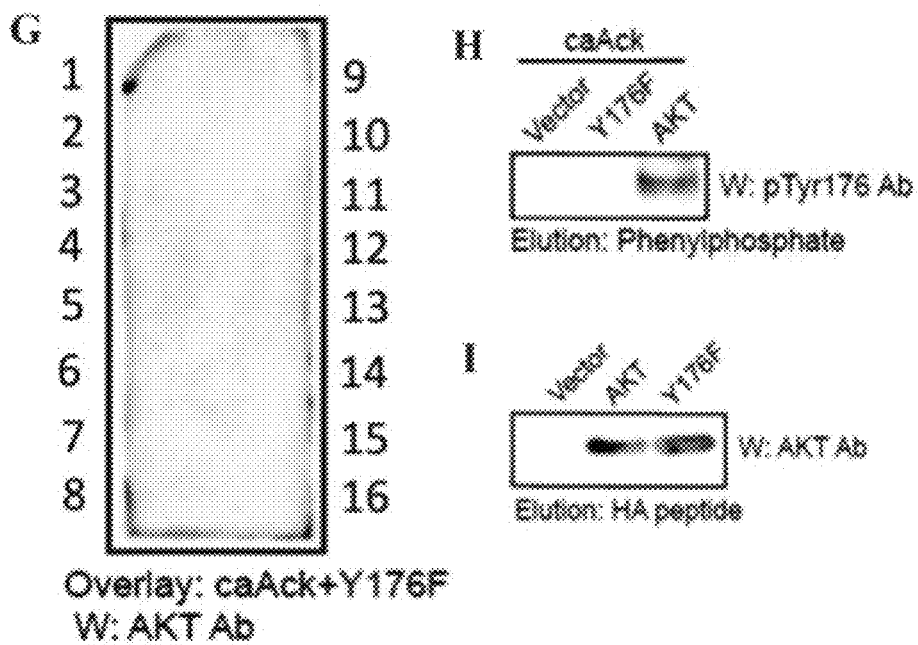
Figure 39 (G-I)
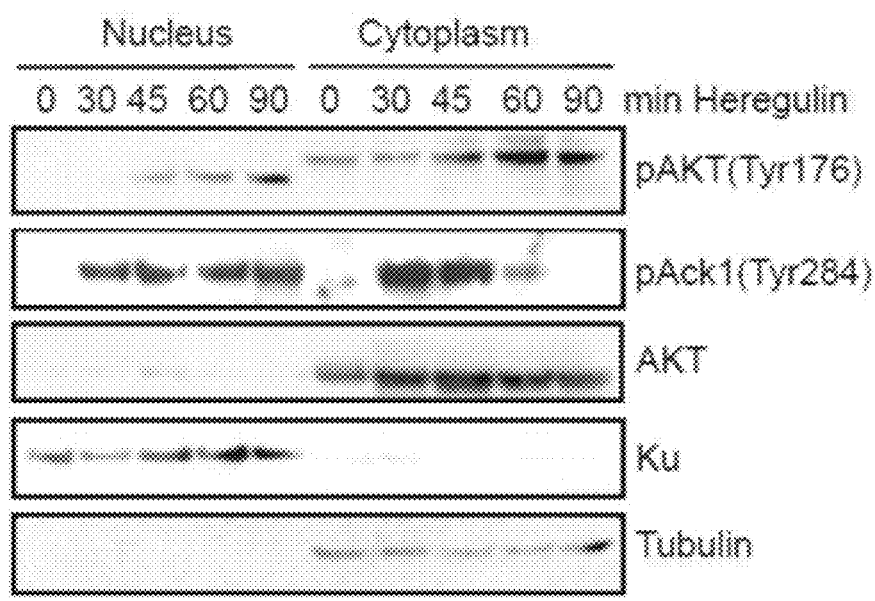
Figure 40

AKT TYROSINE 176 PHOSPHORYLATION CANCER BIOMARKER

CROSS REFERENCE TO RELATED APPLICATIONS

This application is a continuation of prior filed International Application, Serial Number PCT/US2010/023487 filed Feb. 8, 2010, which claims priority to U.S. Provisional Patent Application No. 61/150,551, entitled, "AKT Tyrosine 176 Phosphorylation Cancer Biomarker", filed Feb. 6, 2009, the contents of each of which are herein incorporated by reference.

FIELD OF INVENTION

This invention relates to methods and compositions for the diagnosis, classification, and treatment of cancer. More specifically, this invention is a method of identifying cancer using novel protein phosphorylation status.

BACKGROUND OF THE INVENTION

The intracellular tyrosine kinase, Ack1 is a ~141 kDa protein with amino terminal sterile alpha motif (SAM) domain, kinase domain, Src homology 3 (SH3) domain, Cdc42/Rac interactive-binding (CRIB) domain, proline rich domain and UBA domain at the carboxy terminus (FIG. 22) (Manser, E., Leung, T., Salihuddin, H., Tan, L. & Lim, L. A non-receptor tyrosine kinase that inhibits the GTPase activity of p21cdc42. Nature 363, 364-367 (1993); Galisteo, M. L., Yang, Y., Urena, J. & Schlessinger, J. Activation of the nonreceptor protein tyrosine kinase Ack occurs by multiple extracellular stimuli. Proc Natl Acad Sci USA 103, 9796-9801 (2006)). AKT plays a central role in growth, proliferation and cell survival (Manning B D, Cantley L C (2007) AKT/PKB signaling: navigating downstream. Cell 129: 1261-1274; Bellacosa A, et al. (2005) Activation of AKT kinases in cancer: implications for therapeutic targeting. Adv Cancer Res 94: 29-86; Vivanco I, Sawyers C L (2002) The phosphatidylinositol 3-Kinase AKT pathway in human cancer. Nat Rev Cancer 2: 489-501). AKT activation occurs when ligand binding to RTK facilitates translocation of AKT to the plasma membrane (Franke T F, et al. (1995). The protein kinase encoded by the Akt proto-oncogene is a target of the PDGF-activated phosphatidylinositol 3-kinase. Cell 81: 727-736; Burgering B M, Coffer P J (1995) Protein kinase B (c-Akt) in phosphatidylinositol-3-OH kinase signal transduction. Nature 376: 599-602; Stephens L, et al. (1998) Protein kinase B kinases that mediate phosphatidylinositol 3,4,5-trisphosphate-dependent activation of protein kinase B. Science 279: 710-714; Stokoe D, et al. (1997) Dual role of phosphatidylinositol-3,4,5-trisphosphate in the activation of protein kinase B. Science 277: 567-570) where it is phosphorylated at Thr308 by phosphoinositide-dependent protein kinase-1 (PDK1) and at Ser473 by the 'PDK2', a class of about 10 different kinases (Dong L Q, Liu F (2005) PDK2: the missing piece in the receptor tyrosine kinase signaling pathway puzzle. Am J Physiol Endocrinol Metab 289: E187-196) including the mTORC2 complex (Sarbassov D D, et al (2005) Phosphorylation and regulation of Akt/PKB by the rictor-mTOR complex. Science 307: 1098-1101). Although RTKs do not directly phosphorylate Ack1, they facilitate Ack1 autophosphorylation in a ligand dependent manner (Mahajan, N. P., Whang, Y. E., Mohler, J. L. & Earp, H. S. Activated tyrosine kinase Ack1 promotes prostate tumorigenesis: role of Ack1 in polyubiquitination of tumor suppressor Wwox. Cancer Res 65, 10514-10523 (2005)). Phosphorylation of AKT at Thr308 and Ser473 leads to its kinase activation (Alessi D R, et al. (1996) Mechanism of activation of protein kinase B by insulin and IGF-1. Embo J 15: 6541-6551). Upon activation, AKT phosphorylates its substrates to transduce survival signals (Manning B D, Cantley L C (2007) AKT/PKB signaling: navigating downstream. Cell 129: 1261-1274; Vivanco I, Sawyers C L (2002) The phosphatidylinositol 3-Kinase AKT pathway in human cancer. Nat Rev Cancer 2: 489-501; Greer E L, Brunet A (2005) FOXO transcription factors at the interface between longevity and tumor suppression. Oncogene 24: 7410-7425; Huang H, Tindall D J (2007) Dynamic FoxO transcription factors. J Cell Sci 120: 2479-2487).

Activation of protein kinase AKT/PKB is common occurrence in variety of human cancers (Manning, B. D. & Cantley, L. C. AKT/PKB signaling: navigating downstream. Cell 129, 1261-1274 (2007); Bellacosa, A., Kumar, C. C., Di Cristofano, A. & Testa, J. R. Activation of AKT kinases in cancer: implications for therapeutic targeting. Advances in cancer research 94, 29-86 (2005)). During AKT activation, the first step is the production of phosphatidylinositol 3,4,5 trisphosphate (PIP3) by PI3K. PDK1 and AKT bind the phospholipid PIP3 via their PH domains and are recruited to the plasma membrane. While RTK/PI3K mediated recruitment of AKT to the plasma membrane is a well characterized mechanism, mounting evidence indicate that AKT activation can occur in a PI3K-independent fashion (Carpten J D, et al. (2007) A transforming mutation in the pleckstrin homology domain of AKT1 in cancer. Nature 448: 439-444; Zhao J J, et al. (2006) The p110alpha isoform of PI3K is essential for proper growth factor signaling and oncogenic transformation. Proc Natl Acad Sci USA 103: 16296-16300; Sun M, et al. (2001) AKT1/PKBalpha kinase is frequently elevated in human cancers and its constitutive activation is required for oncogenic transformation in NIH3T3 cells. Am J Pathol 159: 431-437; Stemke-Hale K, et al. (2008) An integrative genomic and proteomic analysis of PIK3CA, PTEN, and AKT mutations in breast cancer. Cancer Res 68: 6084-6091; Hennessy B T, et al. (2005) Exploiting the PI3K/AKT pathway for cancer drug discovery. Nat Rev Drug Discov 4: 988-1004; Gami M S, et al. (2006) Activated AKT/PKB signaling in C. elegans uncouples temporally distinct outputs of DAF-2/insulin-like signaling. BMC Dev Biol 6: 45). About a third of the breast and prostate tumors and majority of the pancreatic tumors that exhibit AKT activation, retain normal PTEN and PI3K activity (Sun M, et al. (2001) AKT1/PKBalpha kinase is frequently elevated in human cancers and its constitutive activation is required for oncogenic transformation in NIH3T3 cells. Am J Pathol 159: 431-437; Bose S, et al. (2006) The Akt pathway in human breast cancer: a tissue-array-based analysis. Mod Pathol 19: 238-245; Panigrahi A R, et al. (2004) The role of PTEN and its signalling pathways, including AKT, in breast cancer; an assessment of relationships with other prognostic factors and with outcome. J Pathol 204: 93-100). Interestingly, normal PTEN expression was also seen in breast, ovarian and prostate tumors that exhibit activated AKT (Sun M, et al. (2001) AKT1/PKBalpha kinase is frequently elevated in human cancers and its constitutive activation is required for oncogenic transformation in NIH3T3 cells. Am J Pathol 159: 431-437). While RTKs are suggested to be involved (Zhou X, et al. (2004) Activation of the Akt/mammalian target of rapamycin/4E-BP1 pathway by ErbB2 overexpression predicts tumor progression in breast cancers. Clin Cancer Res 10: 6779-6788), the molecular mechanisms regulating RTK mediated AKT activation in cancers with normal PTEN and PI3K activity is poorly understood (Tibes R, et al. (2008) PI3K/AKT pathway activation in acute myeloid leukaemias is not associated with AKT1 pleckstrin homology domain mutation. Br J Haematol 140: 344-347). Further, PIK3CA activating mutation has recently been shown to be neither necessary nor sufficient for full AKT activation in situ (Vasudevan K M, et al. (2009) AKT-independent signaling downstream of oncogenic PIK3CA mutations in human cancer. Cancer Cell 16: 21-32). Thus, collectively these data suggest the existence of additional pathways that regulate AKT activation in response to growth factors.

Accordingly, there remains an unmet need for additional biomarkers predictive of precancerous or cancerous lesions, particularly for precancerous and cancerous lesions not utilizing PI3K/PTEN-dependent activation of AKT. Additionally, there remains an important need for additional treatment regimens and therapeutics to overcome the unresponsiveness of such precancerous and cancerous lesions. The present invention further meets these important needs, and others, as will become apparent in the teachings that follow.

SUMMARY OF INVENTION

Ack1, a nonreceptor tyrosine kinase has emerged as a critical early transducer of variety of extracellular growth factor stimuli including heregulin, insulin, EGF and PDGF signaling (Manser E, et al. (1993) A non-receptor tyrosine kinase that inhibits the GTPase activity of p21cdc42. Nature 363: 364-367; Mahajan N P, et al. (2005) Activated tyrosine kinase Ack1 promotes prostate tumorigenesis: role of Ack1 in polyubiquitination of tumor suppressor Wwox. Cancer Res 65: 10514-10523; Mahajan N P, et al. (2007) Activated Cdc42-associated kinase Ack1 promotes prostate cancer progression via androgen receptor tyrosine phosphorylation. Proc Natl Acad Sci USA 104: 8438-8443; Yokoyama N, Miller W T (2003) Biochemical properties of the Cdc42-associated tyrosine kinase ACK1. Substrate specificity, autophosphorylation, and interaction with Hck. J Biol Chem 278: 47713-47723; Galisteo M L, et al. (2006) Activation of the nonreceptor protein tyrosine kinase Ack by multiple extracellular stimuli. Proc Natl Acad Sci USA 103: 9796-9801). Ack1 is ubiquitously expressed and primarily phosphorylated at Tyr284 leading to its kinase activation (Mahajan N P, et al. (2005) Activated tyrosine kinase Ack1 promotes prostate tumorigenesis: role of Ack1 in polyubiquitination of tumor suppressor Wwox. Cancer Res 65: 10514-10523; Yokoyama N, Miller W T (2003) Biochemical properties of the Cdc42-associated tyrosine kinase ACK1. Substrate specificity, autophosphorylation, and interaction with Hck. J Biol Chem 278: 47713-47723). Earlier studies demonstrated that Ack1 regulates prostate cancer progression to androgen independence by positively regulating androgen receptor (AR) and negatively regulating the tumor suppressor, Wwox (Mahajan N P, et al. (2005) Activated tyrosine kinase Ack1 promotes prostate tumorigenesis: role of Ack1 in polyubiquitination of tumor suppressor Wwox. Cancer Res 65: 10514-10523; Mahajan N P, et al. (2007) Activated Cdc42-associated kinase Ack1 promotes prostate cancer progression via androgen receptor tyrosine phosphorylation. Proc Natl Acad Sci USA 104: 8438-8443). Ack1 gene is also shown to be amplified in primary lung, ovarian and prostate tumors which correlated with poor prognosis (van der Horst E H, et al. (2005) Metastatic properties and genomic amplification of the tyrosine kinase gene ACK1. Proc Natl Acad Sci USA 102: 15901-15906).

Mice expressing activated Ack1 specifically in the prostate exhibited AKT Tyr176-phosphorylation and developed prostatic intraepithelial neoplasia (PINs), which progressed to prostatic adenocarcinoma. Further, Tyr284-phosphorylated-Ack1 and Tyr176-phosphorylated-AKT levels were significantly upregulated in human breast and pancreatic cancers (n=880), which correlated with severity of disease progression but exhibited inverse correlation to patient survival. These studies demonstrate that at least one previously unknown phosphorylation event in AKT is a prerequisite for its compartmentalization and activation, and is a signature of advanced stage breast and pancreatic cancers. The data indicates that RTK/Ack1 mediated AKT activation pathway represent a new paradigm in those cancers caused primarily due to the aberrant activation of receptor/non-receptor tyrosine kinases with the normal PI3K and PTEN activity, and represents a new target for drug discovery.

Significant upregulation in AKT Tyr176-phosphorylation in mPINs of Prob-Ack1 transgenic mice and human breast and pancreatic cancers provides mechanistic insight into AKT Tyr176-phosphorylation and its role in tumor initiation and progression. Indeed, the role of Tyr176-phosphorylation may not be limited to breast or pancreatic cancers. Other tumors that display ErbB-2 and EGFR overexpression or amplifications, e.g. lung, colon, ovarian and prostate cancer samples also exhibited Tyr284-phosphorylated-Ack1 and Tyr176-phosphorylated-AKT which correlated with progression of disease (KM, NPM, unpublished data).

Large numbers of tumors are reliant upon AKT activation for survival and growth making it an attractive target for molecular therapeutics. This prompted development of AKT inhibitors, e.g. ATP-competitive inhibitors, pseudosubstrate inhibitors, allosteric AKT kinase inhibitors, PtdIns(3,4,5)P$_3$ analogs and API-2/triciribine (Cheng, J. Q., Lindsley, C. W., Cheng, G. Z., Yang, H. & Nicosia, S. V. The Akt/PKB pathway: molecular target for cancer drug discovery. *Oncogene* 24, 7482-7492 (2005)). The assay that was used to assess AKT activity during development of these AKT inhibitors was primarily based on AKT Ser473-phosphorylation. The data indicates that a new class of AKT-inhibitors can be identified using assays based on AKT Tyr176-phosphorylation. These novel AKT inhibitors could have implication in those cancers that display aberrant activation of receptor or non receptor tyrosine kinases.

Methods for detecting and/or diagnosing cancer or precancerous growths and lesions are disclosed. Exemplary cancers include breast, prostate, and pancreatic cancers. The diagnostic may, for example, comprise a biological test from a sample or region of tissue that is suspected to be cancerous or precancerous. The level of AKT Tyr176-phosphorylation is detected in the sample. Samples of biological controls, such as tissue samples from non-cancerous tissue may be used as a control. In such instances, the control may include a demographic sampling of a population. Alternatively, the sample is collected and the phosphorylated variant of a protein of interest is compared to the total protein for that specific protein of interest. For example, the present invention may be used to compare the level of Tyrosine 176-phosphorylated AKT or pTyr176-AKT to the total level of AKT in a cell. The level of protein expression is then useful in determining whether the sample has cancer. The higher expression of a phosphorylated protein of interest relative to a control may be indicative of cancer, and may also indicate the stage of the cancer.

A sample of tissue suspect to be cancer is collected and expression levels determined for pTyr284-Ack1. The protein expression levels are then compared to expression levels of a control, providing information on the presence of a precancerous or cancerous lesion based on the differential protein expression levels. The protein expression may be elevated in some samples, indicating the presence of a cancer or precancerous growth in the subject, or the stage of the cancer. Alternatively, a database of protein levels from normal tissue samples may be used as a control, and in specific variations the database contains expression levels obtained from a demographically diverse population.

The AKT Tyr176-phosphorylation may, in a different variation of the invention, be determined by examining the expression spatially throughout a sample cell, such as examining the expression patterns of phosphorylated proteins of interest in the cell membrane and nucleus.

The present invention describes determining the efficacy of a therapeutic treatment regimen. The expression levels of at least pTyr176-AKT and/or pTyr284-Ack1 is measured, followed by administration of a therapeutic treatment. The expression levels of the phosphorylated protein(s) are then measured after administration of the therapeutic regimen, allowing a comparison of the expression levels of the phosphorylated protein(s) in the first collection and the second collection. A decrease in the expression levels in the second collection relative to the first collection is indicative that the therapeutic regimen is effective in the subject. In specific variations, the invention utilizes antibodies, such as monoclonal, polyclonal, fragments of antibodies and engineered antibodies, which specifically bind to pTyr176-AKT. In some embodiments, the antibodies specifically bind of Ack1 or AKT that is phosphorylated at a specific site, such as pTyr284-Ack1 or pTyr176-AKT. Of note, the suspect tissue may be collected from breast tissue, prostate tissue, pancreatic tissue, lung tissue, brain tissue, ovarian tissue and blood. The therapeutic regimen may target phosphorylated pTyr176-AKT.

A method of treating cancer is also disclosed. A sample of cancer cell population is contacted with at least one amino acid modification, designed to specifically bind to an activated AKT or pTyr176-AKT. According to one aspect of the present invention, the use of pTyr176-AKT in the development of molecule inhibitors, such as small interfering RNA (siRNA), antisense nucleic acids, and immunodiagnostic or immunotherapies are disclosed. These molecules are useful in decreasing the expression of pTyr176-AKT by affecting transcription, translation or post-translational modification. The invention also provides antagonists of pTyr176-AKT, including small molecules, like siRNA, antibodies, antibody fragments, and compounds that bind and interfere with pTyr176-AKT formation and function. These methods have been found especially useful against pancreatic cancers, prostate cancers, lung cancers, brain cancers, blood cancers, ovarian cancers and breast cancers.

The invention further includes molecules that can decrease the expression of pTyr176-AKT. Exemplary of compounds useful in the present invention are compounds that are specific for Ack1 and/or AKT, such as those described by Farthing, et al. (U.S. Pat. No. 7,358,25); Nunes, et al. (U.S. application Ser. No. 11/184,237); and Buchanan, et al. (U.S. application Ser. No. 11/506,381).

BRIEF DESCRIPTION OF THE DRAWINGS

For a fuller understanding of the invention, reference should be made to the following detailed description, taken in connection with the accompanying drawings, in which:

FIG. 11 is a table showing the alignment of AKT protein sequences which revealed that tyrosine at 176 is invariant from yeast to humans and all the three known human AKT isoforms. AKT protein sequences are shown for Homo sapiens (SEQ ID NO:1); Bos Taurus (SEQ ID NO:2); Canis familiaris (SEQ ID NO:3); Mus musculus (SEQ ID NO:4); Rattus norvegicus (SEQ ID NO:5); Xenopus laevis (SEQ ID NO:6); Danio rerio (SEQ ID NO:7); Aedes aegypti (SEQ ID NO:8); D. melanogaster (SEQ ID NO:9); Bombyx mori (SEQ ID NO:10); Caenorhabititis elegans (SEQ ID NO:11); S. cerevisiae (SEQ ID NO:12); H. sapiens AKT1 (SEQ ID NO:13); H. sapiens AKT2 (SEQ ID NO:14); and H. sapiens AKT3 (SEQ ID NO:15).

E346K mutant Ack1 interacts with and Tyr-phosphorylates AKT. 293T cells were co-transfected with HA-tagged Ack1 point mutants. Equal amounts of protein lysates were subjected to IP using HA antibodies. IB with AKT antibodies revealed formation of activated Ack1 (E346K)/endogenous AKT complex (top panel).

Figure 24:
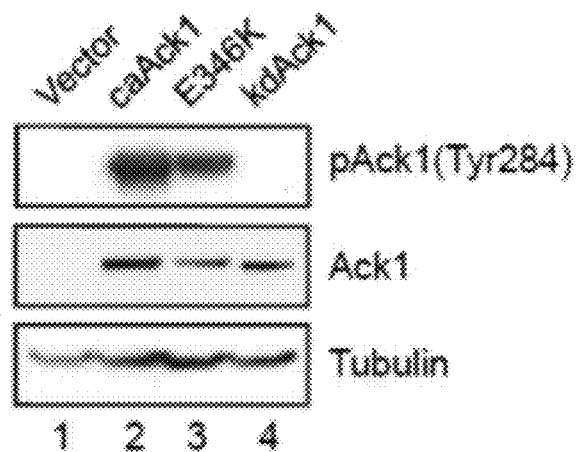

FIG. 24 is a blot showing the somatic autoactivation of Ack1. HEK293T cells were transfected with HA-tagged E346K, caAck or kdAck (K158R) mutants. Lysates were subjected to IP using anti-HA (top panel) antibodies followed by IB with pTyr284-Ack1 antibodies. Lower panels show IB with indicated antibodies.

FIGS. 25(A) and (B) are a composite showing the somatic autoactivation of Ack1. (A) E346K or caAck mediated AKT Tyr-phosphorylation leads to AKT kinase activation. HEK293T cells were co-transfected with E346K or myc-tagged caAck and AKT or Y176F mutant. Lysates were subjected to IP using anti-myc (top panel) and anti-Ack1 (second panel) antibodies followed by IB with pTyr antibodies. The same lysates were processed for kinase assay shown in S6F. (B) Ack1 autoactivation leads to AKT kinase activation. As described in S6E, lysates were IP with HA-antibodies, followed by AKT kinase assay. Low levels of Ack1 kinase activity in vector transfected cells was treated as zero and increased kinase activity (in percentage) over the vector expressing cells is shown.

Figure 26:
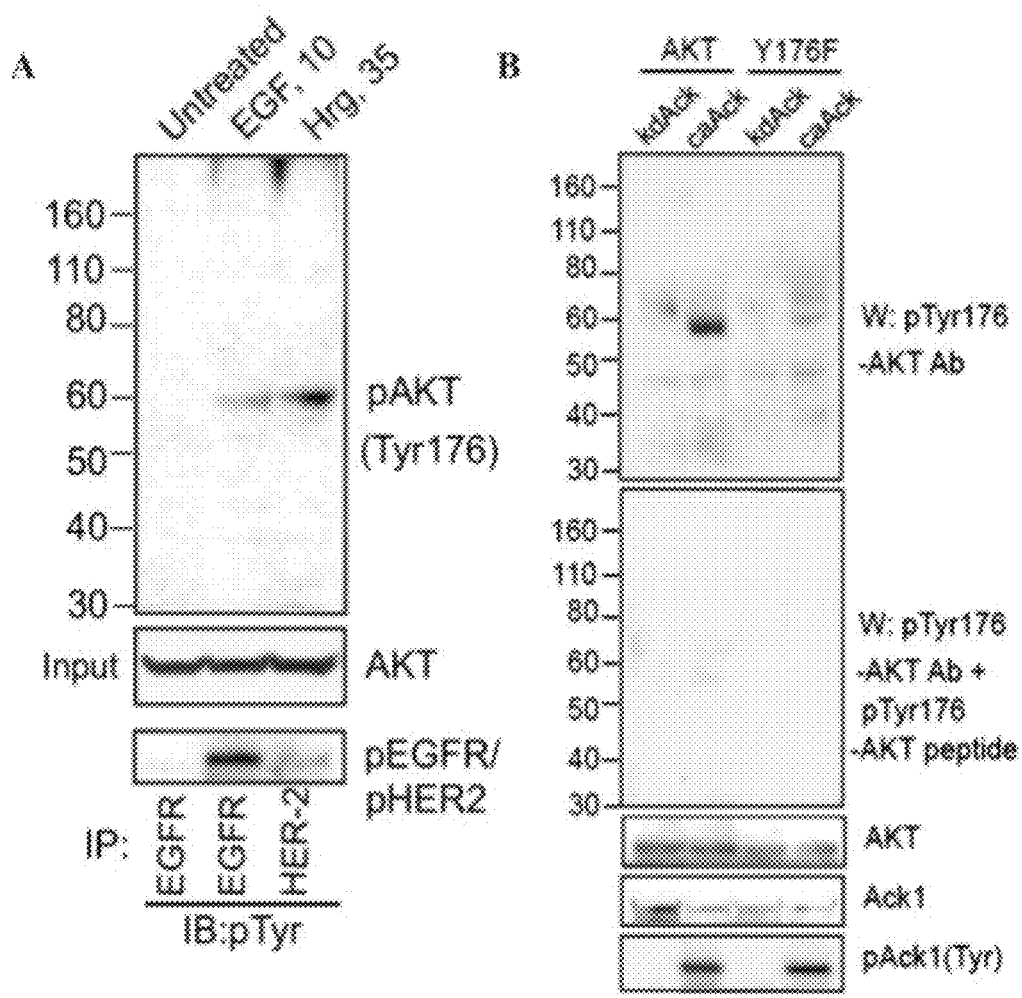

FIGS. 26(A) and (B) are blots showing characterization of antibodies that specifically recognize Tyr176-phosphorylated AKT. (A) RWPE, normal prostate epithelial cells were treated with EGF (10 ng/ml, 10 mins) and heregulin (10 ng/ml, 35 mins), whole cell protein lysates were subjected to IB with indicated antibodies. (B) 293T cells were co-transfected with myc-tagged caAck or kdAck and AKT or Y176F mutant. Equal amounts of whole protein lysates were subjected to immunoblotting with pTyr176-AKT antibodies (top panel). The pTyr176-antibodies recognize only the pTyrAKT (lane 2), but not the Y176F point mutant (lane 4). Similarly, equal amounts of whole protein lysates were subjected to immunoblotting with pTyr176-AKT antibodies that were preincubated with AKT phosphopeptide for 30 min (second panel). The pTyr176-antibodies blocked by AKT phosphopeptide failed to recognize pTyr176-AKT (lane 2).

Figure 27:
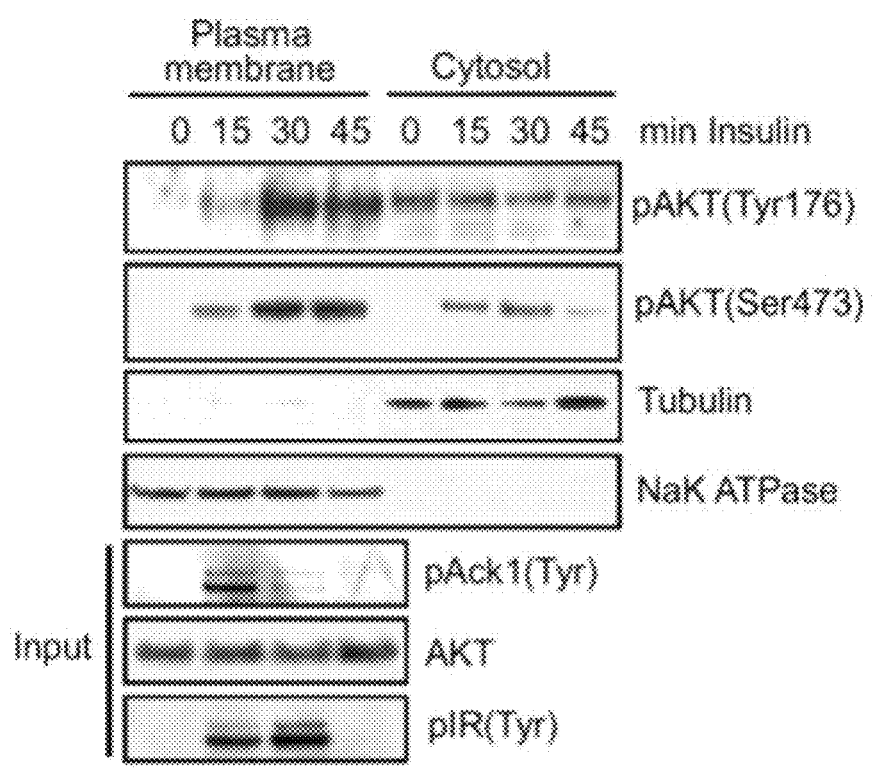

FIG. 27 is a blot showing Tyr176-phosphorylation regulates AKT plasma membrane localization. MCF-7 cells were serum starved (24 h) and treated with insulin (50 ng/ml) or for indicated times. Cell lysates were fractionated and IB with the indicated antibodies. Input panels pAck1 (Tyr), pIR(Tyr) and pHER-2(Tyr) represents IP with respective antibodies followed by IB with pTyr antibodies.

Figure 28:
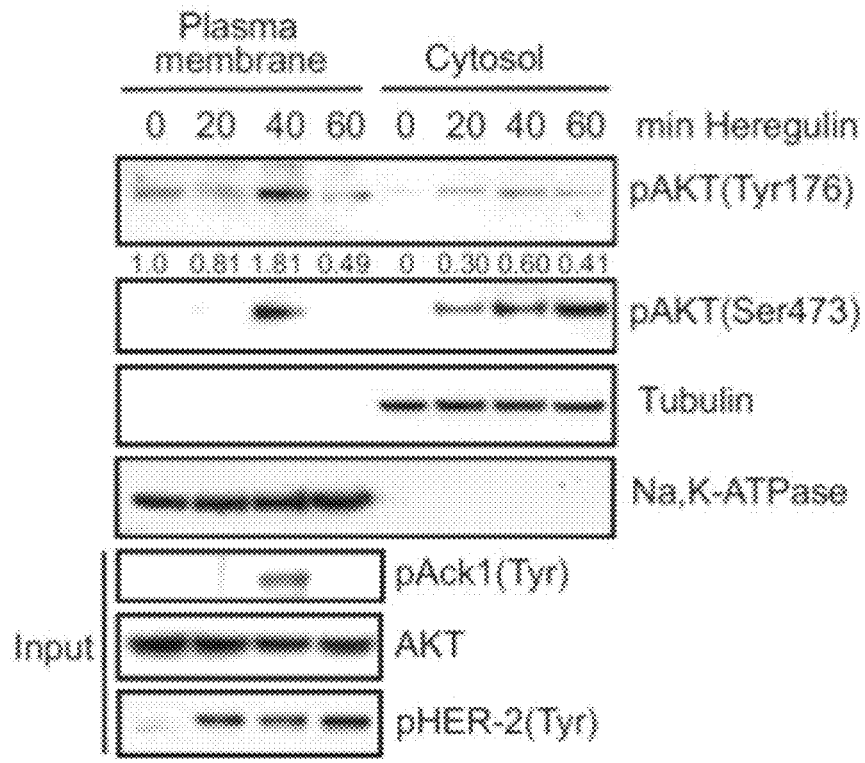

FIG. 28 is a blot showing Tyr176-phosphorylation regulates AKT plasma membrane localization. MCF-7 cells were serum starved (24 h) and treated (C) heregulin (30 ng/ml) for indicated times. Cell lysates were fractionated and IB with the indicated antibodies. Input panels pAck1 (Tyr), pIR(Tyr) and pHER-2(Tyr) represents IP with respective antibodies followed by IB with pTyr antibodies.

Figure 29:
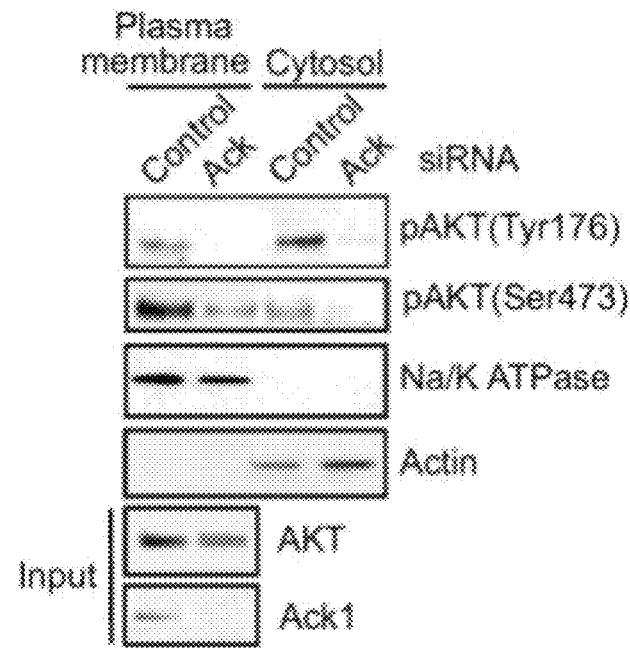

FIG. 29 is a blot showing Tyr176-phosphorylation regulates AKT plasma membrane localization. MCF7 cells were transfected with control or Ack1-specific siRNAs (40 nM) for 48 h and treated with heregulin for 40 mins. Cell lysates were fractionated and IB with indicated antibodies.

Figure 30:
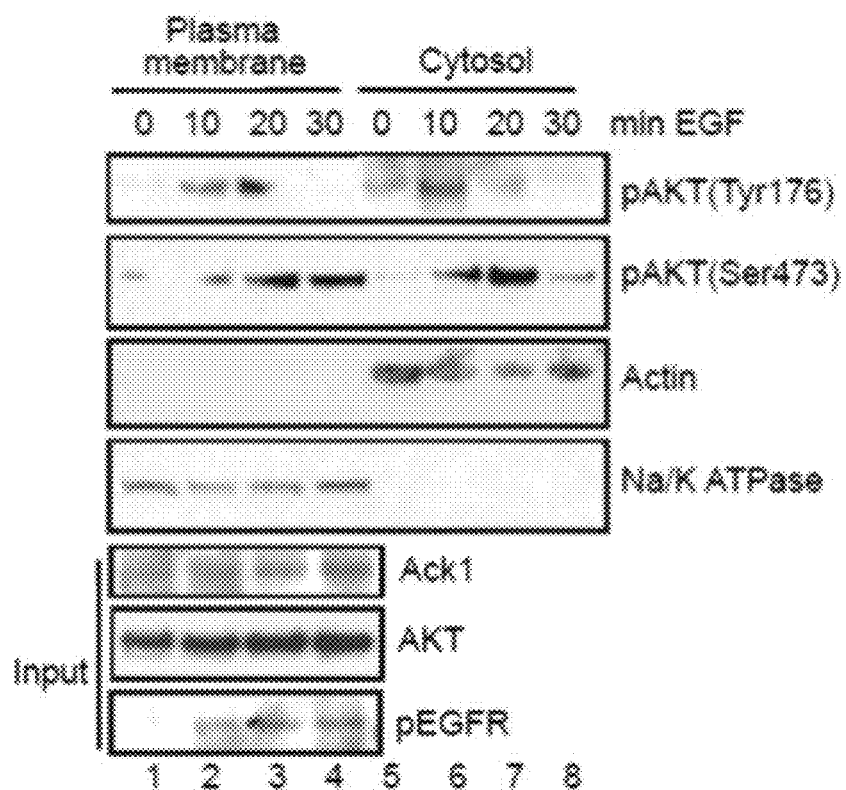

FIG. 30 is a blot showing the pTyr176-AKT localization to plasma membrane. RWPE cells were treated with EGF (10 ng/ml) for various time intervals and cell lysates were fractionated into plasma membrane and cytosolic fractions. Equal amounts of protein from these two fractions were subjected to immunoblotting with indicated antibodies. Tyr176-phosphorylated-AKT accumulates at the membrane upon 10 min of EGF addition.

Figure 31:
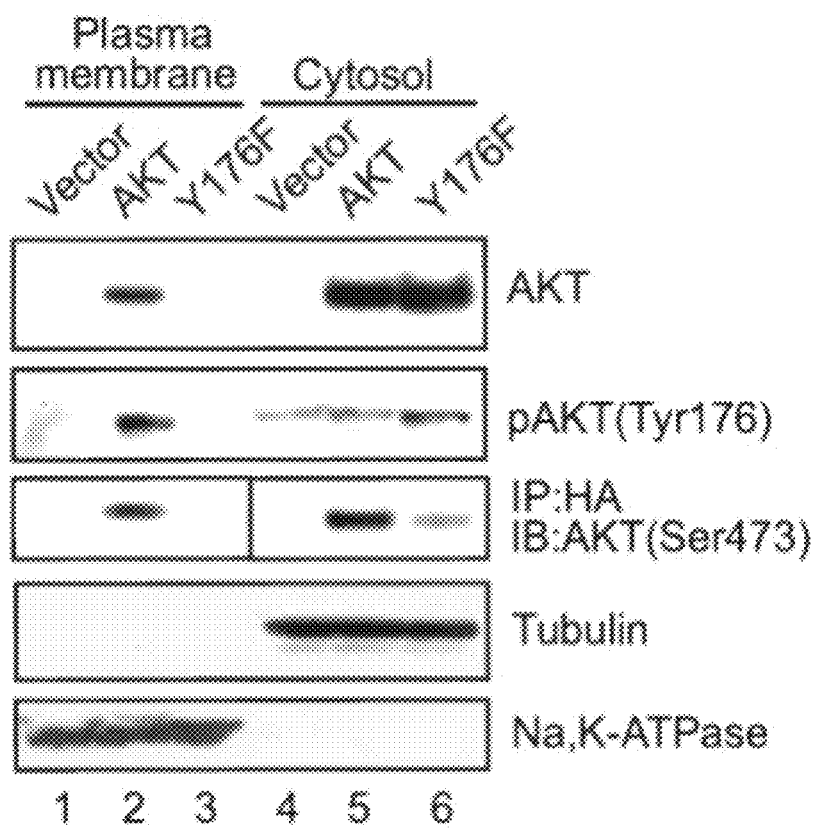
Figure 32:
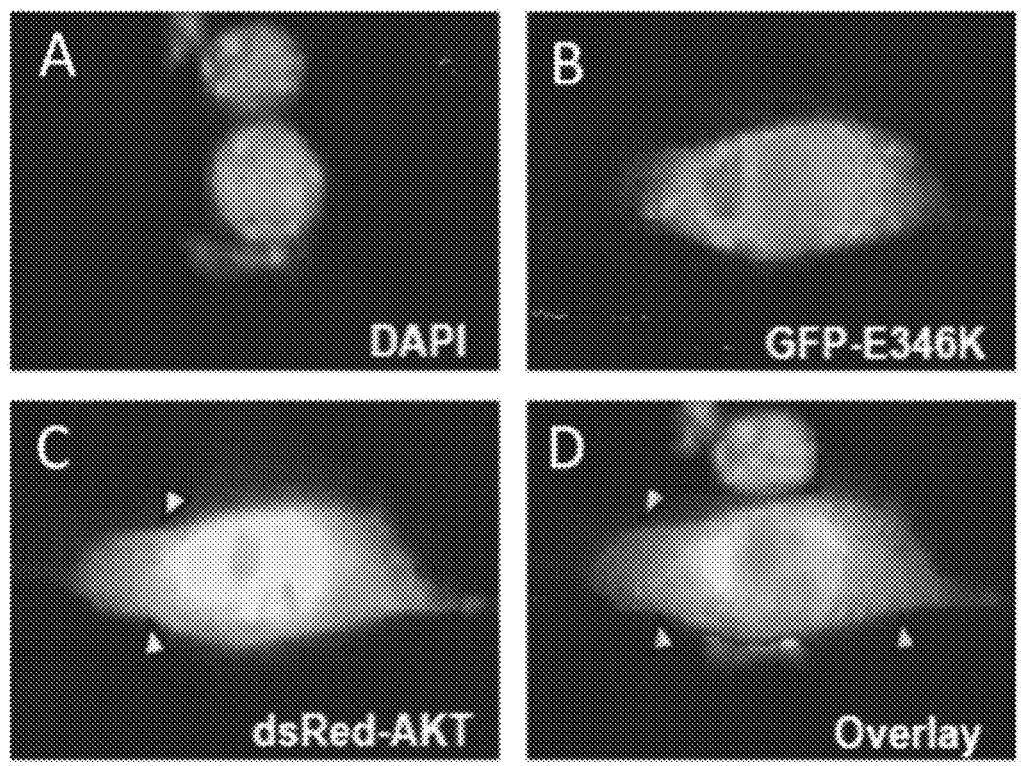
Figure 33:
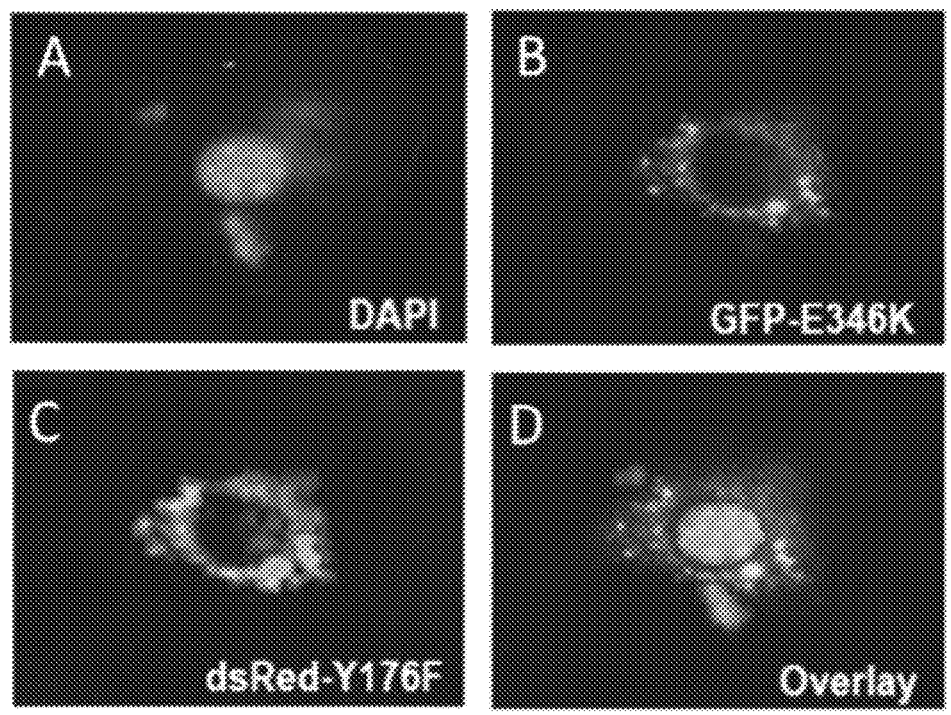

FIG. 31 is a blot showing Tyr176-phosphorylation regulates AKT plasma membrane localization. MEF 1&2KO cells were transfected with HA-tagged AKT or Y176F mutant, serum starved (24 h) and treated with EGF for 15 mins. Cell lysates were fractionated and IB with anti-HA (top panel) and indicated antibodies (bottom panels).

FIGS. 32(A) through (D) are immunohistochemical images showing the AKT localizes at plasma membrane. NIH3T3 cells were co-transfected with EGFP-E346K mutant of Ack1 and dsRed2-N1-AKT DNAs overnight. Cells were serum starved, fixed and stained for (A) DAPI; (B) dsRed-AKT; (C) GFP-E346K; or (D) an overlay composite. The images were visualized by fluorescence microscopy. AKT was localized to the plasma membrane in activated Ack1 (E346K) expressing cells.

FIGS. 33(A) through (D) are immunohistochemical images showing the Tyr176-phosphorylated AKT do not localize at plasma membrane. NIH3T3 cells were co-transfected with EGFP-E346K mutant of Ack1 and dsRed2-N1-Y176F-AKT DNAs overnight. Cells were serum starved, fixed and stained for (A) DAPI; (B) dsRed-AKT; (C) GFP-E346K; or (D) an overlay composite. The images were visualized by fluorescence microscopy. AKT but not Y176F mutant was localized to the plasma membrane in activated Ack1 (E346K) expressing cells.

Figure 34:
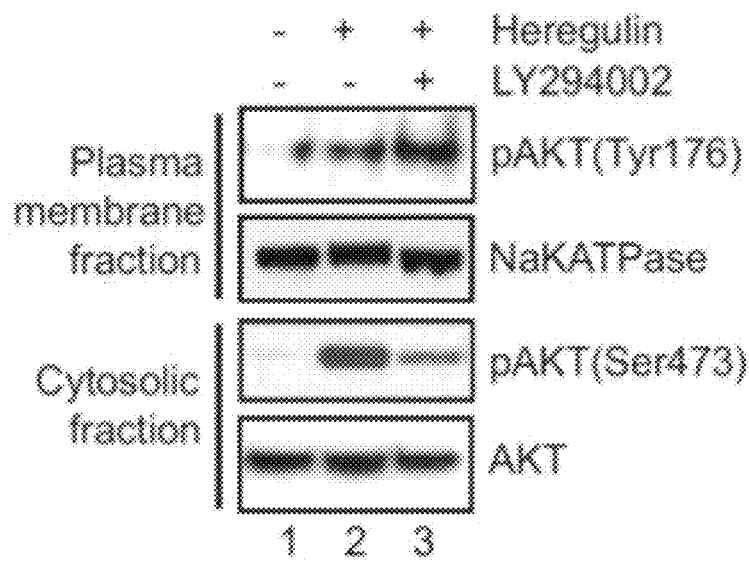

FIG. 34 is a blot showing Tyr176-phosphorylation of AKT is PI3K-independent. MCF-7 cells were pretreated with LY294002 (10 μM, 1 h) followed by heregulin for 40 mins. Cell lysates were fractionated and membrane fraction was subjected to IB with indicated antibodies.

Figure 35:
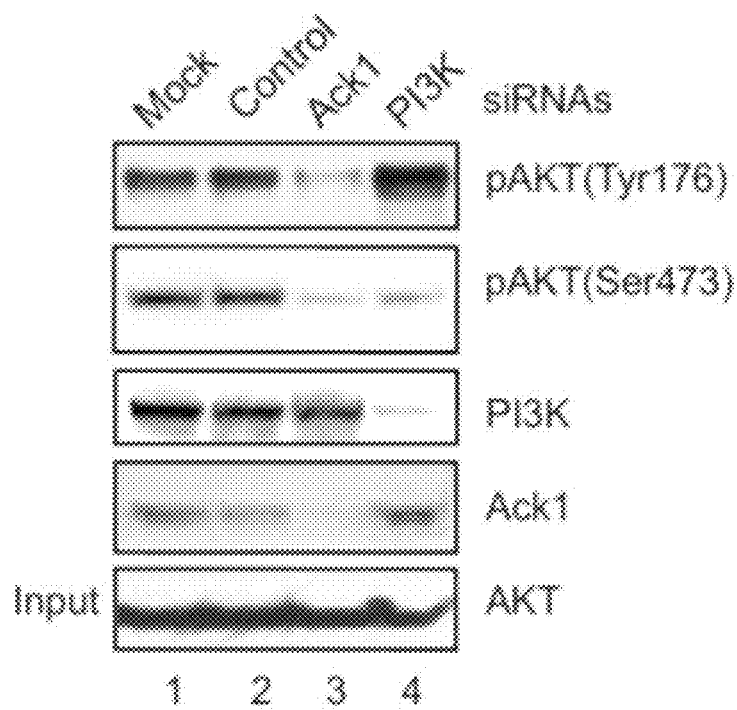

FIG. 35 is a blot showing Tyr176-phosphorylation of AKT is PI3K-independent. MCF-7 cells were mock transfected or transfected with control, Ack1 and PI3K siRNAs, followed by insulin treatment for 30 mins. Cell lysates were subjected to IP with pTyr-antibodies, followed by IB with pTyr176-AKT antibodies (top panel). Lower panels show IB with indicated antibodies. The experiment was performed with two different Ack1 siRNAs (Qiagen N.V., Germantown, Md.).

Figure 36:
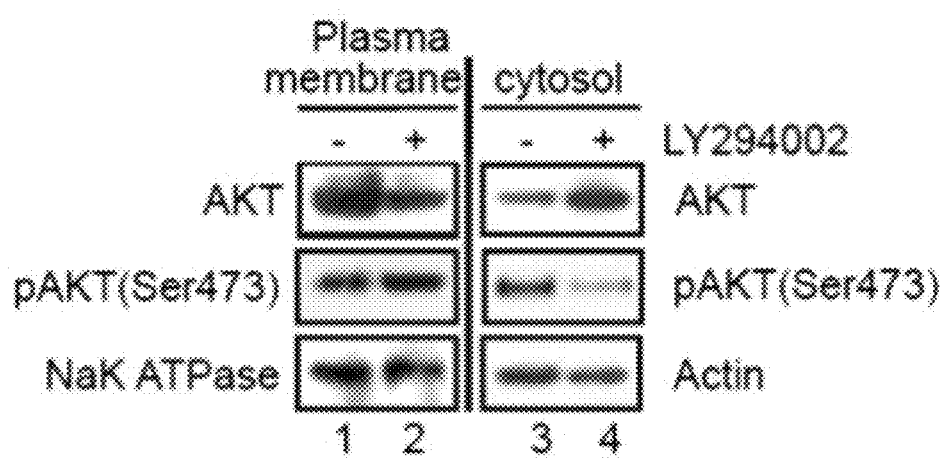

FIG. 36 is a blot showing Tyr176-phosphorylation of mutant AKT (R25C) that inefficiently binds phosphatidyl-inositol 3,4,5-triphosphate. MEF1&2KO cells were transfected with activated Ack and AKT followed by LY294002 (10 μM) for 1 h. Cell lysates were fractionated and subjected to immunoblotting with indicated antibodies. AKT Ser473 phosphorylation in membrane fraction was unaffected by LY294002 treatment suggesting Ack1 mediated AKT activation is not dependent upon PI3K activity.

Figure 37:
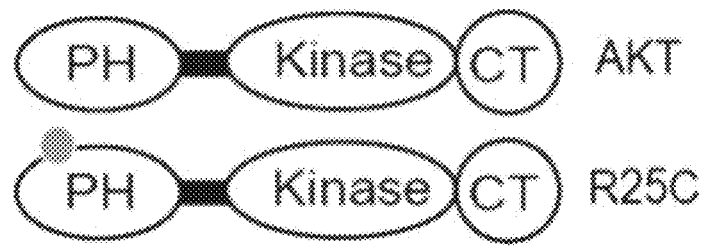

FIG. 37 is a schematic representation of wild type AKT and R25C point mutant. Site-directed mutagenesis of AKT was performed to generate the arginine to cystine, R25C, point mutant. PH, Pleckstrin homology domain; Kinase, Kinase domain and CT, Carboxy Terminal regulatory region.

Figure 38:
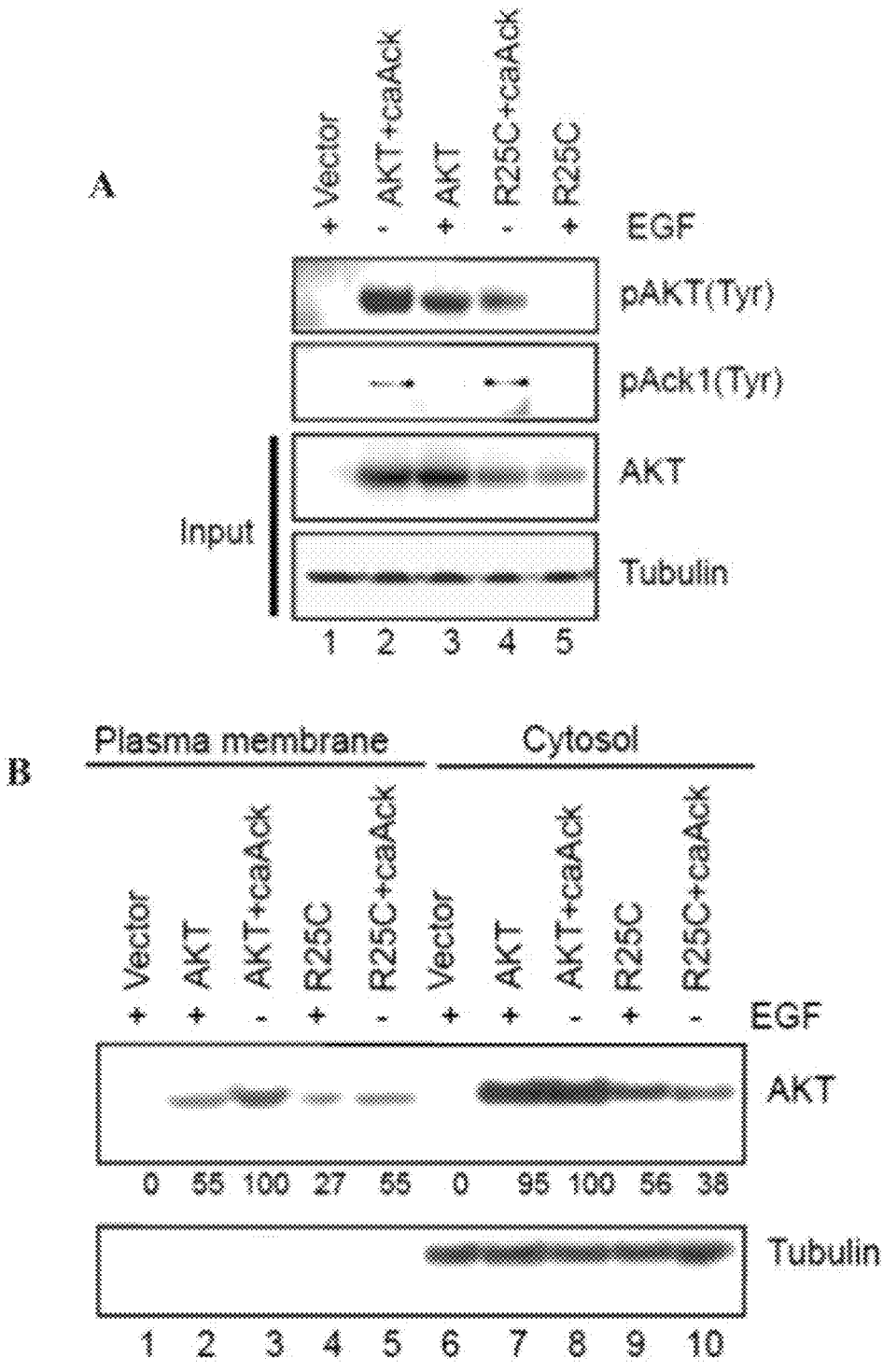
Figure 39:
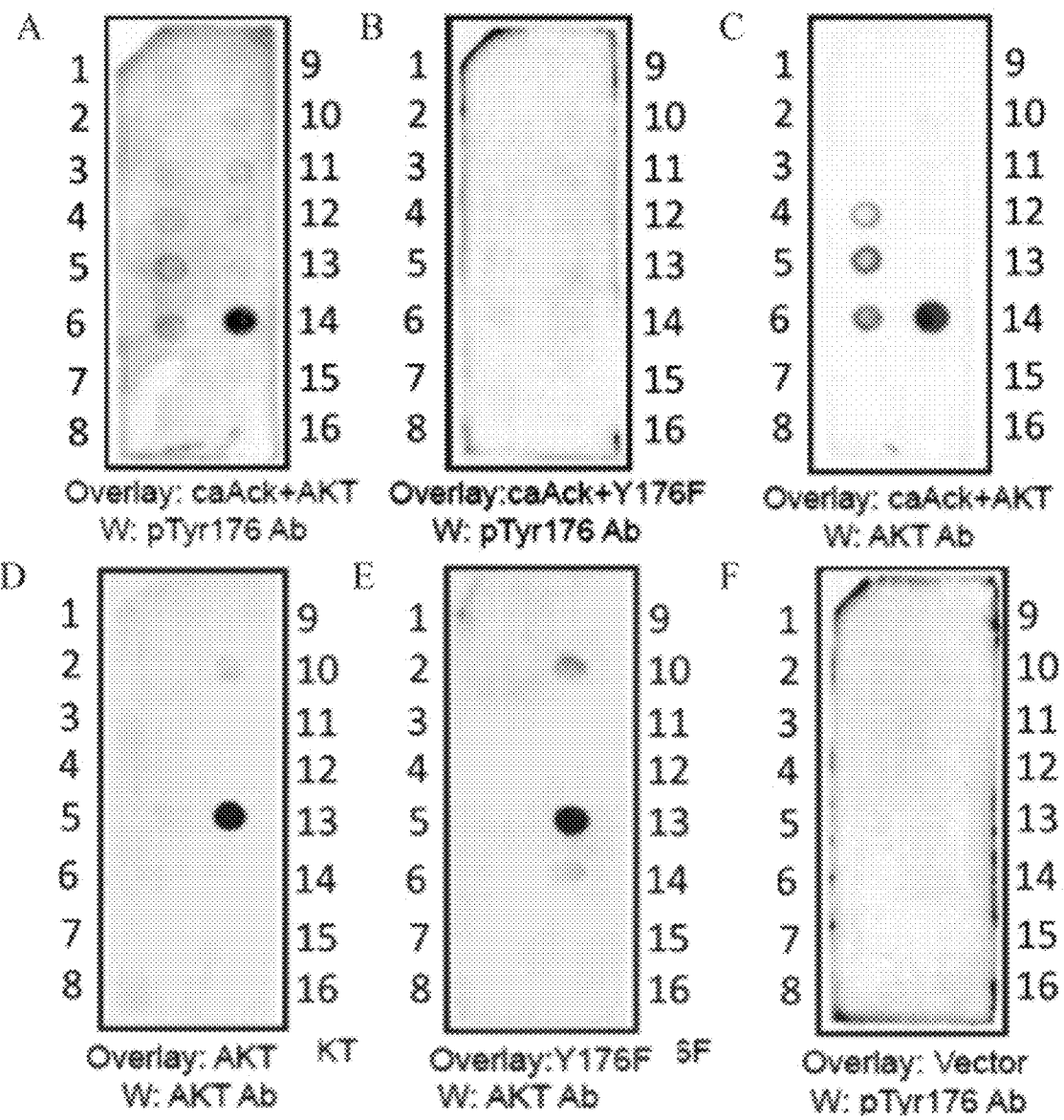

FIGS. 38(A) and (B) are blots showing Tyr176-phosphorylation of mutant AKT (R25C) inefficiently binds phosphatidyl-inositol 3,4,5-triphosphate. (AC) MEF1&2 KO cells were transfected with empty vector or caAck and HA-tagged AKT or R25C mutant DNAs. Serum starved (18 h) cells were treated with EGF (10 ng/ml, 15 mins). The lysates were subjected to immunoprecipitation with anti-HA (top panel) or anti-Ack1 (second panel) antibodies followed by immunoblotting with pTyr antibodies. (B) MEF1&2 KO cells were transfected with empty vector or caAck and HA-tagged AKT or R25C mutant DNAs. Serum starved (18 hr) cells were treated with EGF (10 ng/ml, 15 min). Cell lysates were fractionated and subjected to immunoblotting.

FIGS. 39(A) through (I) are images showing Tyr-phosphorylated AKT binds to phosphatidic acid. Proteinphospholipid overlay assay was performed using nitrocellulose membranes spotted with 100 pmol of different phospholipids. (A-G) Samples were immunoprecipitated and detected using the AKT or pTy176-AKT antibodies. The phospholipids immobilized on blot are as follows: 1: PA; 2:LPC; 3: PtdIns; 4: PtdIns(3)P; 5: PtdIns(4)P; 6: PtdIns(5)P; 7: PE; 8:PC; 9:SIP; 10: PtdIns(3,4)P$_2$; 11: PtdIns(3,5)P$_2$; 12: PtdIns(4,5)P$_2$; 13: PtdIns(3,4,5)P$_3$; 14: Phosphatidic acid; 15: Phosphatidylserine; 16: Blank. (A-C, F-G) Cells transfected with vector or activated Ack1 and AKT or Y176F were lysed and immunoprecipitated with pTyr-beads followed by elution with phenylphosphate. The eluted Tyr-phosphorylated proteins were incubated with phospholipid blots overnight at 4° C. Blots were extensively washed and bound proteins were detected with (A, B and F) pTyr176-AKT and (C and G) AKT antibodies. (D and E) Cells expressing HA-tagged (D) AKT and (E) Y176F mutant AKT were lysed and immunoprecipitated with HA-beads followed by elution with HA peptide. The eluate was incubated with phospholipid blots and bound proteins were detected with AKT antibodies. The pTyr176-AKT bound to phosphatidic acid, in contrast, AKT and Y176F mutant proteins bound primarily to phosphatidylinositol 3,4,5-triphosphate. (H and I) HA peptide and phenylphosphate eluate was immunoblotted with antibodies shown to confirm the presence of desired proteins.

FIG. 40 is a blot showing Tyr176 phosphorylated AKT is enriched in the nucleus. MCF-7 cells were serum starved (24 h) and treated with heregulin (30 ng/ml) for indicated times. Cell lysates were fractionated into nuclear and cytoplasmic fractions. Equal amounts of protein from these two fractions were subjected to immunoblotting with indicated Abs. Activated Ack1 mediated Tyr176 phosphorylated AKT is enriched in the nucleus 45 mins after heregulin treatment. The mobility of pTyr176-AKT is affected due to difference in the salt concentrations of nuclear (300 mM NaCl) and cytoplasmic fractions (10 mM KCl) (top panel).

Figure 41:
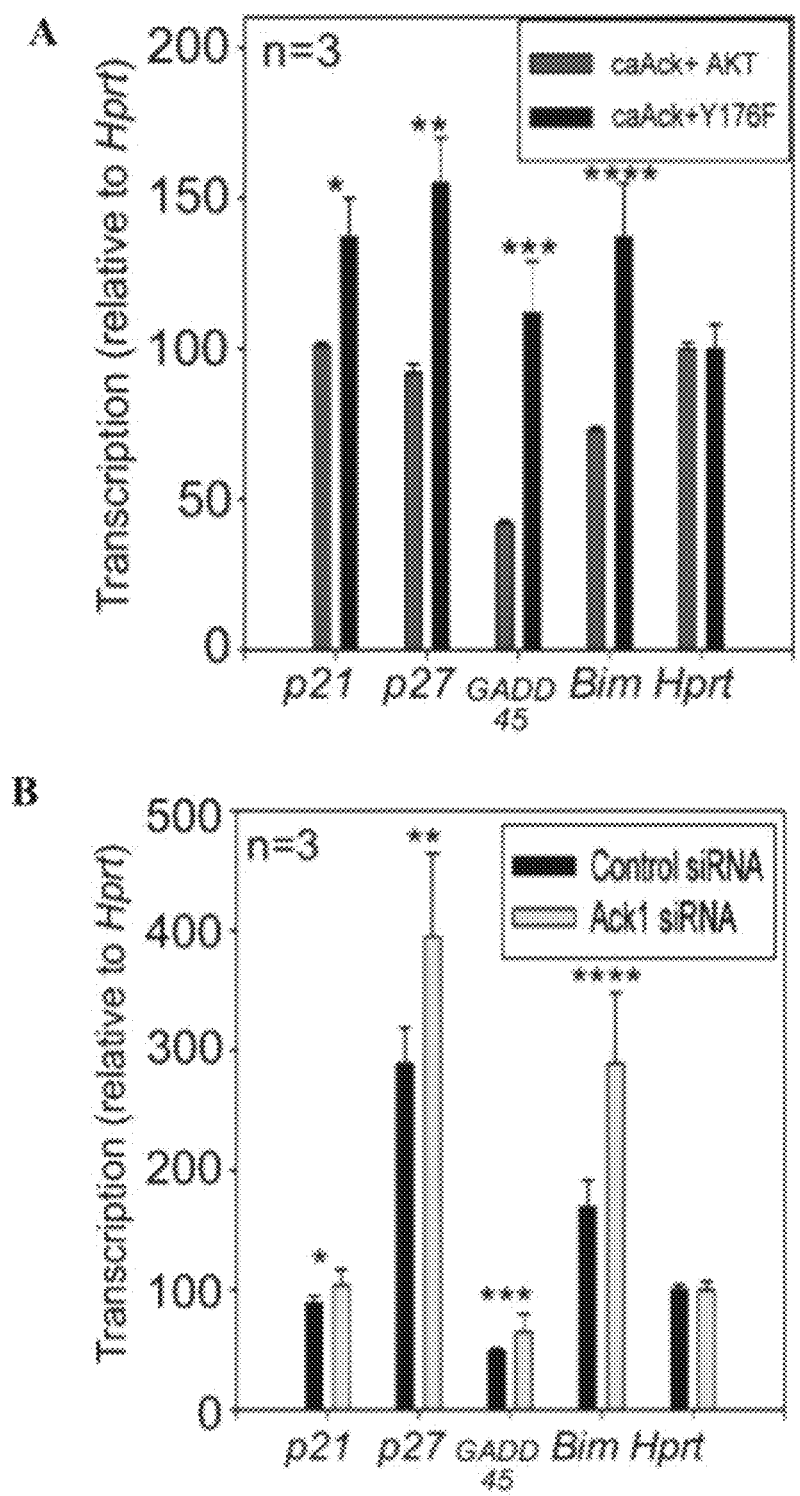

FIGS. 41(A) and (B) are graphs showing Tyr176 phosphorylated AKT suppresses FoxO gene transcription and promotes cell cycle progression. (A) MEF1&2KO cells were transfected with caAck and HA-taggedAKT orY176F, serum starved (24 h) and harvested. Total RNA was prepared and quantitative RT-PCR was performed. Data are representative of three independent experiments. *p≤0.05; p≤0.03; *p≤0.02; ****p≤0.02. (B) MEF2KO cells were transfected with control or Ack1-specific siRNAs (40 nM) for 48 h and treated with EGF for 30 mins. Total RNA was prepared and quantitative RT-PCR was performed. *p≤0.01;p≤0.05; *p≤0.06; **** p≤0.05.

Figure 42:
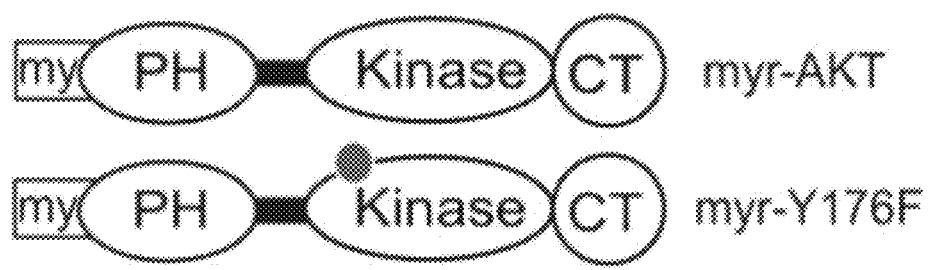

FIG. 42 is a schematic representation of myr-AKT and myr-Y176F point mutants. SDM of myr-AKT was performed to generate the Y176F mutation. PH, Pleckstrin homology domain; Kinase, Kinase domain and CT, Carboxy Terminal regulatory region.

Figure 43:
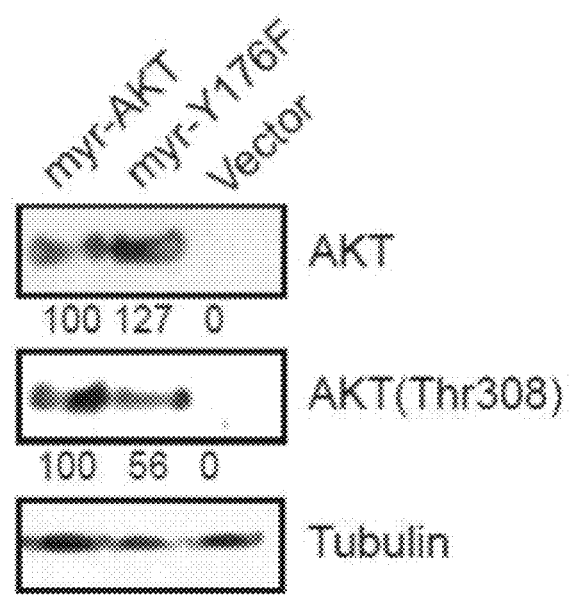
Figure 44:
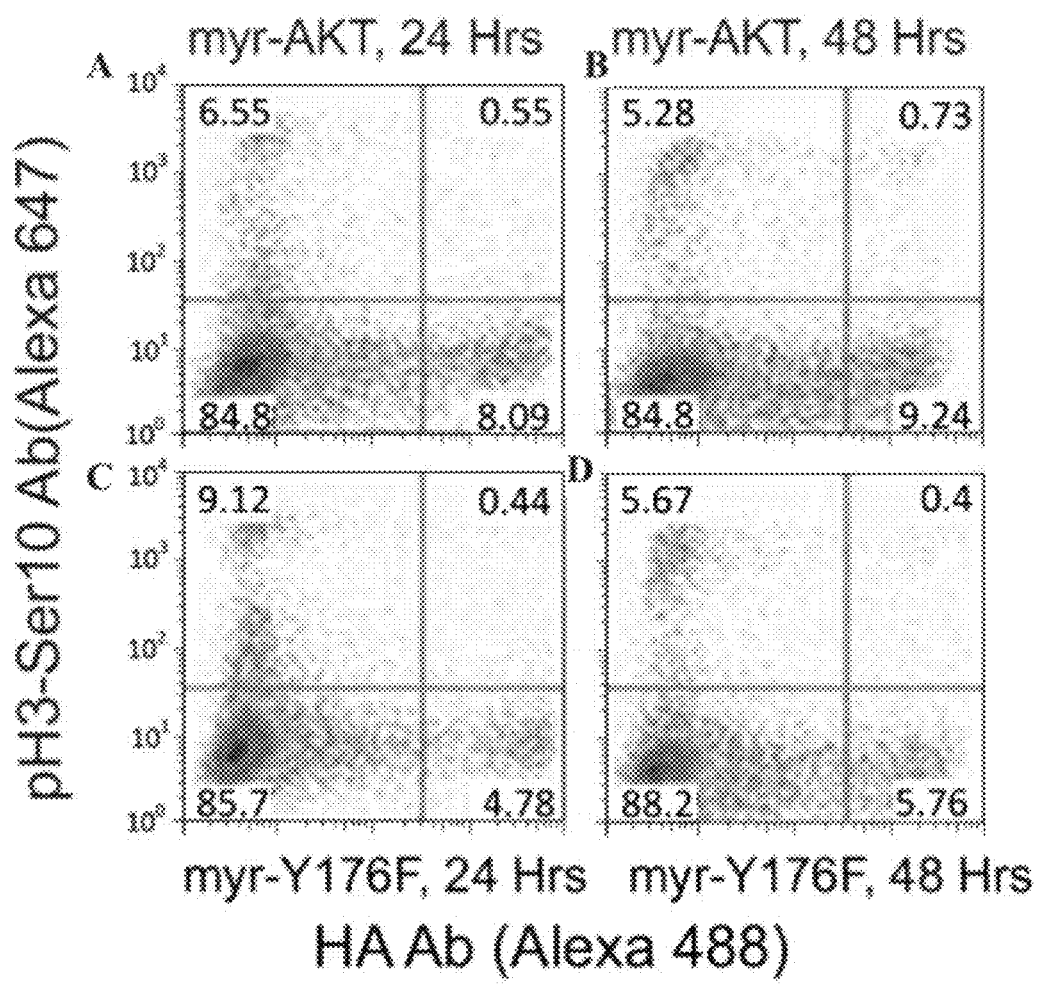

FIG. 43 is a blot showing expression of myr-AKT and myr-Y176F point mutants. MEF1&2KO cells were transfected with HA-tagged myr-AKT or myr-Y176F, equal amounts of protein lysates were subjected to immunoblotting as indicated. The myristoylated-AKT exhibits high levels of AKT activation, as seen by Thr308-phosphorylation.

FIGS. 44(A) through (D) graphs showing the flow cytometry for AKT MEF1&2 KO cells were transfected and harvested 24 h and 48 h post-transfection. Cells were fixed and stained with anti-HA antibodies conjugated with Alexa 488 and anti-pSerine10-Histone3 conjugated with Alexa 647, a marker used to distinguish cells in late G2 and early M phase, and analyzed by flow cytometry. (A) Cells were transfected with HA-tagged myr-AKT and harvested at 24 h. (B) Cells were transfected with HA-tagged myr-AKT and harvested at 48 h. (C) Cells were transfected with myr-Y176F mutant and harvested at 24 h. (D) Cells were transfected with myr-Y176F mutant and harvested at 48 h. HA-myrAKT expressing cells showed 75% increase in the number of cells undergoing mitosis (upper right quadrant), while, HA-myrY176F-AKT expressing mitotic cells remain unchanged.

Figure 45:
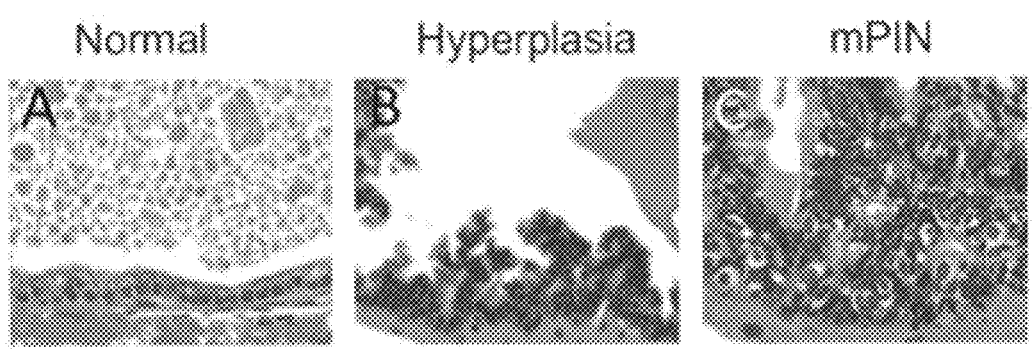

FIGS. 45(A) through (C) are hematoxylin and eosin (H&E) stained prostate section images showing probasin-Ack1 transgenic mice develop mPINs. H&E stained WT and TG mice prostates. Histological appearance of the prostate lateral lobe from (A) a normal 22 wk old WT mouse, and corresponding lobe from age-matched TG mice with (B) intraepithelial hyperplasia. (C) The lateral prostate from 49 wk old TG mice exhibiting mPIN is shown.

FIGS. 46(A) through (F) are immunohistochemistry images showing probasin-Ack1 transgenic mice develop mPINs. H&E stained WT and TG mice prostate sections. Contrasting histological appearance of the lateral, ventral and dorsal lobes of the prostate glands from a WT mouse (A-C), and corresponding lobes from TG mice (49 week old) are shown (D-F).

Figure 47:
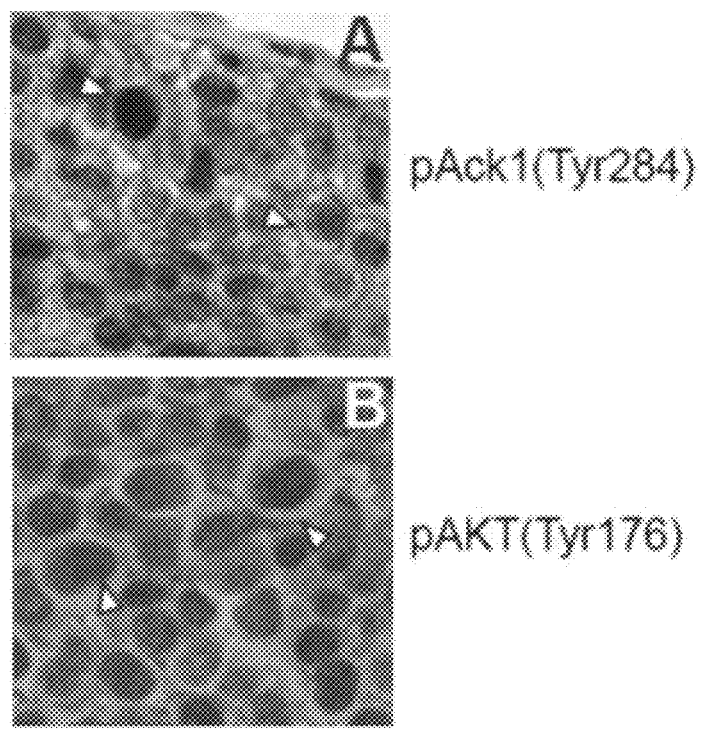
Figure 48:
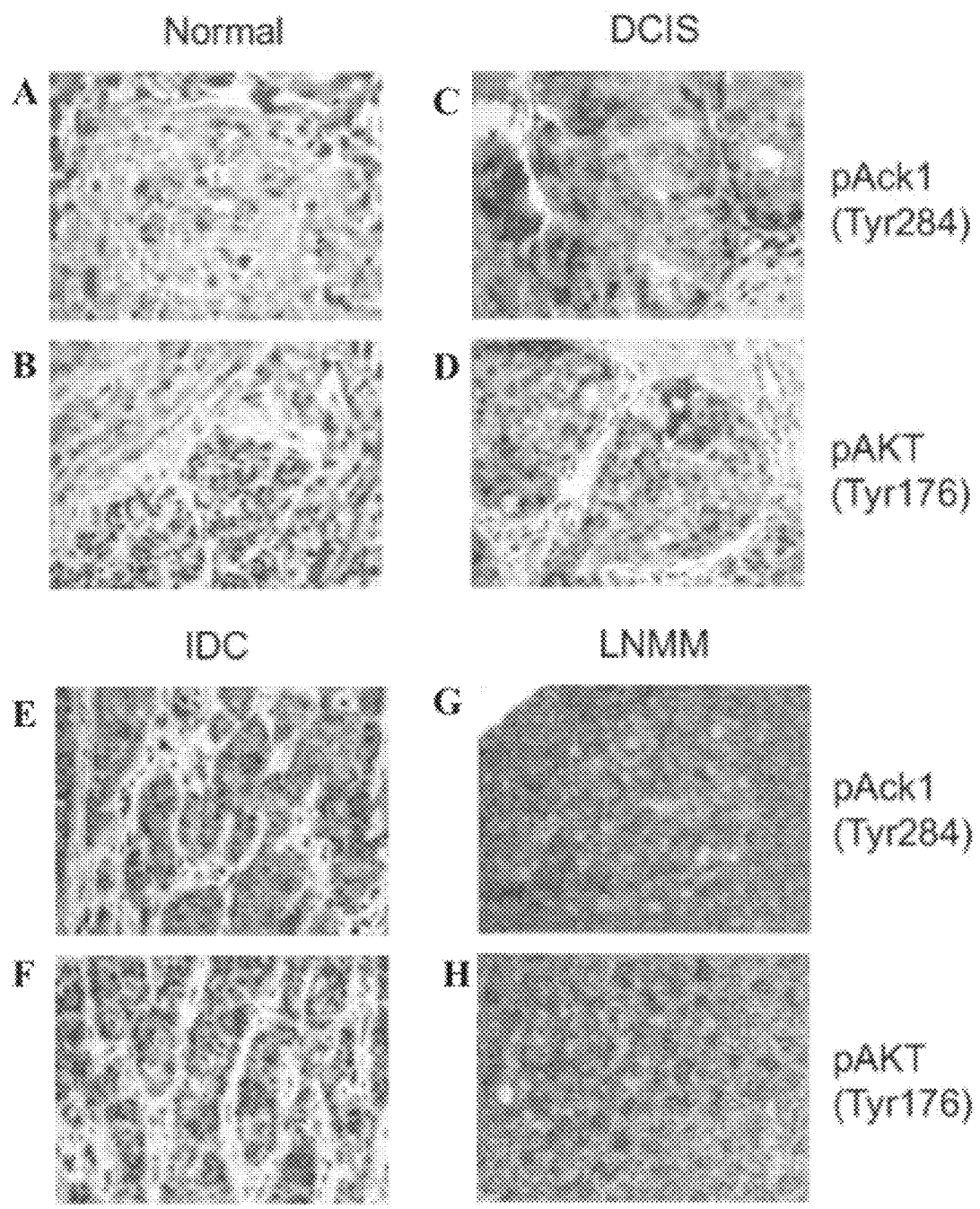

FIGS. 47(A) and (B) are immunohistochemistry images staining tumor samples with Tyr284-phosphorylated-Ack1 and Tyr176-phosphorylated-AKT antibodies. Representations of (A) Tyr284-phosphorylated-Ack1 and (B) Tyr176-phosphorylated-AKT staining of IDC, which show intense staining in nuclei and membrane.

FIGS. 48(A) through (H) are immunohistochemistry images showing pTyr284-Ack1 and pTyr176-AKT expression in breast cancer. (A-H) TMA sections representing different breast cancer stages stained with pTyr284-Ack1 and pTyr176-AKT antibodies.

Figure 49:
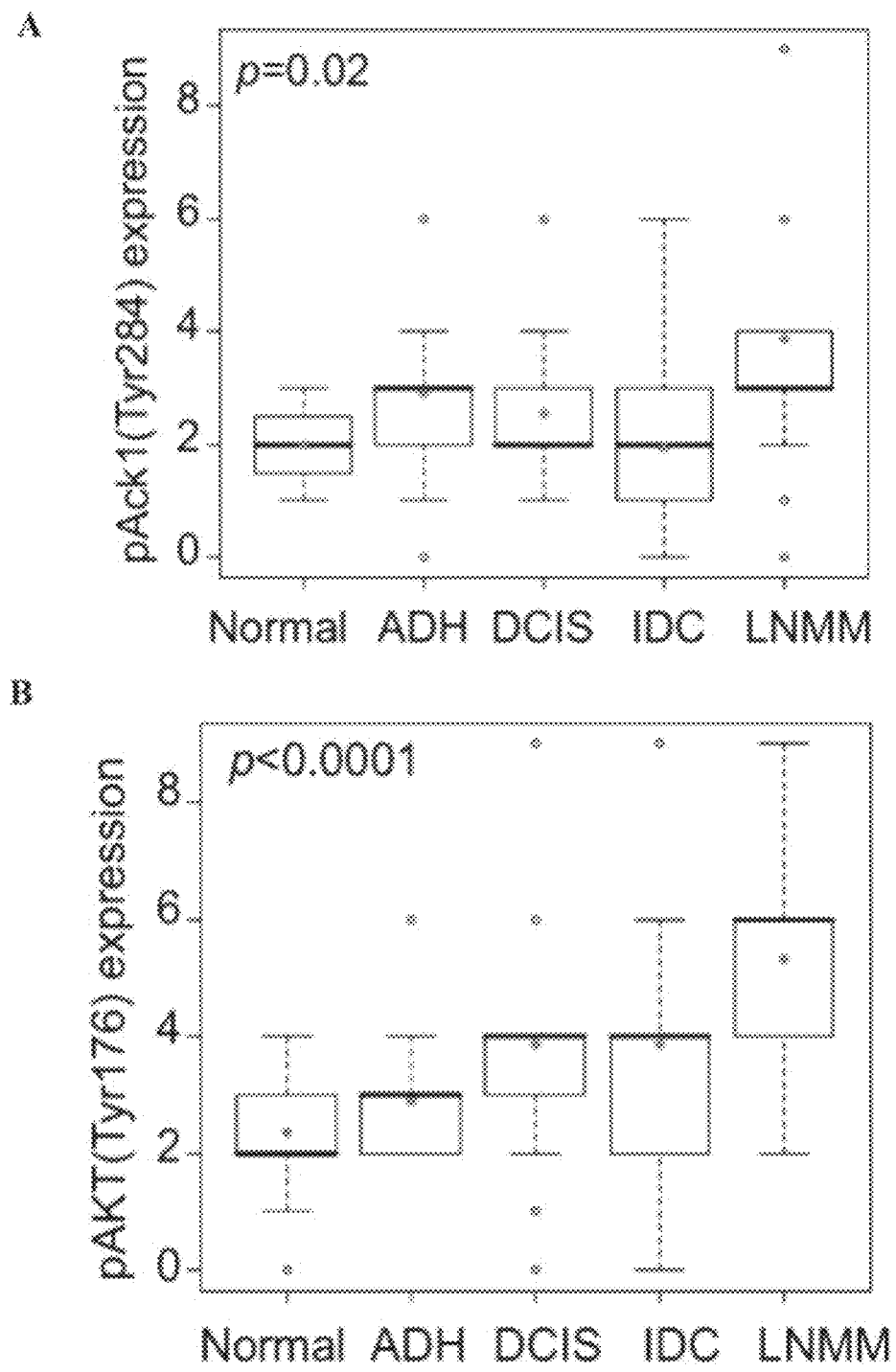

FIGS. 49(A) and (B) are plots showing pTyr284-Ack1 and pTyr176-AKT expression in breast cancer. (A) Box plots to summarize distributions of staining intensities for pTyr284-Ack1 in different stages of breast cancer. A significant increasing trend of intensity across progression stages was detected (Mantel-Haenszel $\chi^2$ test, p=0.02). The box has lines at the lower quartile (25%), median (50%), and upper quartile values (75%) while the red-cross within the circle marks the mean value. Whiskers extend from each end of the box to the most extreme values within 1.5 times the interquartile range from the ends of the box. The data with values beyond the ends of the whiskers, displayed with black circles, are potential outliers. (B) Box plots to summarize distributions of staining intensities for pTyr176-AKT in different stages of breast cancer. A significant increasing trend of intensity across progression stages was detected (Mantel-Haenszel $\chi^2$ test, p<0.0001).

FIGS. 50(A) through (D) are immunohistochemistry images staining tumor samples with Tyr284-phosphorylated-Ack1 and Tyr176-phosphorylated-AKT antibodies. Breast samples stained with Ack1 and pTyr284-Ack1 antibodies. Basal levels of Ack1 expression were seen in both normal and tumor samples (A, B), however, significant increase in pTyr284-Ack1 staining was seen in tumor samples as contrast to normal breast sample (compare C and D).

Figure 51:
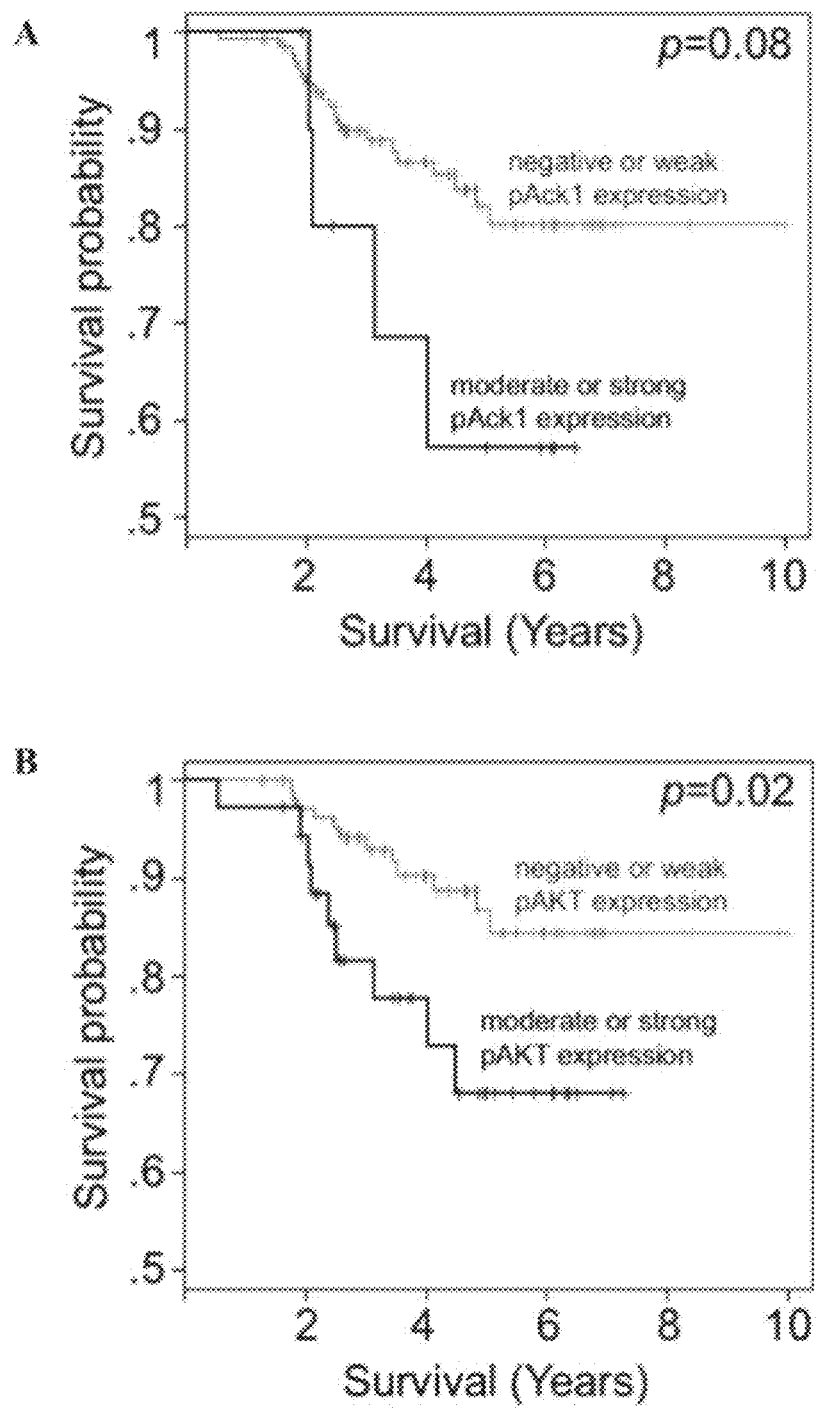

FIGS. 51 (A) and (B) are plots showing breast cancer pTyr284-Ack1 and pTyr176-AKT expression. (A) Kaplan-Meier analysis shows that individuals with breast cancer that have moderate to strong staining (>4) of pTyr284-Ack1 have a lower probability of survival (log rank test, p=0.08). (B)

Kaplan-Meier analysis of the breast cancer patients that have moderate to strong staining (>4) of pTyr176-AKT have significantly lower probability of survival (log rank test, p=0.02).

DETAILED DESCRIPTION OF THE PREFERRED EMBODIMENT

The present invention provides compositions and methods for identifying cancers resistant to treatment due to the presence of elevated pTyr176-AKT levels, particularly breast, prostate, lung, ovarian, brain, blood and pancreatic cancers. Protein expression is compared to a control, such as a demographic sampling of a population, or compared to the total protein for that specific protein of interest. The methods comprise the detection of Tyr176-phosphorylated AKT and/or pTyr284-Ack1. The protein expression may alternatively be determined by examining the expression spatially throughout a sample cell, such as examining the expression patterns of phosphorylated proteins of interest in the cell membrane and the nucleus.

As used herein, the term AKT 'translocation' indicates emergence of (cytosolic) AKT in the plasma membrane in response to growth factors.

As used herein, the term "precancerous" refers to cells or tissues that have characteristics relating to changes that may lead to malignancy or cancer, such as mutations controlling cell growth and proliferation. Examples include adenomatous growths in breast and prostate tissue, or for example, conditions of dysplastic nevus syndromes, polyposis syndromes, prostatic dysplasia, and other neoplasms, whether clinically identifiable or not.

As used herein, the term "siRNA" refers to small interfering RNAs, which also include short hairpin RNA (shRNA) (Paddison, et al. Short hairpin RNAs (shRNAs) induce sequence-specific silencing in mammalian cells. Genes Dev. Apr. 15; 16(8):948-58) and microRNA (miRNA) (For general information see, Nature Reviews micorRNA collection (Skipper, M., ed.), Nature Publishing Group, 2007), that are capable of interfering with the protein translation, transcription, or cause post-transcriptional silencing. The siRNAs are capable of causing interference, resulting in transcritpional silencing of specific gene products in cells and organisms.

As used herein, "subject" means humans, nonhuman primates, rabbits, dogs, cats, sheep, goats, horses, cows, pigs and rodents. In particular, the "subjects" of the present invention are organisms in need of diagnosis or treatment for a cancer or pre-cancer or lesion thereof.

As used herein, "differential expression" refers to the difference in the amount of transcription products from nucleic acid transcription present in a cell. The transcriptional products are preferably proteins. The transcription may occur from any nucleic acid known in the art, including DNA, RNA, expression vectors, foreign DNA or RNA, whether integrated into the cell DNA or not, such as viral nucleic acids capable of transcription.

Since its identification as a downstream target of the RTKs, Ack1 has emerged as a critical early transducer of variety of extracellular growth factor stimuli e.g. heregulin, EGF, PDGF (Mahajan, N. P., Whang, Y. E., Mohler, J. L. & Earp, H. S. Activated tyrosine kinase Ack1 promotes prostate tumorigenesis: role of Ack1 in polyubiquitination of tumor suppressor Wwox. *Cancer Res* 65, 10514-10523 (2005); Mahajan, N. P., et al. Activated Cdc42-associated kinase Ack1 promotes prostate cancer progression via androgen receptor tyrosine phosphorylation. *Proc Natl Acad Sci USA* 104, 8438-8443 (2007); Galisteo, M. L., Yang, Y., Urena, J. & Schlessinger, J. Activation of the nonreceptor protein tyrosine kinase Ack by multiple extracellular stimuli. *Proc Natl Acad Sci USA* 103, 9796-9801 (2006); Shen, F., Lin, Q., Gu, Y., Childress, C. & Yang, W. Activated Cdc42-associated kinase 1 is a component of EGF receptor signaling complex and regulates EGF receptor degradation. *Mol Biol Cell* 18, 732-742 (2007); van der Horst, E. H., et al. Metastatic properties and genomic amplification of the tyrosine kinase gene ACK1. *Proc Natl Acad Sci USA* 102, 15901-15906 (2005)) and integrin signaling (Modzelewska, K., Newman, L. P., Desai, R. & Keely, P. J. Ack1 mediates Cdc42-dependent cell migration and signaling to p130Cas. *J Biol Chem* 281, 37527-37535 (2006)).

A novel signaling pathway using RTK/Ack1 pathway was identified that plays a key role in regulating AKT activity. A significant proportion of breast and pancreatic tumors display not only high levels of expression of the phosphorylated forms of Ack1 and AKT but also significant correlation in co-expression of Tyr284-phosphorylated-Ack1 and Tyr176-phosphorylated-AKT in the same tumor, which in turn correlates highly with progression of disease. A small proportion of the tumors exhibit poor pTyr284-Ack1 staining but were strong for pTyr176-AKT staining, suggesting that other receptor or non-receptor tyrosine kinases perhaps directly target AKT for Tyr176-phosphorylation. Tyr-phosphorylation of AKT at Tyr315, Tyr326 and Tyr474 have been reported earlier (Datta, K., Bellacosa, A., Chan, T. O. & Tsichlis, P. N. Akt is a direct target of the phosphatidylinositol 3-kinase. Activation by growth factors, v-src and v-Ha-ras, in Sf9 and mammalian cells. *The Journal of biological chemistry* 271, 30835-30839 (1996); Li, H. L., Davis, W. W., Whiteman, E. L., Birnbaum, M. J. & Pure, E. The tyrosine kinases Syk and Lyn exert opposing effects on the activation of protein kinase Akt/PKB in B lymphocytes. *Proceedings of the National Academy of Sciences of the United States of America* 96, 6890-6895 (1999); Chen, R., et al. Regulation of Akt/PKB activation by tyrosine phosphorylation. *The Journal of biological chemistry* 276, 31858-31862 (2001); Conus, N. M., Hannan, K. M., Cristiano, B. E., Hemmings, B. A. & Pearson, R. B. Direct identification of tyrosine 474 as a regulatory phosphorylation site for the Akt protein kinase. *The Journal of biological chemistry* 277, 38021-38028 (2002)). Multiple non-receptor tyrosine kinases, e.g. Src, Syk, Btk, Lyn were shown to be involved in AKT Tyr-phosphorylation at Tyr315, Tyr326 and Tyr474 sites, which correlated with increased kinase activity (Li, H. L., Davis, W. W., Whiteman, E. L., Birnbaum, M. J. & Pure, E. The tyrosine kinases Syk and Lyn exert opposing effects on the activation of protein kinase Akt/PKB in B lymphocytes. *Proceedings of the National Academy of Sciences of the United States of America* 96, 6890-6895 (1999)). However, the precise mechanism of AKT activation by Tyr315, Tyr326 and Tyr474 phosphorylations was not clear, nor was their role in initiation or progression of cancer. This report provides the first demonstration of role of Tyr176-phosphorylated AKT in its compartmentalization, which allowed delineation of its role in AKT kinase activation and its ability to initiate neoplasia and promote disease progression in human cancers.

While in about 50% of human breast cancers, hyperactivation of AKT can occur either by the catalytically activating mutations in PI3K (21.4%), mutations in PTEN tumor suppressor (2.3%) (Stemke-Hale, K., et al. An integrative genomic and proteomic analysis of PIK3CA, PTEN, and AKT mutations in breast cancer. *Cancer research* 68, 6084-6091 (2008)), or epigenetic changes in PTEN (30%) (Hennessy, B. T., Smith, D. L., Ram, P. T., Lu, Y. & Mills, G. B. Exploiting the PI3K/AKT pathway for cancer drug discovery. *Nat Rev Drug Discov* 4, 988-1004 (2005)), the molecular mechanisms regulating RTK mediated AKT activation in cancers with normal PTEN and PI3K activity are poorly understood (Tibes, R., et al. PI3K/AKT pathway activation in acute myeloid leukaemias is not associated with AKT1 pleckstrin homology domain mutation. *British journal of haematology* 140, 344-347 (2008)). Transgenic mouse model with mutant polyomavirus (PyV) middle T antigen (MT) that is decoupled from PI3K interaction, develop mammary gland hyperplasias unlike wild type PyV MT-induced multifocal metastatic tumors (Webster, M. A., et al. Requirement for both Shc and phosphatidylinositol 3' kinase signaling pathways in polyomavirus middle T-mediated mammary tumorigenesis. *Molecular and cellular biology* 18, 2344-2359 (1998)). The focal mammary tumors that eventually arose display upregulated ErbB-2 and ErB-3 growth factor receptors, suggesting that these tumors may use alternative mechanisms to activate AKT when the PI3K pathway is suppressed. Consistent with this idea, double transgenic mice, expressing a constitutively activated form of AKT in a PyV-MT mutant is able to convert mammary gland hyperplasias to multifocal mammary tumors, suggesting that activation of AKT is critical for tumorigenesis (Hutchinson, J., Jin, J., Cardiff, R. D., Woodgett, J. R. & Muller, W. J. Activation of Akt (protein kinase B) in mammary epithelium provides a critical cell survival signal required for tumor progression. *Molecular and cellular biology* 21, 2203-2212 (2001)). The data showed that even in the presence of PI3K inhibitor, activation of ErbB-2 or EGFR promotes robust activation of Ack1 which in turn phosphorylated and activated AKT, suggesting that RTK/Ack1 pathway can function independent of the RTK/PI3K pathway under specific conditions. In support of this hypothesis, in a mouse model with the deletion of the gene encoding the different subunits of PI3K, $p85\alpha^{-/-}$ $p55\alpha^{-/-}$ $p50\alpha^{-/-}$, PI3kr1, AKT activation (Ser473 phosphorylation) occurs in insulin treated cells, in spite of reduction in total PI3K levels, clearly suggesting that other pathways contribute to AKT activation (Fruman, D. A., et al. Hypoglycaemia, liver necrosis and perinatal death in mice lacking all isoforms of phosphoinositide 3-kinase p85 alpha. *Nature genetics* 26, 379-382 (2000)). Further, it was observed that the serum-starved MCF-7 cells exhibited robust AKT Tyr176-phosphorylation, membrane localization, followed by AKT activation (Ser473/Thr308 phosphorylation) upon insulin treatment (K.M. and N.P.M., unpublished data), indicating that Ack1 could potentially substitute PI3K activity to accomplish AKT membrane targeting and activation. Future studies will be aimed at understanding whether Ack1 is preferentially employed by insulin treated cells when PI3K mediated AKT activation is compromised.

While major research has been focused on AKT activation via PI3K pathway, mechanisms of PI3K-independent AKT activation in cancers cannot be entirely precluded. A rare somatic mutation (E17K) has recently been identified in AKT PH-domain that increases AKT membrane localization and activation in the absence of PIP3, leading to cellular transformation and leukemiagenesis in mice (Carpten, J. D., et al. A transforming mutation in the pleckstrin homology domain of AKT1 in cancer. *Nature* 448, 439-444 (2007)). Somatic auto-activating mutation in Ack1 (E346K) was shown to promote AKT Tyr176-phosphorylation and kinase activation in low PIP3 environment. Based on this observation, it is likely that cancers that display amplification or somatic autoactivation of receptor tyrosine kinases or non receptor tyrosine kinases could exhibit upregulated AKT activity despite of normal PI3K/PTEN levels.

Transgenic mice expressing constitutively active, i.e. myristoylated AKT, in prostate do not develop cancer (Majumder, P. K., et al. Prostate intraepithelial neoplasia induced by prostate restricted Akt activation: the MPAKT model. *Proc Natl Acad Sci USA* 100, 7841-7846 (2003)). However, Ack1 TG mice display robust AKT Tyr176-phosphorylation, form mPINs, that progress to invasive adenocarcinoma. It is likely that Ack1 mediated AKT Tyr176-phosphorylation is a key event that initiates neoplasia and precedes AR and Wwox phosphorylation, which are primarily involved in progression of prostate cancer to androgen-independence.

Mouse embryo fibroblasts derived from AKT1, AKT2 and AKT1&2 knockout mice were obtained from Dr. Morris J. Birnbaum, University of Pennsylvania, Philadelphia. Human Embryonic Kidney cell line 293T, normal prostate cell line RWPE and MCF-7 cells were obtained from the American Type Tissue Culture Collection. Ack1 mAb (A11), alpha-tubulin (TU-O2), Actin (1-19), EGFR(1005), pTyr(PY20) HRP conjugate antibodies purchased from Santacruz; Anti-phospho-Ack1 (Tyr284, Upstate); phospho-AKT (Thr308, C31E5E), phospho-AKT (Ser473, D9E), AKT (Panigrahi A R, et al. (2004) The role of PTEN and its signalling pathways, including AKT, in breast cancer; an assessment of relationships with other prognostic factors and with outcome. *J Pathol* 204: 93-100) (C67E7 Rabbit mAb), AKT1(C73H10 Rabbit mAb), AKT2(5B5 Rabbit mAb), phospho-AKT (Ser473, 193H12) Rabbit mAb Alexa Fluor 647 conjugate, HA-Tag (6E2) Mouse mAb Alexa Fluor 488, phosphoHistone H3-Serine10 Alexa Fluor 647 conjugate antibodies and LY294002 purchased from Cell Signaling, NaKATPase (ab7671, Abcam, Inc., Cambridge, Mass.), c-erbB-2/Her2/neu Ab-2 (Clone 9G6.10) (Thermo Fisher Scientific Inc., Waltham, Mass.) antibodies were purchased from the respective companies. Site directed mutagenesis was performed to generate the AKT(Y176F), AKT(R25C), myrAKT (Y176F), Ack1 (E346K), Ack1 (R34L), Ack1 (R99Q) and Ack1 (H4091) constructs according to the manufacturer's protocol (Promega Corp., Madison, Wis.). EGFP-E346K and DsRed2-N1-AKT (WT and Y176F) were generated by subcloning E346K and AKT cDNAs into the pEGFP-N1 and pDsRed2-N1 (Clontech Laboratories/Takara Bio USA, Madison, Wis.) vectors respectively. Control and Ack1 siRNAs were generated by custom synthesis (Qiagen N.V., Germantown, Md.) and the sequences have been described previously (Mahajan N P, et al. (2007) Activated Cdc42-associated kinase Ack1 promotes prostate cancer progression via androgen receptor tyrosine phosphorylation. *Proc Natl Acad Sci USA* 104: 8438-8443). PI3K siRNAs (SC39127) and antibodies were purchased from Santacruz.

AKT phosphoTyr176-site determination using mass spectrometry. 293T cells co-expressing activated Ack and HA-tagged AKT were lysed in receptor lysis buffer (RLB) containing 25 mmol/L Tris (pH 7.5), 225 mmol/L NaCl, 1% Triton X-100, 1 mmol/L DTT, 10% glycerol, phosphatase inhibitors (10 mmol/L NaF, 1 mmol/L $Na_2VO_4$), and protease inhibitor mix (Hoffmann-La Roche Inc., Switzerland). Following immunoprecipitation with HA-beads (E6779, Sigma-Aldrich Co., St. Louis, Mo.), purified AKT was subjected to SDS PAGE electrophoresis and the gel was stained Coomassie Brilliant Blue-R250(BioRad). A prominent band of ~59 kDa was excised, washed once with water and twice with 50 mM ammonium bicarbonate in 50% aqueous methanol. Proteins were reduced and alkylated with 2 mM Tris(2-carboxyethyl)phosphine hydrochloride (TCEP) (Sigma-Aldrich Co., St. Louis, Mo.) and 20 mM iodoacetamide (GE Healthcare, Pittsburgh, Pa.), respectively. Samples were digested overnight with modified sequencing grade trypsin (Promega Corp., Madison, Wis.), Glu-C (Worthington, Lakewood, N.J.), or chymotrypsin (Hoffmann-La Roche Inc., Switzerland). Peptides were extracted from the gel slices, phosphopeptides were enriched using IMAC spin columns (Pierce, Rockford, Ill.) or TiO$_2$ Mono tip (GL Science, Japan). A nanoflow liquid chromatograph (Ultimate3000, LC Packings/Dionex, Sunnyvale, Calif.) coupled to an electrospray hybrid ion trap mass spectrometer (LTQ Orbitrap, Thermo, San Jose, Calif.) was used for tandem mass spectrometry peptide sequencing experiments. Peptides were separated with a C18 reverse phase column (LC Packings C18Pepmap) using a 40 min gradient from 5% B to 50% B (B: 90% acetonitrile/0.1% formic acid). The flow rate on the analytical column was 300 nl/min. Five tandem mass spectra were acquired for each MS scan using 60 sec exclusion for previously sampled peptide peaks (Spray voltage 2.3 kV, 30% normalized collision energy, scanning m/z 450-1,600). Sequences were assigned using Sequest (Thermo Fisher Scientific Inc., Waltham, Mass.) and Mascot (Matrix Science Ltd., Boston, Mass.) database searches against SwissProt protein entries of the appropriate species. Oxidized methionine, deamidation, carbamidomethyl cysteine, and phosphorylated serine, threonine and tyrosine were selected as variable modifications, and as many as 3 missed cleavages were allowed. The precursor mass tolerance was 1.08 Da and MS/MS mass tolerance was 0.8 Da. Assignments were manually verified by inspection of the tandem mass spectra and coalesced into Scaffold reports (Proteome Software, Inc., Portland, Oreg.).

Generation and purification of pTyr176-AKT phosphoantibody. Two AKT peptides coupled to immunogenic carrier proteins were synthesized.

The phosphopeptide: SEQ ID No. 16: Ac-ATGRY[pY]AMKIL-Ahx-C-amide The non-phospho peptide: SEQ ID No. 17: Ac-ATGRYYAMKIL-Ahx-C-amide Two rabbits were immunized twice with phosphopeptide, several weeks apart, and enzyme-linked immunosorbent assay was performed to determine the relative titer of sera against phosphorylated and nonphosphorylated peptides. The titer against phosphorylated peptides (1:40,000) was much greater than nonphosphorylated peptide (1:2700). The sera were affinity-purified. In brief, two antigen-affinity columns were used to purify the phospho-specific antibodies. The first column was the non-phosphopeptide affinity column. Antibodies recognizing the non-phospho residues of the peptide bound to the column and were eluted as pan-specific antibodies. The flow-through fraction was collected and then applied to the second column, the phospho-peptide column. Antibodies recognizing the phospho-residue bound to the column which was eluted as phospho-specific antibodies. The purified antibodies were extensively characterized for various applications e.g. Western blotting and immunohistochemistry.

Cell fractionation, immunoprecipitations and kinase assay. Membrane and cytosolic fractionation was performed using membrane fractionation kit (BioVision, Inc, CA). The nuclear/cytoplasmic fractionation was performed using protocol from Abcam (Abcam, Inc., Cambridge, Mass.). For immunoprecipitations, cells were lysed in receptor lysis buffer (RLB) containing 25 mmol/L Tris (pH 7.5), 500 mmol/L NaCl, 1% Triton X-100, 10% glycerol, phosphatase inhibitors (10 mmol/L NaF, 1 mmol/L Na$_2$VO$_4$), and protease inhibitor mix (Hoffmann-La Roche Inc., Switzerland). For co-immunoprecipitation, cells were lysed in buffer containing 25 mmol/L Tris (pH 7.5), 225 mmol/L NaCl, 1% Triton X-100, 10% glycerol, phosphatase inhibitors (10 mmol/L NaF, 1 mmol/L Na$_2$VO$_4$), and protease inhibitor mix (Hoffmann-La Roche Inc., Switzerland). The kinase assay was performed using kit from Calbiochem.

Purification, in vitro binding and phosphorylation assay. GST-Ack1 was purified using method described earlier (Mahajan N P, Earp H S (2003) An SH2 domain-dependent, phosphotyrosine-independent interaction between Vav1 and the Mer receptor tyrosine kinase: a mechanism for localizing guanine nucleotide-exchange factor action. J Biol Chem 278: 42596-42603). HEK293T cells were transfected with HA-tagged Ack1, AKT, Y176F mutant of AKT and FLAG-tagged AR; 48 hours post-transfection cell were lysed in RLB buffer. Lysates were incubated with HA beads (Sigma-Aldrich Co., St. Louis, Mo.) for 2 h, followed by washing with RLB buffer and elution in PBS containing HA or FLAG peptide (2 mM) on ice. Purity of preparation was confirmed by coomassie blue staining of gel. For the in vitro binding assay, 50 nM of purified Ack and AKT were incubated in modified RLB (mRLB) containing 25 mM Tris (pH 7.5), 175 mM NaCl, 1% Triton X-100, 10% glycerol, and protease inhibitor mix at room temperature. After 30 mins, anti-Ack1 antibodies and Protein-A-sepharose beads were added, incubated with shaking at 4° C. for overnight. Beads were washed thrice with mRLB buffer. Bound protein complex was dissociated from beads by boiling in SDS sample buffer and assessed by gel electrophoresis and detection by immunoblotting with anti-AKT antibody. In a control experiment, immunoprecipitation was done using non-specific IgG. For in vitro phosphorylation of AKT by Ack1, 50 nM of purified Ack1 and AKT were incubated in kinase buffer contained 20 mmol/L HEPES (pH 7.5), 150 mM NaCl, 10 mmol/L MgCl$_2$, 0.1 mmol/L Na$_2$VO$_4$, 0.5 mmol/L DTT, 0.25 mmol/L ATP for 1 hour at 30° C. The reaction was stopped by adding sample buffer and reaction was assessed by gel electrophoresis and detection by immunoblotting with antibodies as shown.

Quantitative RT-PCR. All RT reactions were done at the same time so that the same reactions could be used for all gene studies. For the construction of standard curves, serial dilutions of pooled sample RNA were used (50, 10, 2, 0.4, 0.08, and 0.016 ng) per reverse transcriptase reaction. One "no RNA" control and one "no Reverse Transcriptase" control were included for the standard curve. Three reactions were performed for each sample: 10 ng, 0.8 ng, and a NoRT (10 ng) control. Real-time quantitative PCR analyses were performed using the ABI PRISM 7900HT Sequence Detection System (Applied Biosystems/Life Technologies Corp., Carlsbad, Calif.). All standards, the no template control (H$_2$O), the No RNA control, the no Reverse Transcriptase control, and the no amplification control (Bluescript plasmid) were tested in six wells per gene (2 wells/plate×3 plates/gene). All samples were tested in triplicate wells each for the 10 ng and 0.8 ng concentrations. The no RT controls were tested in duplicate wells. PCR was carried out with SYBR Green PCR Master Mix (Applied Biosystems/Life Technologies Corp., Carlsbad, Calif.) using 2 µl of cDNA and the primers, seen in Table 1 in a 20-µl final reaction mixture: Actin: 300/300 nM; p21: 300/300 nM; p27Kip1-1:300/300 nM; p27Kip1-2: 300/300 nM; FASL-2: 300/300 nM; GADD45-1: 300/300 nM; GADD45-2: 300/300 nM; BIM: 100/100 nM; HPRT1: 100/100 nM. After 2-min incubation at 50° C., AmpliTaq Gold was activated by a 10-min incubation at 95° C., followed by 40 PCR cycles consisting of 15 s of denaturation at 95° C. and hybridization of primers for 1 min at 55° C. Dissociation curves were generated for each plate to verify the integrity of the primers. Data were analyzed using SDS software version 2.2.2 and exported into an Excel spreadsheet. The actin data were used for normalizing the gene values; i.e., ng gene/ng actin per well.

TABLE 1

Primer sequences for qRT-PCR.

| Seq ID No. | Primer Name | Primer Sequence |
|---|---|---|
| 18 | p27Kip1 Fwd | TCA AAC GTG AGA GTG TCT AAC G |
| 19 | p27Kip1 Rev | CCG GGC CGA AGA GAT TTC TG |
| 20 | p21 Fwd | TGT TCC GCA CAG GAG CAA |
| 21 | p21 Rev | TGA GCG CAT CGC AAT CA |
| 22 | Bim Fwd | CCC GGA GAT ACG GAT TGC AC |
| 23 | Bim Rev | GCC TCG CGG TAA TCA TTT GC |
| 24 | Gadd45 Fwd | AGA CCG AAA GGA TGG ACA CG |
| 25 | Gadd45 Rev | TGA CTC CGA GCC TTG CTG A |
| 26 | Hprt1 Fwd | CAC AGG ACT AGA ACA CCT GC |
| 27 | HPRT Rev | GCT GGT GAA AAG GAC CTC T |
| 28 | ACTB Fwd | GTG GGC ATG GGT CAG AAG |
| 29 | ACTB Rev | TCC ATC ACG ATG CCA GTG |

Fluorescence microscopy. For cellular localization studies, NIH3T3 cells grown on coverslips were transfected at 50% confluency. Cells were fixed with 4% paraformaldehyde in PBS for 10 min, washed with PBS. Coverslips with fixed cells were mounted on slides in Vectashield mounting medium with DAPI (Vector Laboratories), and red (dsRed2-N1AKT) or green (EGFP-346K) fluorescence was detected using a Zeiss Automated Upright Fluorescent Microscope and charge-coupled device (CCD) camera with appropriate filters. Zeiss Axiovision software was used for image viewing and processing.

Figure 1:
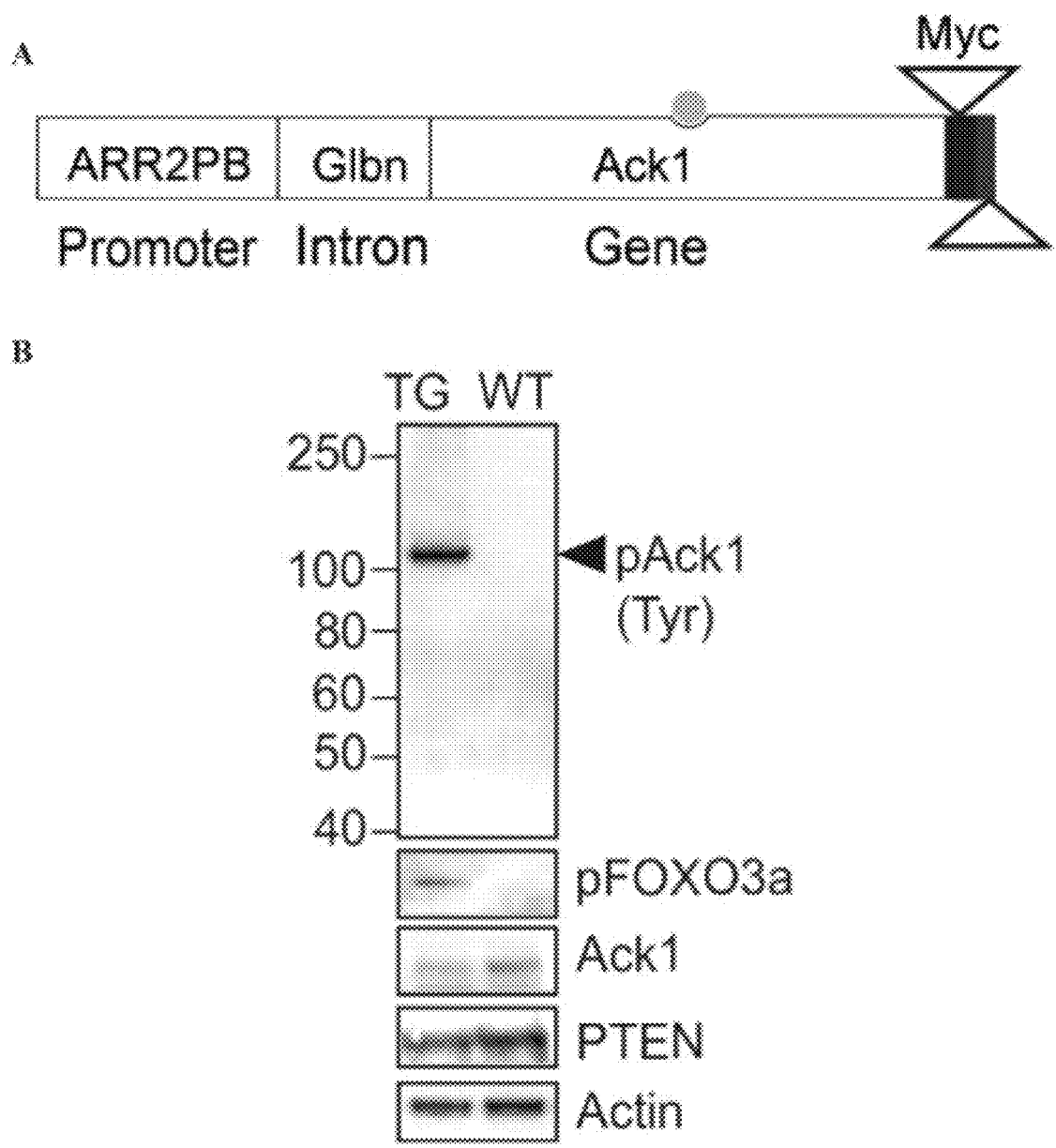
FIGS. 1(A) and (B) are a composite image of probasin-Ack1 transgenic mice displaying pTyr176-AKT and develop mPINs. (A) An illustration of the transgenic construct (Prob-Ack1). (B) A blot showing 25 wk old Probasin-Ack1 transgenic (TG) and wild type [21] male mice prostate lysates, subjected to immunoprecipitation (IP) using anti-Myc antibodies followed by immunoblotting (IB) with pTyr antibodies (top panel). For bottom panels, lysates were subjected to IB with indicated antibodies.

Ack1 Transgenic (TG) mice. For in vivo expression of Ack1, Myc-epitope-tagged construct was generated in two steps. First, PCR was performed using ARR2PB promoter region as the template, which was subcloned in pTG1 vector. In the second step, a PCR product was generated using activated Ack1 (L487F) mutant as the template and the reverse primer encoding a Myc-tag. The caAck PCR product (1 to 787 aa) was digested and was inserted into the pTG1 vector downstream of a sequence coding Globin intron and upstream of a SV40 polyA site, as schematically illustrated in FIG. 1(A). The construct was sequenced. The ARR2PB-Ack1 plasmid was digested with HindIII and BamHI and a 4 Kb linear DNA fragment was gel purified and microinjected into fertilized C57B6 mouse eggs, which were then surgically transplanted into a pseudo-pregnant female. Transgenic founders were screened by PCR using genomic DNA isolated from tail snips. The prostate specific expression was assessed by immunoprecipitation with Myc-antibodies followed by immunoblotting with pTyr-antibodies, seen in FIG. 1(B). TG and WT mice were sacrificed at various time points for removal of prostate followed by lysate preparation and immunoblotting, seen in FIG. 2. Prostates from transgenic mice were dissected using a dissection microscope, fixed in 10% buffered formalin and embedded in paraffin. Sections were stained with haematoxylin and eosin and stained slides were evaluated by pathologist.

Flow Cytometry Analysis. AKT1&2KO MEFs transfected with either the AKT WT or 176 mutant constructs were serum starved 24 h post-transfection. Cells were either untreated or treated with EGF for 15 minutes and harvested. Cells were singly or doubly stained with antibodies; AKT Ser473 conjugated to Alexa 647 and HA tag conjugated to Alexa 488 according to the manufacturer's protocol (Cell Signaling). Briefly, cells were resuspended in 1× Phosphate Buffered Saline (PBS) to which paraformaldehyde was added to a final concentration of 4%. Cells were fixed at 37° C. for 10 min and chilled on ice for 1 min. The fixative was removed after centrifugation at 1500 rpm for 5 min. Cells were resuspended in ice cold 100% methanol and incubated on ice for 30 min and stored at −20° C. in 90% methanol. One million cells from each sample were rinsed with 2 ml of 1×PBS containing 0.5% BSA by centrifugation and resuspended in 90 µl of incubation buffer per assay tube for 10 min. 10 µl of conjugated antibody was added to the assay tube and incubated for 60 min in the dark at room temperature. The cells were rinsed twice with the incubation buffer by centrifugation and resuspended in 0.5 ml PBS and acquired on FACS caliber and analyzed by the FlowJo software.

Tissue Microarray (TMA) analysis. For assessment of pTyr284-Ack1 and pTyr176-AKT expression in breast cancer, immunohistochemistry was carried out on two high-density TMAs (n=476 cores) containing samples of normal breast tissue, atypical ductal hyperplasia (ADH), ductal carcinoma in situ (DCIS), invasive ductal carcinoma (IDC), lymph node macro metastasis (LNMM). Four µm sections were cut with Leica microtome (Leica Microsystems Inc, Bannockburn, Ill.) and transferred to adhesive-coated slides. The tissue array slides (4 slides including 2 test duplicate slides, and positive and negative controls) were stained for pTyr284-Ack1 and pTyr176-AKT using respective rabbit polyclonal antibodies. The slides were dewaxed by heating at 55 Celsius for 30 min and by three washes, 5 min each, with xylene. Tissues were rehydrated by series of 5 min washes in 100%, 95%, and 80% ethanol and distilled water. Antigen retrieval was performed by heating the samples at 95° C. for 30 min in 10 mmol/L sodium citrate (pH 6.0). After blocking with universal blocking serum (DAKO Diagnostic, Mississauga, Ontario, Canada) for 30 min, the samples were then incubated with rabbit polyclonal pTyr284-Ack1 antibody (1:300 dilution; Milipore) and rabbit polyclonal phospho-AKT antibody (1:25 dilution) at 4° Celsius overnight. The sections were incubated with biotin-labeled secondary and streptavidin-peroxidase for 30 min each (DAKO Diagnostic). The samples were developed with 3,3'-diaminobenzidine substrate (Vector Laboratories, Burlington, Ontario, Canada) and counterstained with hematoxylin. Following standard procedures the slides were dehydrated and sealed with cover slips. Negative controls were included by omitting pTyr284-Ack1/pTyr176-AKT antibody during primary antibody incubation. The phospho-AKT/Ack1 antibodies were extensively validated for immunohistochemistry studies. MCF7 cells treated with heregulin and RWPE cells treated with EGF ligand (or no ligand) were fixed, paraffin imbedded, sectioned and used for antibody validation. Further, MEF1&2KO cells transfected with activated Ack1 and AKT were also used to validate antibodies. The pTyr284-Ack1 and pTyr176-AKT staining in paraffin embedded tissues were examined in a blinded fashion by two independent pathologists (A.L. and D.C.). If needed, a consensus score was reached for each specimen. The positive reactions were scored into four grades according to the intensity of staining: 0, 1+, 2+ and 3+. The percentages of pTyr176-AKT positive cells were also scored into four categories: 0 (0%), 1+(1-33), 2+(34-66), 3+ (more than 66%). The product of the intensity and percentage scores was used as a final staining score.

Statistical analysis. The Mantel-Haenszel $\chi^2$ test was performed to examine if there is an increasing trend for pTyr284-Ack1 and pTyr176-AKT with respect to different progression stages of breast or pancreatic cancer. The ordinal intensity levels of pTyr284-Ack1 and pTyr176-AKT 0, 1, 2, 3, 4, 6, 9 were pooled into 6 levels (as 0, 1, 2, 3, 4, and 6 and above) to accommodate the rare observations in the highest intensity level in most stages. Analysis of variance was performed to examine whether the expression levels of pTyr284-Ack1 and pTyr176-AKT differ among different tumor stages. Boxplots were used to summarize the intensity distribution at each progression stage. Furthermore, Tukey-Kramer method was performed to examine between which pairs of stages the expression levels are different. This post-hoc procedure adjusts for all pairwise comparisons and simultaneous inference. When more than one sample was obtained from a patient, the intensity of the most progressed stage was used for the analysis. Correlation between pTyr284-Ack1 and pTyr176-AKT was explored using Spearman ranked correlation analysis. The association of the expression levels of pTyr284-Ack1 and pTyr176-AKT and the overall survival of patients were assessed using the Kaplan-Meier method. For breast cancer data, there were 144 individuals with available pTyr284-Ack1 staining and survival information while there were 140 individuals with available pTyr176-AKT staining and survival information. For pancreatic cancer data, there were 83 individuals with available pTyr284-Ack1 staining and survival information while there were 76 individuals with available pTyr176-AKT staining and survival information. Statistical differences between the groups were determined using log-rank test.

Ack1 phosphorylates AKT at evolutionary conserved Tyr176 resulting in AKT activation.

Figure 3:
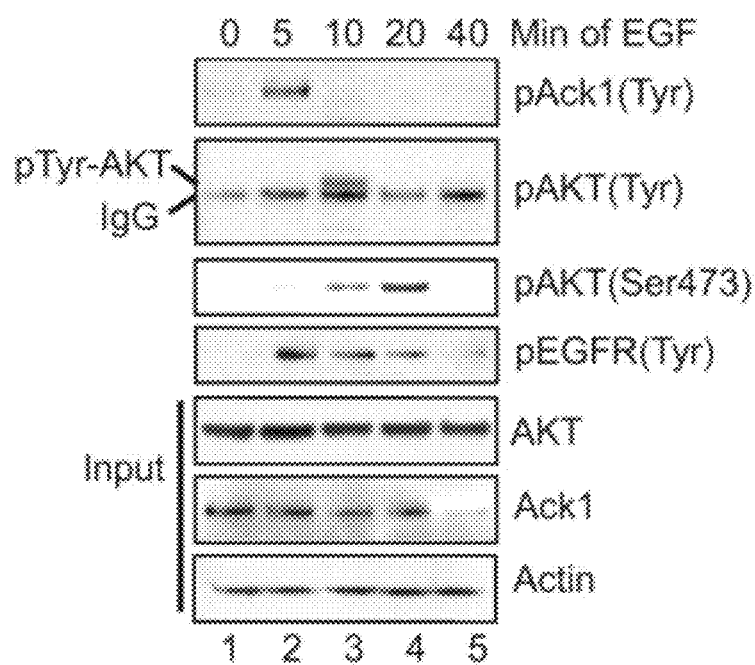
FIG. 3 is a blot which indicates that Tyr176 phosphorylation precedes AKT activation. MEF2KO cells were serum starved (24 h) and treated with EGF (10 ng/ml). The lysates were immunoprecipitated (IP) with anti-Ack1 (top panel), anti-AKT (second panel) and anti-EGFR (fourth panel) antibodies followed by immunoblotting (IB) with anti-pTyr antibodies. The remaining panel represents IB with antibodies as indicated.
Figure 4:
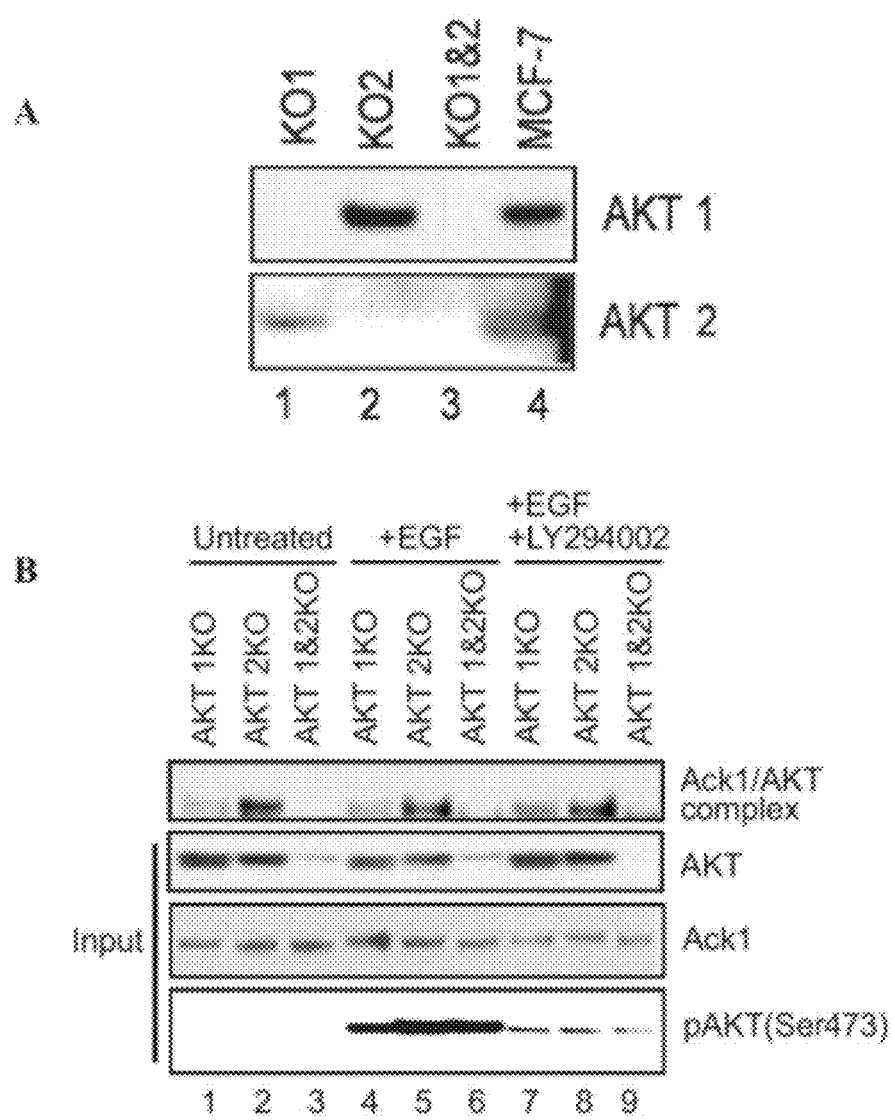
FIGS. 4(A) and (B) are blots showing AKT is Tyr-phosphorylated by Ack1 in vitro. (A) AKT MEF KO1, KO2 and KO1&2's lack respective AKT isoforms. Equal amounts of MEFs protein lysates were subjected to IB as indicated. MCF-7 cell lysate was used as control. (B) MEFs were serum starved (24 h) and treated with EGF (10 ng/ml for 10 mins) or pretreated with LY294002 (10 µM for 1 h) and EGF. The lysates were IP with Ack1 antibodies followed by IB with pan-AKT antibodies (top panel).

EGF signaling cascades have been linked to cancer, with overexpression of the EGFR cellular receptor identified as a transforming event. (Salomon D S, Brandt R, Ciardiello F, Normanno N. (1995). Epidermal growth factor-related peptides and their receptors in human malignancies. *Crit Rev Oncol Hematol* 19: 183-232; Grandis J R, Sok J C. (2004). Signaling through the epidermal growth factor receptor during the development of malignancy. *Pharmacol Ther* 102: 37-46; Merrick D, Kittelson J, Wintherhalder R, Kotantoulos G, Ingeberg S, Keith R L et al. (2006). Analysis of c-ErbB 1/epidermal growth factor receptor and c-ErbB2/HER-2 expression in bronchial dysplasia: evaluation of potential targets for chemoprevention of lung cancer. *Clin Cancer Res* 12(7 Pt 1): 2281-2288). EGF treatment of mouse embryonic fibroblasts (MEFs) was seen to result in rapid Tyr-phosphorylation of Ack1 as well as Akt1 at 5 and 10 mins respectively, suggesting that these two Tyr-phosphorylation events could be linked, seen in FIG. 3. To test this hypothesis, Ack1 was examined to determine whether Ack1 could bind Tyr-phosphorylate AKT following RTK activation. Co-immunoprecipitation of lysates derived from Akt1, Akt2, and Akt1 & 2 knockout mouse embryo fibroblasts (MEF1KO, MEF2KO, and MEF1&2KO, respectively, seen in FIG. 4(A) that were treated with EGF, either with or without pretreatment with LY294002, a PI3K inhibitor, revealed that endogenous Akt1 (hereinafter, AKT) and Ack1 formed a stable complex which was not abrogated by LY294002, as seen in FIG. 4(B). The bottom panel shows that upon LY294002 addition there was substantial decrease in AKT Ser473-phosphorylation, suggesting that LY294002 is functional. Akt2 interacted weakly with Ack1, while Akt3 present at low levels in the MEF1&2KO cells was not detectable in the complex.

Figure 5:
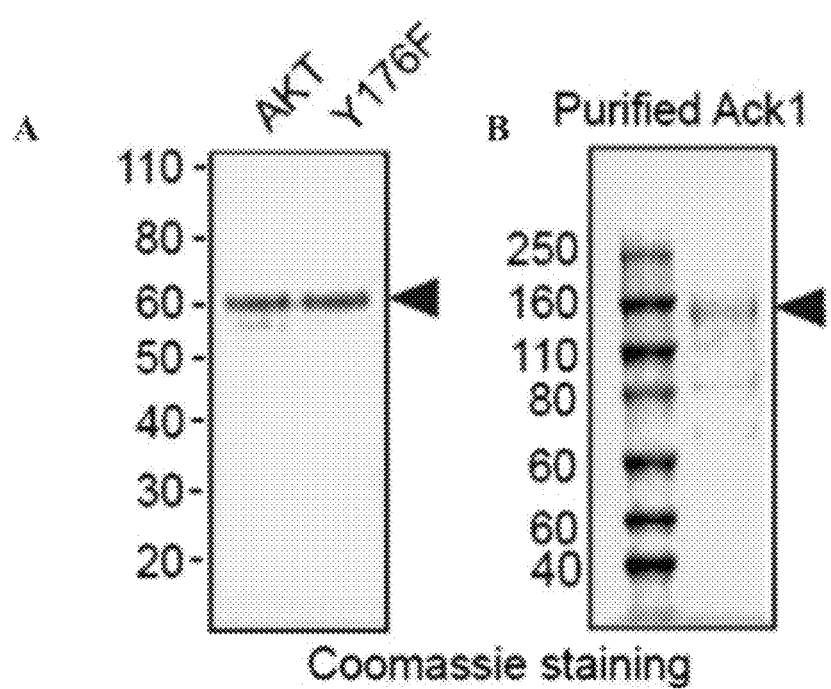
FIGS. 5(A) and (B) are blots showing Purification of Ack1 and AKT. (A) HA-tagged Ack1 and AKT were expressed in HEK293T cells, lysed and incubated with HA-beads. (B) Followed by extensive washing, proteins were eluted using HA-peptide (2 nM, 1 hr) and assessed by SDS-PAGE and Coomassie Brillant Blue-R250 (BioRad) staining.
Figure 6:
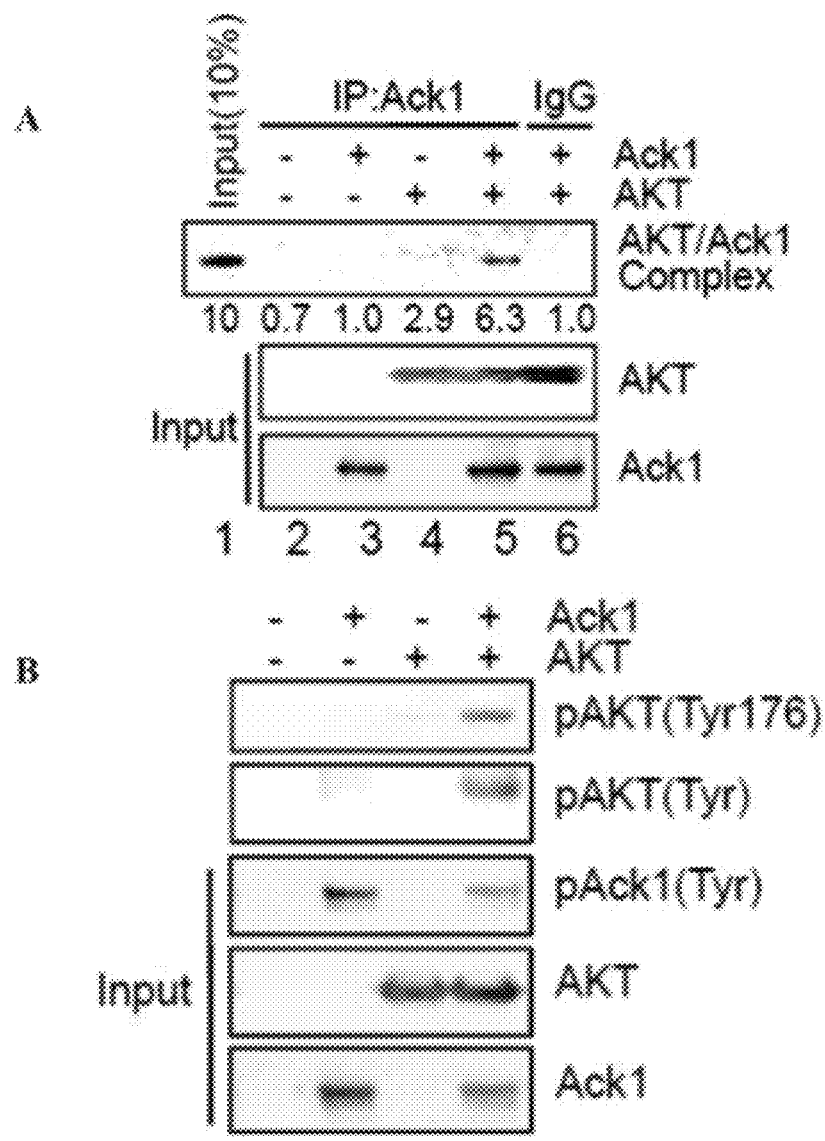
FIGS. 6(A) and (B) are blots showing AKT is Tyr-phosphorylated by Ack1 in vitro. (A) An in vitro binding assay. Equimolar amounts of purified Ack1 and AKT proteins were incubated for 30 min, and the complex was IP with Ack1 (lanes 2-5) or IgG (lane #6) antibodies followed by IB with anti-AKT antibodies (top panel). About 6.35% of total AKT was in complex with Ack1. (B) In vitro phosphorylation of purified AKT by Ack1. Equimolar amounts of purified Ack1 and AKT proteins were incubated in kinase buffer for 1 hr at 37 C. and the reaction mix was subjected to IB with pTyr176-AKT (top panel), pTyr ($2^{nd}$ and $3^{rd}$ panels), AKT ($4^{th}$ panel) and Ack1 (bottom panel) antibodies.
Figure 7:
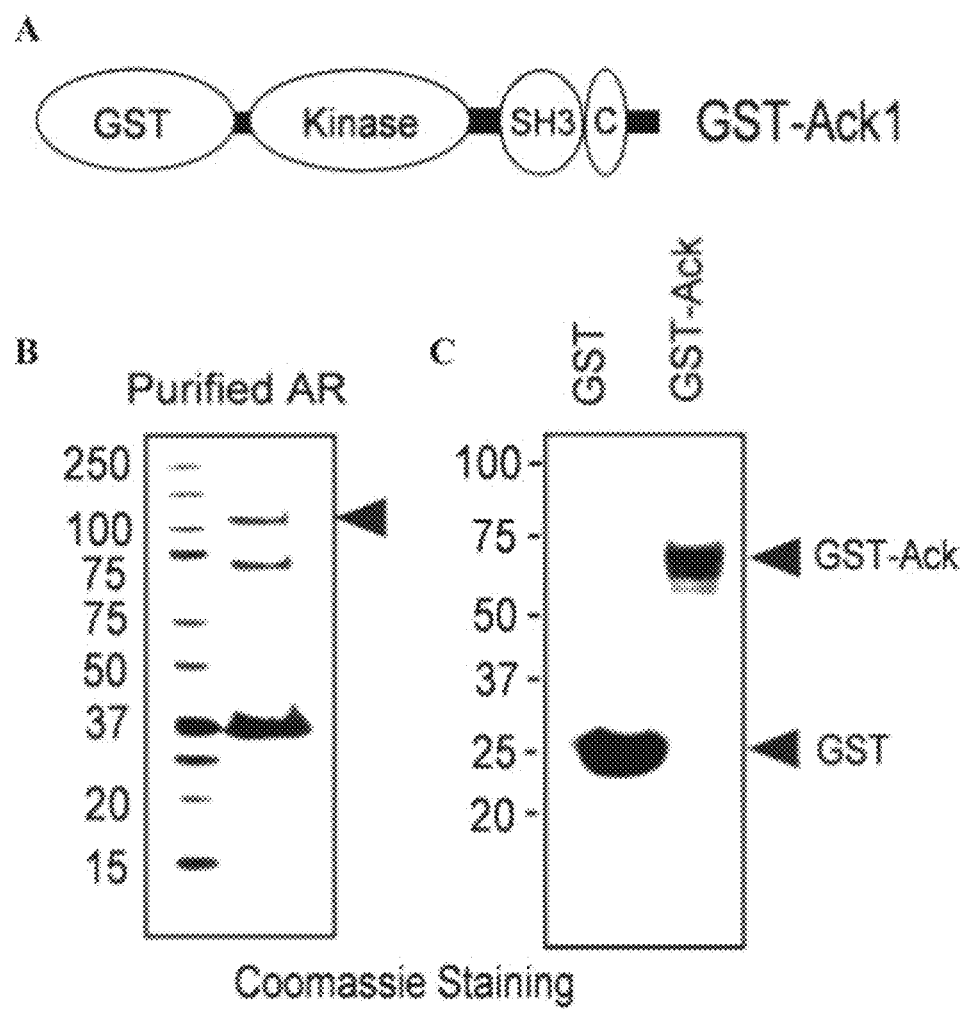
FIGS. 7(A) through (C) are a composite image of AKT is Tyr-phosphorylated by Ack1 in vitro. (A) A schematic representation of the GST-Ack1 construct. FLAG-tagged AR expressed in HEK293 cells and GST-tagged Ack1 was expressed in DH5alpha cells. Purified (B) FLAG-AR and (C) GST-Ack1 were assessed by SDS-PAGE followed by Coomassie staining.
Figure 8:
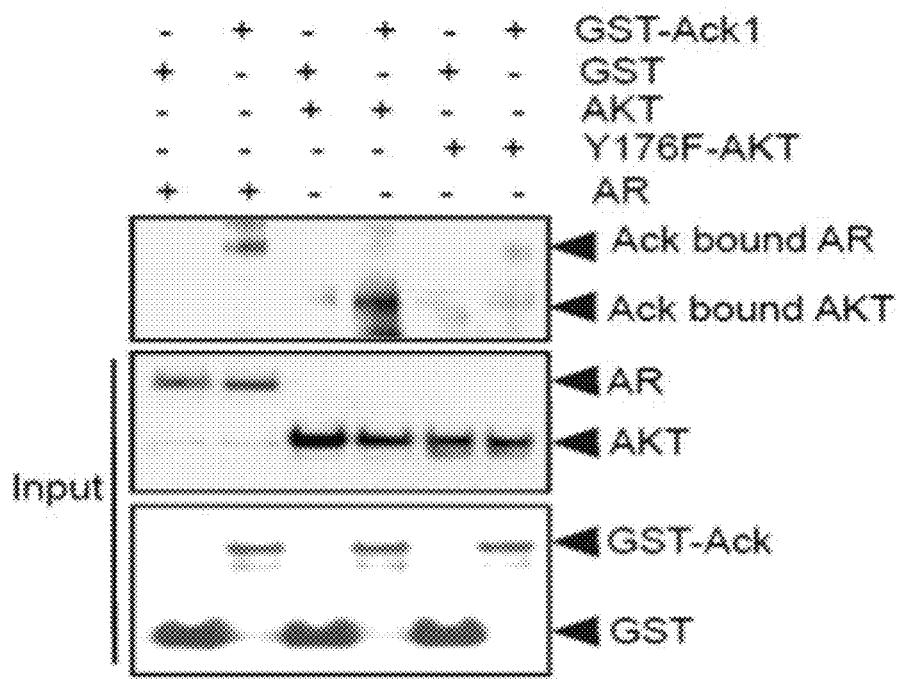
FIG. 8 is a blot showing AKT is Tyr-phosphorylated by Ack1 in vitro. (A) In vitro binding assay. Equimolar amounts of purified HA-AKT or FLAG-AR proteins were incubated with GST-Ack1 bound to beads for overnight, and the beads were washed followed by IB with anti-FLAG/HA antibodies (top panel). Lower panels show IB with FLAG/HA ($2^{nd}$ panel) and GST (bottom panel) antibodies.

To test whether Ack1 directly phosphorylates AKT, in vitro binding assay was performed and AKT Tyr-phosphorylation was assessed. Myc-tagged Ack1 and HA-tagged AKT constructs were expressed and purified using respective antibody beads followed by elution, as described in methods section. See FIGS. 5(A) and (B). In vitro binding assay revealed that purified Ack1 interacted directly with AKT resulting in AKT Tyr176-phosphorylation, as seen in FIGS. 5(A) and (B); 6(A) and (B). Further, a GST-Ack construct was generated that harbors kinase, SH3 and CRIB domain, schematically shown in FIG. 7(A), and expressed it in *E. coli*, as seen in FIGS. 7(B) and (C) (Mahajan N P, et al. (2005) Activated tyrosine kinase Ack1 promotes prostate tumorigenesis: role of Ack1 in polyubiquitination of tumor suppressor Wwox. Cancer Res 65: 10514-10523; Mahajan N P, Earp H S (2003) An SH2 domain-dependent, phosphotyrosine-independent interaction between Vav1 and the Mer receptor tyrosine kinase: a mechanism for localizing guanine nucleotide-exchange factor action. J Biol Chem 278: 42596-42603). Androgen-receptor (AR), another Ack1 substrate (Mahajan N P, et al. (2007) Activated Cdc42-associated kinase Ack1 promotes prostate cancer progression via androgen receptor tyrosine phosphorylation. Proc Natl Acad Sci USA 104: 8438-8443) was expressed as FLAG-tagged construct in HEK293 cells and purified using FLAG-beads, seen in FIG. 7(B). GST-tagged Ack1 or GST (as control) bound to glutathione beads were incubated with purified AKT or Y176F mutant of AKT or AR, as seen in FIGS. 5(A) and 7(C). GST-Ack1 bound to purified AKT and AR but not the Y176F mutant of AKT suggesting that AKT and AR are direct binding partners of Ack1, seen in FIG. 8.

Figure 9:
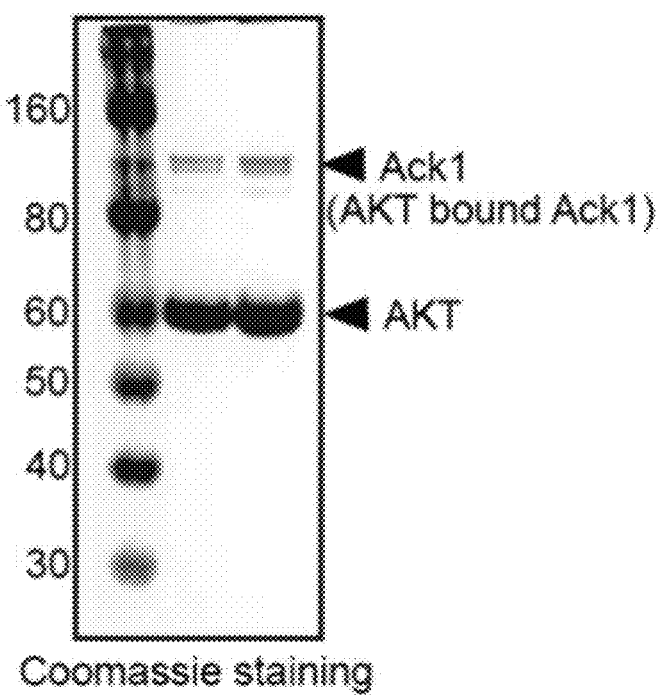
FIG. 9 is a blot showing Tyr176-phosphorylated AKT sample also contains Thr308 and Ser473 phosphorylated AKT. Activated Ack1 (caAck) and HA-tagged AKT were coexpressed in HEK293T cells followed by IP with HA-beads. IP AKT was subjected to SDS-PAGE electrophoresis and the gel was stained Coomassie. A prominent band of ~59 kDa corresponding to AKT is seen which was excised and subjected to mass spectrometry as described in methods section. The upper ~113 kDa band corresponds to caAck1 that bound to AKT.
Figure 10:
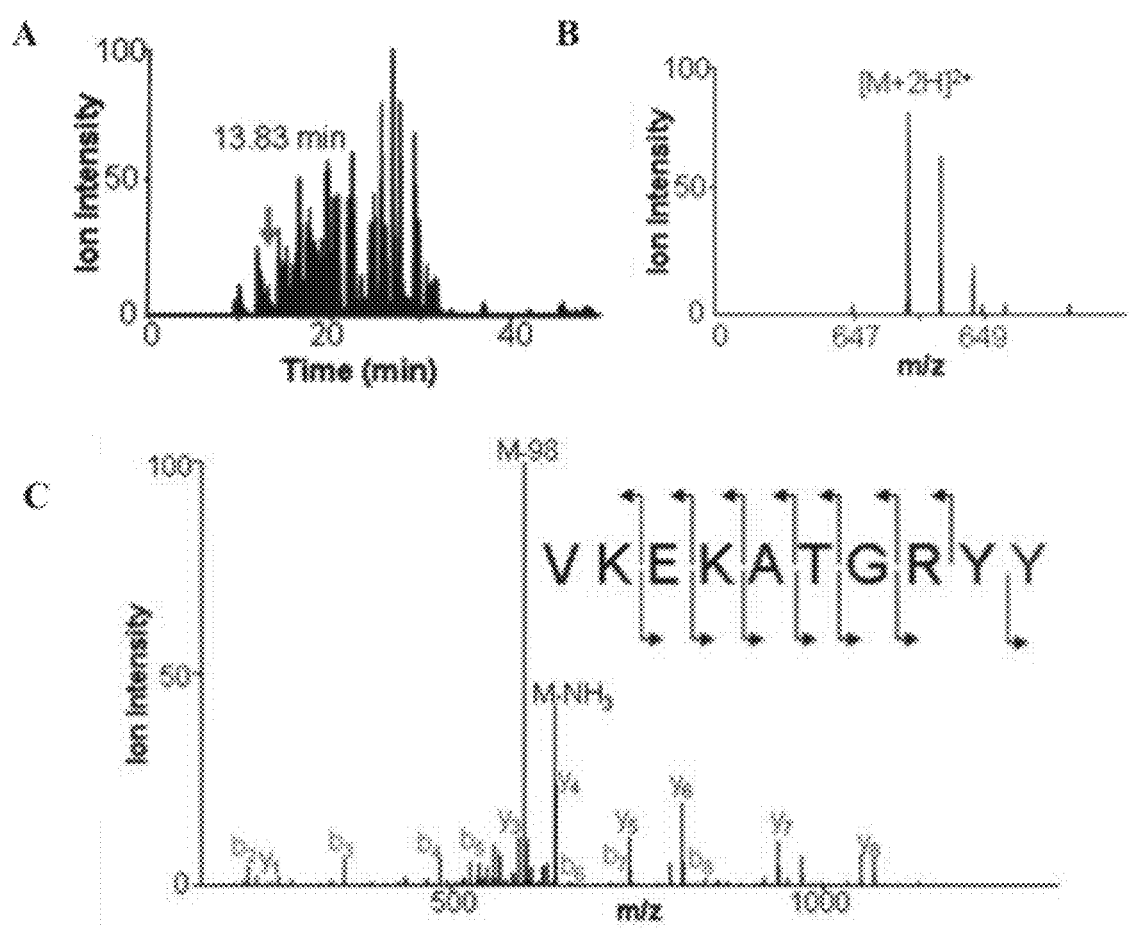
FIGS. 10(A) through (C) are graphs showing identification of Tyr176 phosphorylation event in AKT. (A) HA-tagged Tyr-phosphorylated AKT was purified (see FIG. 9) followed by trypsin chymotrypsin digestion. (B) The peptide was detected at 13.83 mins in the total ion chromatogram with mass-to-charge ratio 647.8132, which represents an error of 0.38 ppm. (C) The tandem mass spectrum matched the sequence, VKEKATGRYPY indicating that the C-terminal tyrosine was phosphorylated; the detection of the phosphotyrosine $y_1$ is consistent with this localization.
Figure 12:
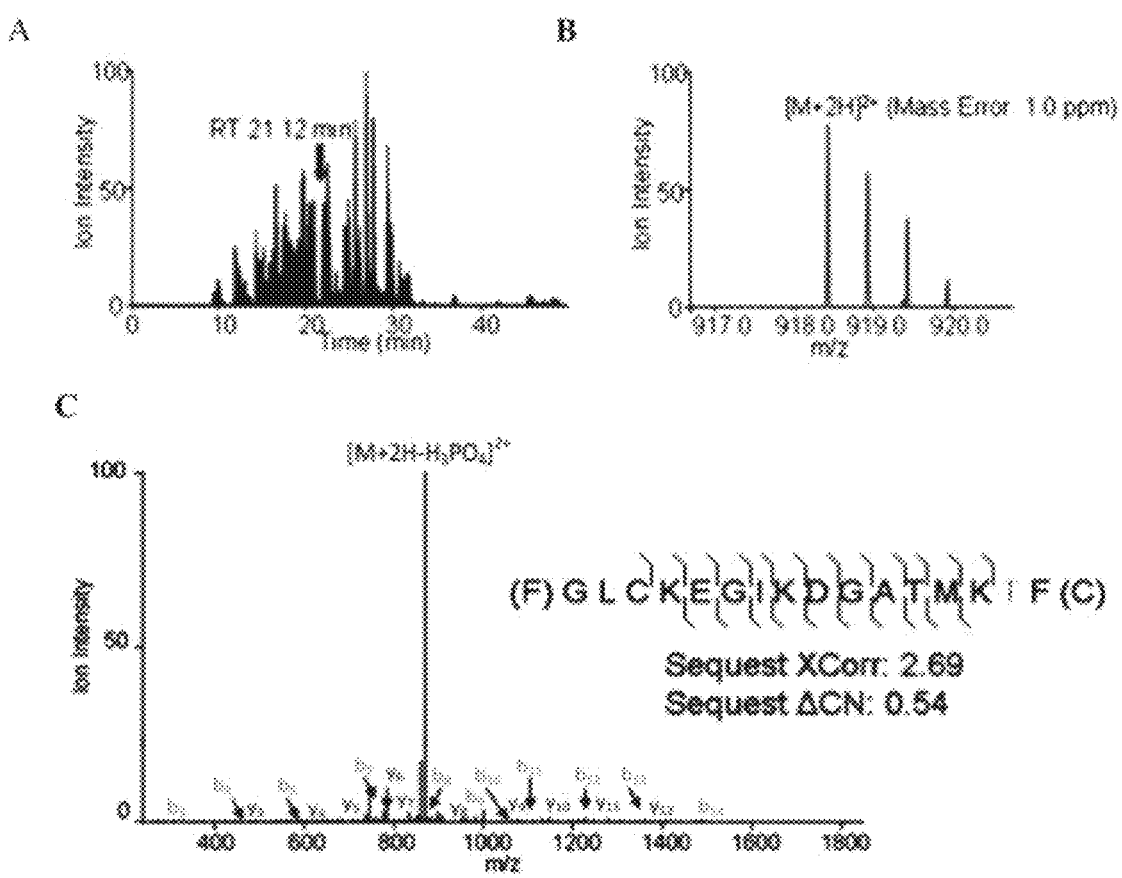
FIGS. 12(A) through (C) are graphs showing Tyr176-phosphorylated AKT sample also contains Thr308 phosphorylated AKT. Purified AKT peptide preparation that lead to the identification of pTyr176-AKT was assessed for other phosphorylation events. (A) A peptide was detected at 21.12 mins in the total ion chromatogram (B) with mass-to-charge ratio 918.43, which represents an error of 1.0 ppm. (C) The tandem mass spectrum matched the sequence, FGLCKEGIKD-GATMKpTFC indicating that Thr308 in AKT was phosphorylated; the detection of the phosphothreonine y3 is consistent with this localization.
Figure 13:
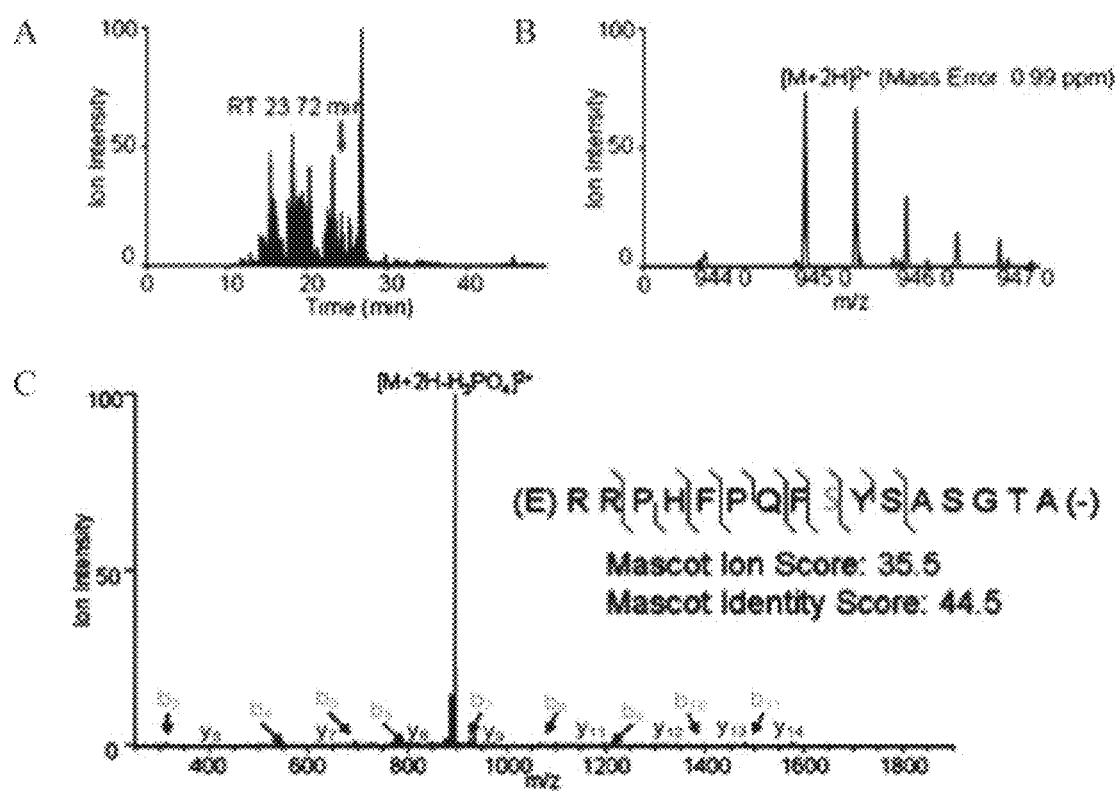
FIGS. 13(A) through (C) are graphs showing Tyr176-phosphorylated AKT sample also contains Ser473 phosphorylated AKT. Purified AKT peptide preparation that lead to the identification of pTyr176-AKT was assessed for other phosphorylation events. (A) A peptide was detected at 23.72 mins in the total ion chromatogram (B) with mass-to-charge ratio 944.93, which represents an error of 0.99 ppm. (C) The tandem mass spectrum matched the sequence, ERRPHFPQF pSYSASGTA indicating that Ser473 in AKT was phosphorylated; the detection of b8, b9, y7 and y8 is consistent with this localization.
Figure 14:
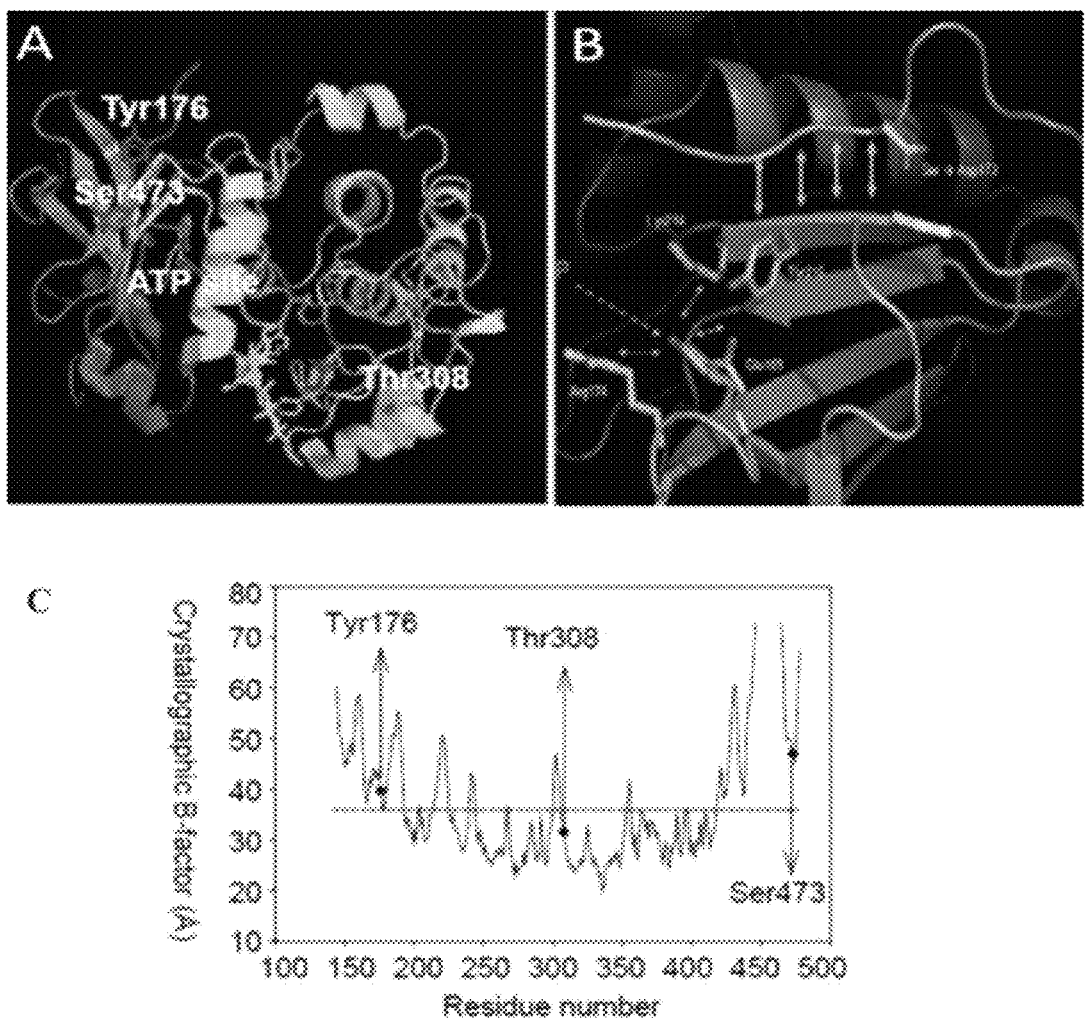
FIGS. 14(A) through (C) are a composite image showing AKT Tyr176-phosphorylation affects the loop harboring Ser473. (A) An illustration showing the residues Tyr176 and Ser473 are located in regions with increased conformational flexibility. The backbone of AKT1 is color-traced according to crystallographic B-factors from blue (20 Å, less flexible) to red (76 Å, highly flexible). (B) B-factor plot of all C-alpha atoms. The average main chain B-factor is 36 Å (dashed horizontal line). (C) AKT Tyr176-phosphorylation induces substantial conformational changes of residues in its vicinity. Electrostatic interactions could be established with Arg174 and/or Lys214 while electrostatic repulsion and/or steric hindrance (due to the bulky phosphate group) may affect Glu169 and Tyr215. This could lead to a shift of the β-strand flanking the c-terminal portion of the loop harboring Ser473, in turn causing structural alterations of this residue.
Figure 16:
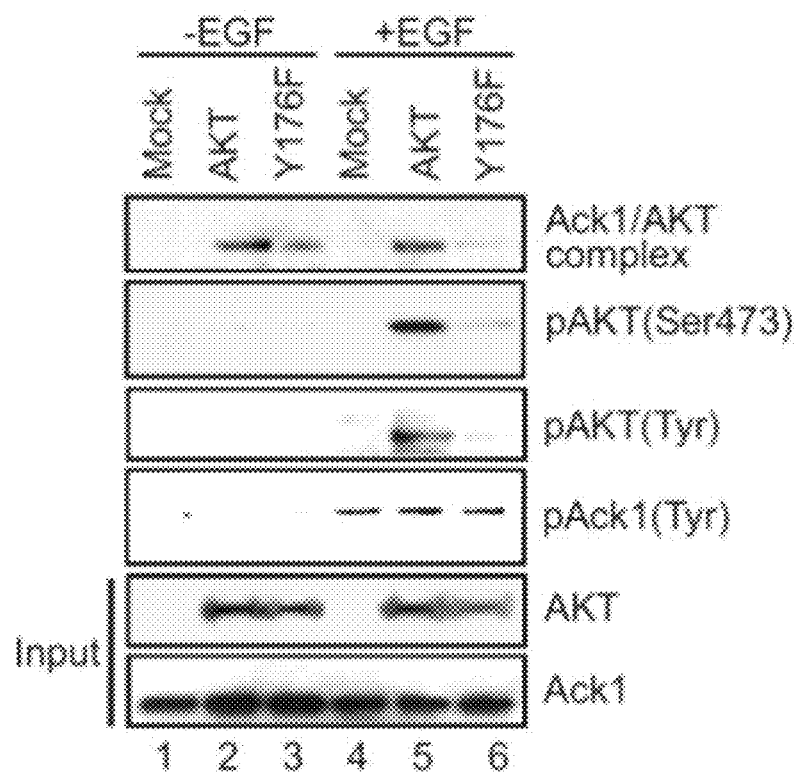
FIG. 16 exhibit a series of immunoblotting experiments showing Tyr176 phosphorylation precedes AKT activation. MEF1 &2KO cells expressing HA-tagged AKT or Y176F mutant were serum-starved (24 h), treated with EGF for 15 mins and lysates were IP with anti-Ack1 Abs followed by IB with anti-AKT antibodies (top panel). The lysates were also IP with anti-Ack1 antibodies followed by IB with pTyr antibodies (panel 4). The same blot was stripped and IB with anti-Ack1 antibodies (Bottom panel). These lysates were also subjected to IP with anti-HA antibodies followed by IB with Ser473, pTyr and AKT antibodies (panels 2, 3 and 5, respectively).
Figure 17:
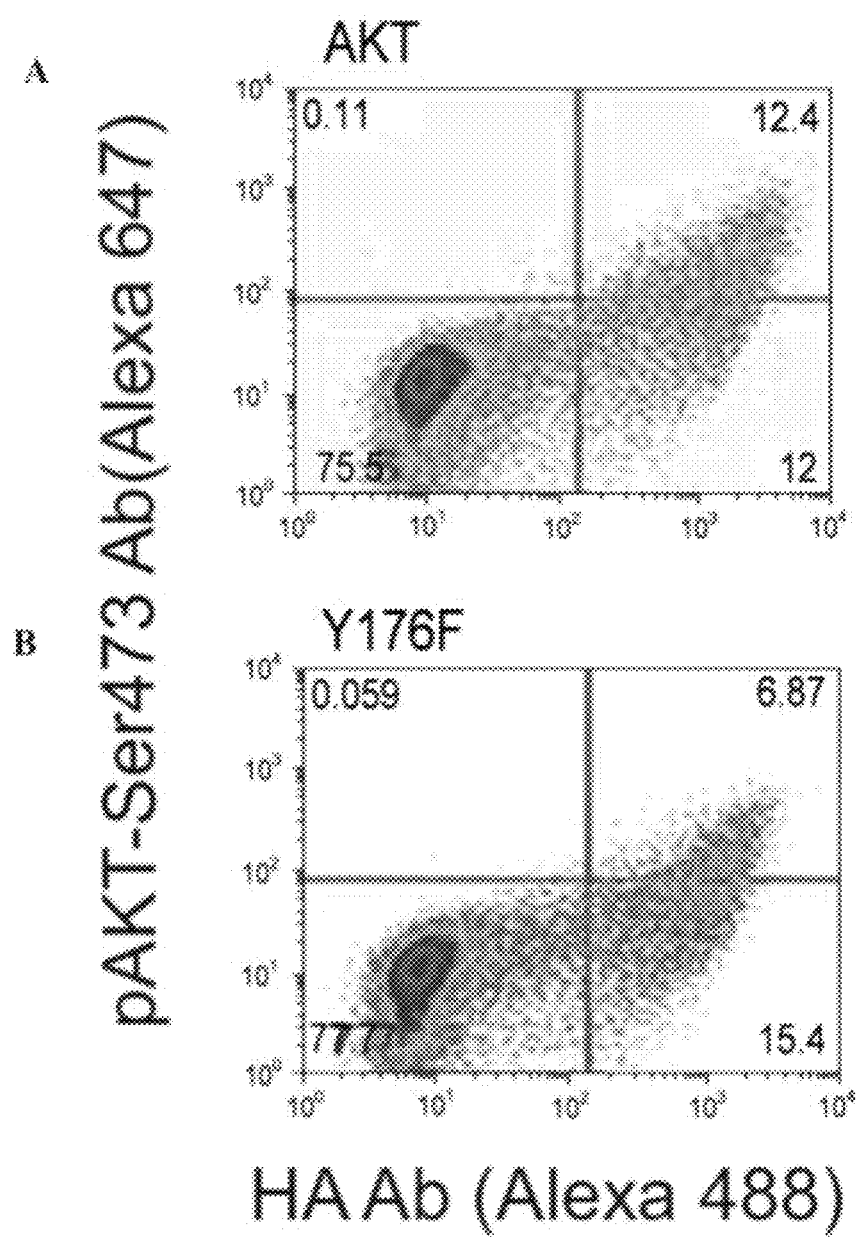
FIGS. 17(A) and (B) are flow cytometry profiles of (A) AKT and (B) Y176F mutant expressing MEF1&2KO cells. Cells were serum starved for 24 h, treated with EGF for 15 mins, fixed and stained with HA-antibodies conjugated to Alexa488 and phosphoSer473-antibodies conjugated to Alexa 647. Upper right quadrant represents cells which express HA-tagged AKT or Y176F mutant that are also Ser473-phosphorylated.
Figure 18:
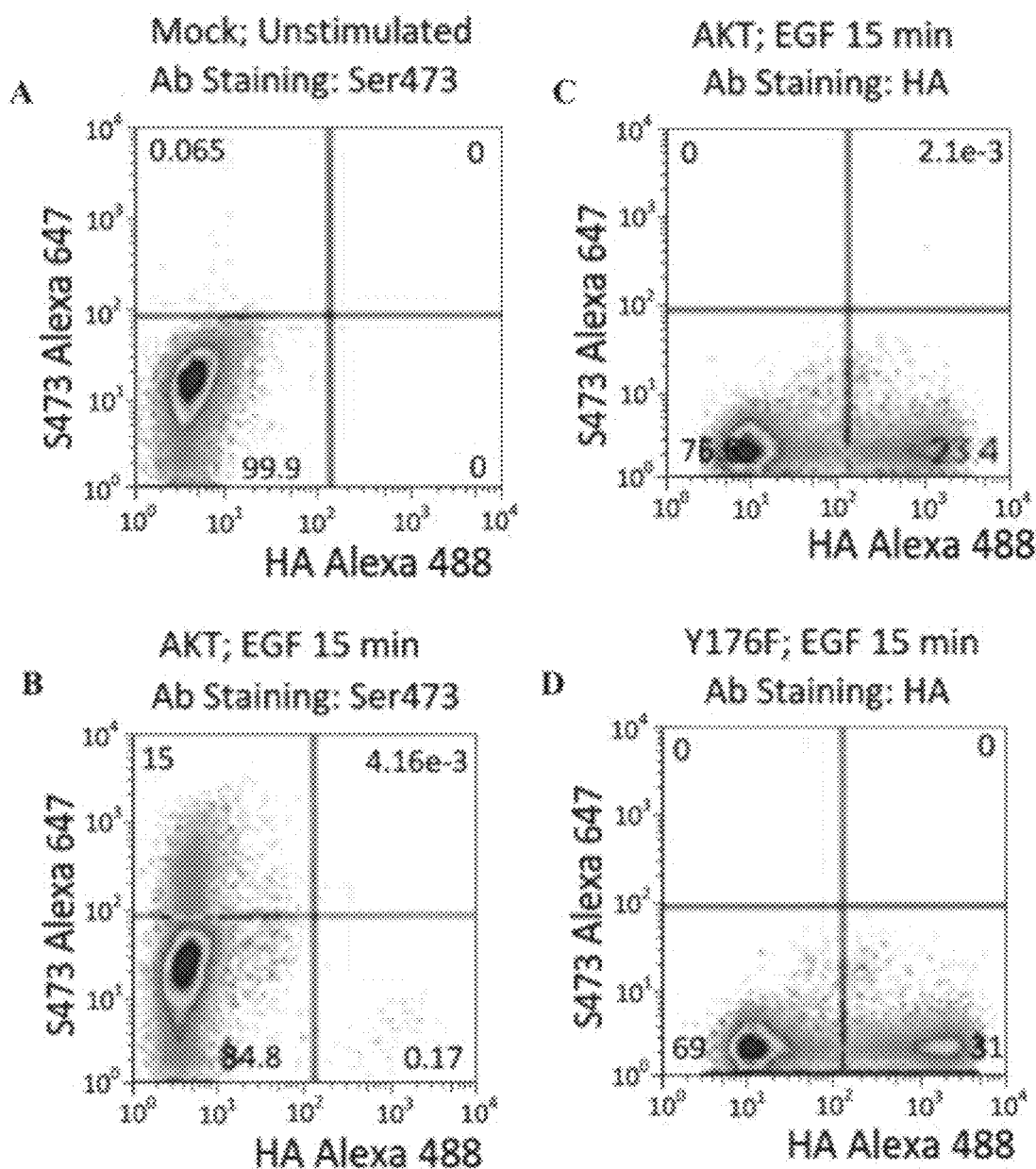
FIGS. 18(A) through (D) are flow cytometry profiles of AKT 1&2KOMEFs, expressing HA-AKT and/or HA-Y176F. (A) Is a graph indicating mock transfected cells stained with AKT-Ser473 antibody conjugated to Alexa 647 (untreated: 0.1%). (B) A graph showing the percentage of cells with AKT Ser473-phosphorylation upon EGF stimulation (15.2%). (C) Is a graph showing the percentage of cells expressing HA-AKT (23%) in cells stained with anti-HA antibody conjugated to Alexa 488. (D) A graph showing the percentage of cells expressing HA-Y176F (31%) in cells stained with anti-HA antibody conjugated to Alexa 488.

Affinity purification of AKT coexpressed with Ack1, seen in FIG. 9, followed by mass spectrometry analysis revealed that AKT was phosphorylated at Tyrosine 176, as seen in FIGS. 10(A) through (C). Tyr176, located in the kinase domain, is evolutionarily conserved from unicellular eukaryotes to mammals and within all the three AKT isoforms, seen in FIG. 11. Two other phosphorylation events, Ser473 and Thr308 were also identified in the same preparation, seen in FIGS. 12(A) through 13(C). Computational analysis revealed that Tyr176 and Ser473 are located in regions with increased conformational flexibility and phosphorylation at Tyr176 is likely to induce substantial conformational change and thus affect the loop harboring Ser473, seen in FIGS. 14(A) through (C). To determine whether AKT Tyr176-phosphorylation is an upstream event that regulates AKT activation (or Ser473 phosphorylation, hereafter), site directed mutagenesis was performed to generate AKT phospho-tyrosine (Y176F) mutant, seen in FIG. 15. The Y176F mutant interacted poorly with Ack1 in the absence of ligand, and in the presence of ligand failed to interact with Ack1 resulting in decreased AKT Tyr/Ser-phosphorylations, seen in FIG. 16, lane 6). Flow cytometric analysis of EGF treated cells revealed significant reduction in Ser473-phosphorylation in MEF1&2KO cells expressing Y176F as compared to AKT, as seen in FIGS. 17(A) and (B); 18(A) through (D). These results imply that Ack1 mediated AKT Tyr-phosphorylation results in subsequent AKT activation.

Ack1/AKT interacting domains.

Figure 15:
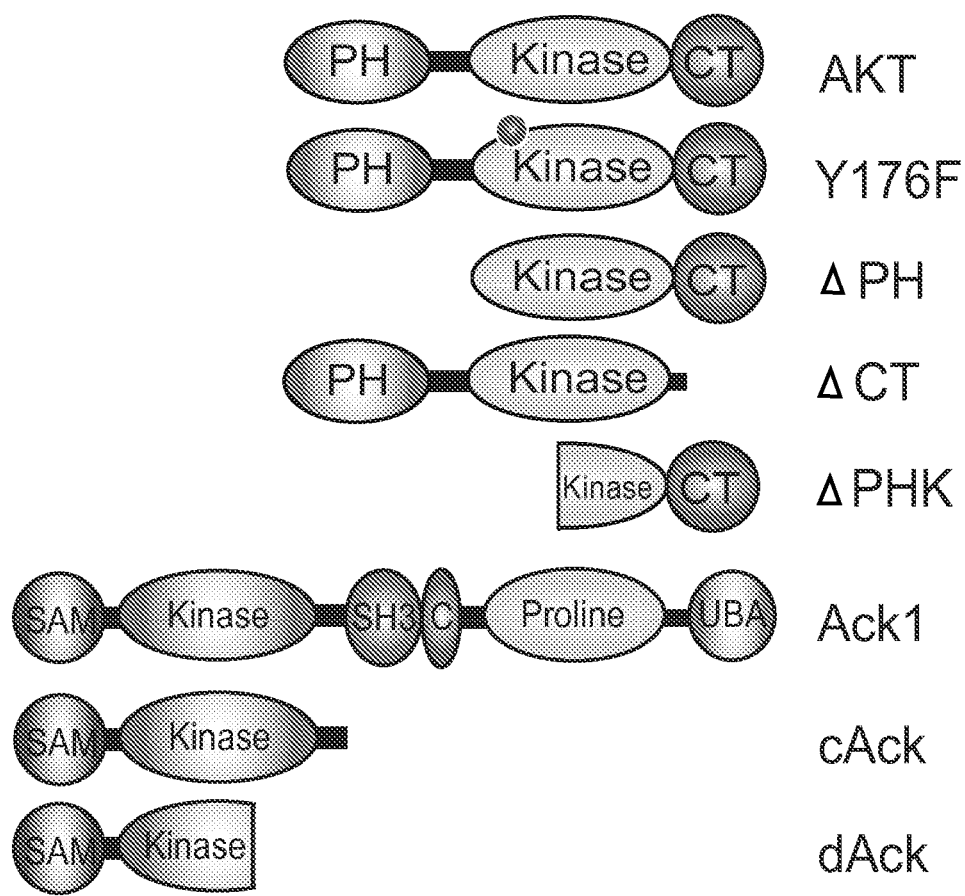
FIG. 15 is a schematic representation of wild type AKT, Y176F point mutant and deletion constructs. Site-directed mutagenesis of AKT was performed to generate the tyrosine to phenylalanine, Y176F, point mutant. PH, Pleckstrin homology domain; Kinase, Kinase domain and CT, Carboxy Terminal regulatory region. Schematic representation of Ack1 and deletion constructs. SAM, Sterile alpha motif; Kinase, kinase domain; SH3, Src homology domain 3; C, Cdc42 Rac interactive binding domain.
Figure 19:
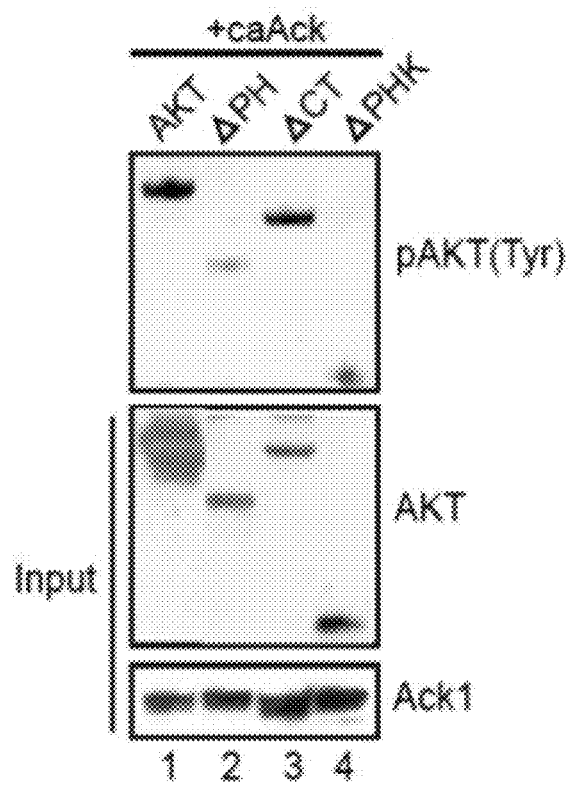
FIG. 19 is a blot showing the kinase domain of Ack1 interacts with AKT PH domain/Tyr176 in kinase domain. MEF1&2KO cells were co-transfected with HA-tagged AKT deletions and caAck1. The lysates were IP using HA antibodies followed by IB with pTyr antibodies (top panel). Lower panel show IP using HA antibodies followed by IB with AKT antibodies. Bottom panel show IB of the lysate with Ack1 antibodies.
Figure 20:
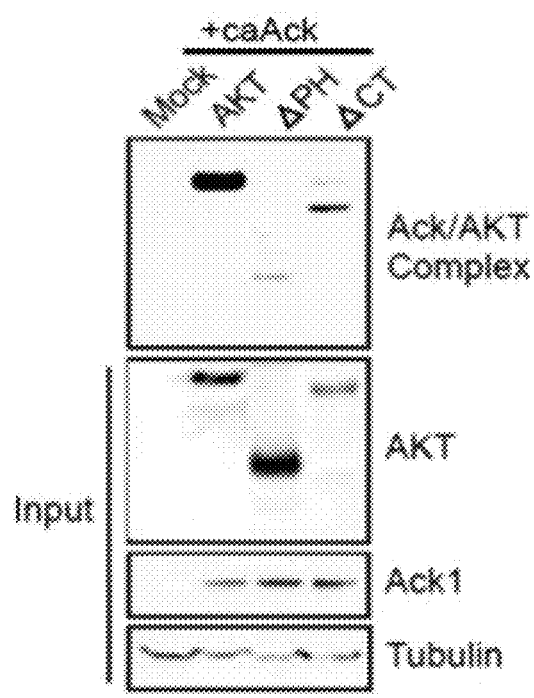
FIG. 20 is a blot showing the kinase domain of Ack1 interacts with AKT PH domain/Tyr176 in the kinase domain. HEK293 cells were co-transfected with HA-tagged AKT deletions and myc-tagged caAck. The lysates were IP using Myc antibodies followed by IB with HA antibodies (top panel). Lower panels are as described above.

To identify domains involved in Ack1-AKT interaction, various deletions of Ack1 and AKT were generated, seen in FIG. 15. MEF1&2KO cells were co-transfected with HA-tagged AKT deletions and activated Ack1 or caAck. Immunoprecipitation using HA antibodies followed by immunoblotting with pTyr antibodies revealed Tyr-phosphorylation of full-length AKT and AKT lacking carboxy terminus (ΔCT-AKT), however, AKT deletion construct lacking the PH domain (ΔPH-AKT) exhibited significant decrease in Tyr-phosphorylation, seen in FIG. 19, top panel. The decreased phosphorylation of AKT deletion construct lacking PH domain could be due to poor binding with activated Ack1. To assess this interaction in further detail, a co-immunoprecipitation experiment was performed. It revealed that in contrast to AKT or ΔCT-AKT, ΔPH-AKT weakly binds Ack1, seen in FIG. 20, top panel. Tyr176 residue in AKT kinase domain has been demonstrated necessary for Ack1/AKT interaction, thus, collectively it indicates that Ack1 needs both the PH domain and tyrosine176 in AKT kinase domain for complex formation.

Figure 21:
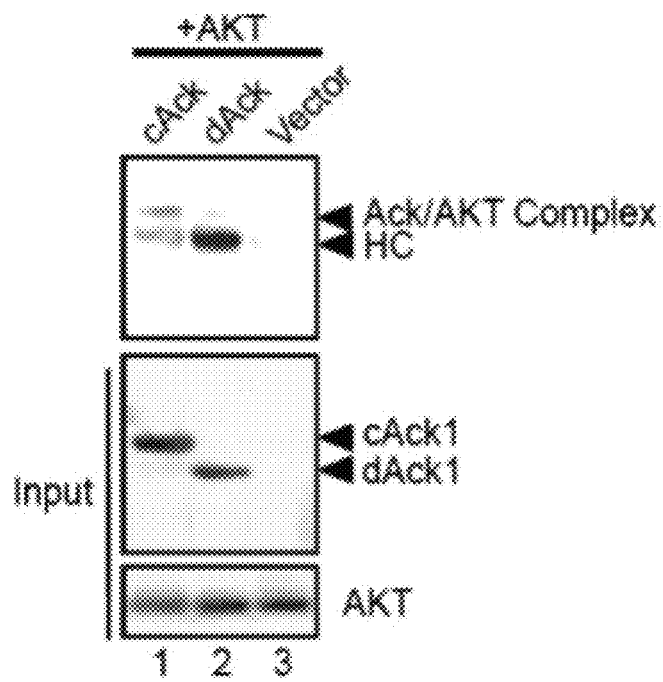
FIG. 21 is a blot showing the kinase domain of Ack1 interacts with AKT PH domain/Tyr176 in kinase domain. MEF1&2KO cells were transfected with myc-tagged Ack1 deletions and HA-tagged AKT. The lysates were IP using Myc antibodies followed by IB with AKT antibodies (top panel). Lower panels show IB with Myc and AKT antibodies.

To identify the region in Ack1 that recognize AKT, MEF1&2KO cells were transfected with Myc-tagged Ack1 deletions, as seen in FIG. 15, and HA-tagged AKT. The lysates were immunoprecipitated using Myc antibodies followed by immunoblotting with AKT antibodies. The Ack1 construct expressing SAM and kinase domains (cAck) was able to bind AKT, However, a construct lacking a part of the kinase domain (dAck) bound poorly to endogeneous AKT, seen in FIG. 21, top panel. GST-Ack1 that possess Kinase-SH3-CRIB domains but lacking SAM domain were able to bind AKT, seen in FIG. 7. Taken together it indicates that the kinase domain in Ack1 and tyrosine176 in the kinase domain along with AKT PH domain appear to be minimal domains required for efficient Ack1/AKT complex formation.

Somatic autoactivating mutation (E346K) in Ack1 activates AKT.

Figure 22:
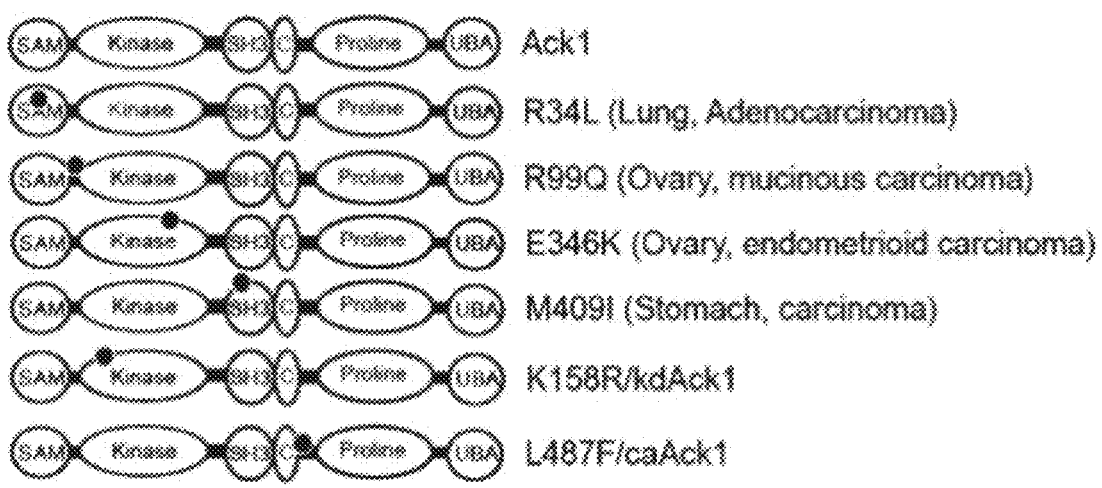
FIG. 22 is a schematic representation of Ack1 and various point mutants identified in the COSMIC database. Site-directed mutagenesis of Ack1 was performed to generate four HA-tagged point mutants. SAM, Sterile alpha motif; Kinase, kinase domain; SH3, Src homology domain 3; C, Cdc42 Rac interactive binding domain; Proline, Proline rich domain; UBA, Ubiquitin binding domain.
Figure 23:
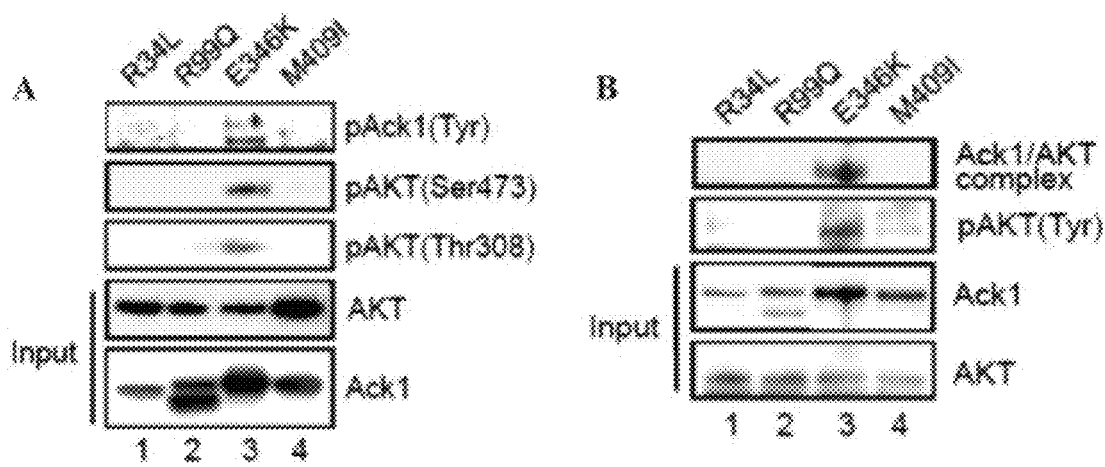
FIGS. 23(A) and (B) are blots showing the somatic autoactivation of Ack1. (A) E346K mutation results in Ack1 autoactivation leading to AKT activation. MEF1&2KO cells were transfected with Ack1 mutants and the lysates were IP using anti-HA antibodies followed by IB with pTyr antibodies (top panel). Lower panels show IB with indicated antibodies. (B)
Figure 25:
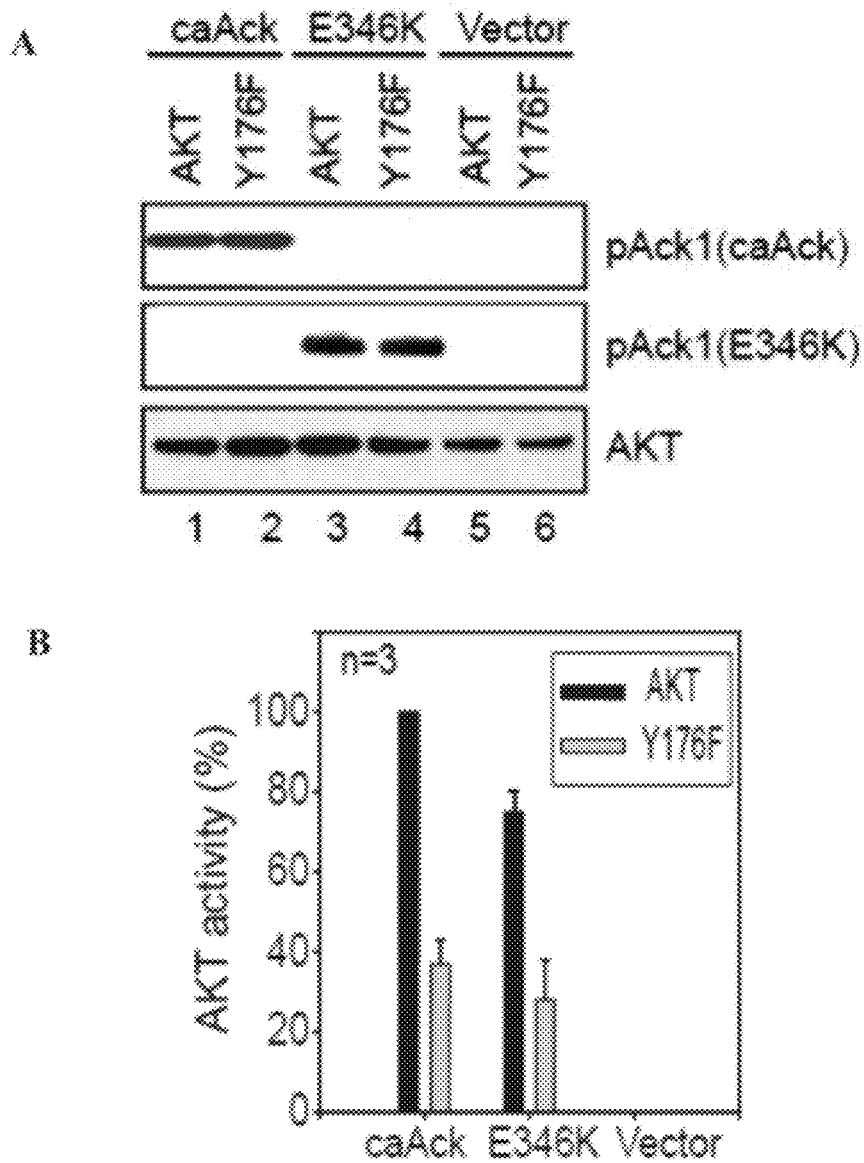

While growth factor binding to RTK or amplification of the Ack1 gene causes Ack1 kinase activation (Mahajan N P, et al. (2005) Activated tyrosine kinase Ack1 promotes prostate tumorigenesis: role of Ack1 in polyubiquitination of tumor suppressor Wwox. Cancer Res 65: 10514-10523; Mahajan N P, et al. (2007) Activated Cdc42-associated kinase Ack1 promotes prostate cancer progression via androgen receptor tyrosine phosphorylation. Proc Natl Acad Sci USA 104: 8438-8443; van der Horst E H, et al. (2005) Metastatic properties and genomic amplification of the tyrosine kinase gene ACK1. Proc Natl Acad Sci USA 102: 15901-15906), somatic autoactivating mutations in Ack1 have not yet been identified. Recently, four point mutations in Ack1, i.e. R34L, R99Q, E346K, M409I have been identified in the COSMIC database. Using site-directed mutagenesis, HA-tagged point mutants were generated, seen schematically in FIG. 22. These mutants were tested and it was observed that E346K mutant undergoes autoactivation and causes AKT Tyr/Ser/Thr-phosphorylation in serum starved cells, seen in FIGS. 23(A) and (B). Earlier studies have characterized a point mutant (L487F mutation) that leads to constitutive activation of Ack1, also called caAck (Mahajan N P, et al. (2007) Activated Cdc42-associated kinase Ack1 promotes prostate cancer progression via androgen receptor tyrosine phosphorylation. Proc Natl Acad Sci USA 104: 8438-8443; Kiyono M, et al. (2000) Stimulation of Ras guanine nucleotide exchange activity of Ras-GRF1/CDC25(Mm) upon tyrosine phosphorylation by the Cdc42-regulated kinase ACK1. J Biol Chem 275: 29788-29793). Both caAck(L487F mutant) and E346K autoactivating mutant of Ack1 exhibited Tyr284-phosphorylation in the activation loop, seen in FIG. 24. The intrinsic kinase activity of the Y176F mutant and the wildtype AKT were measured in the absence and presence of activated Ack1. The wildtype AKT displays significant increase in the kinase activity as compared to the Y176F mutant when coexpressed with either one of the Ack1 constructs, E346K and caAck, as seen in FIGS. 25 (A) and (B). These results demonstrate that the somatic autoactivating mutations in Ack1 are sufficient to activate AKT. Taken together with the earlier evidence indicating direct Ack1-AKT interaction, it shows a RTK/PI3K-independent AKT activation in tumors that is mediated by (auto) activated Ack1.

Mechanistically, targeting AKT to the plasma membrane is necessary for AKT activation (Manning B D, Cantley L C (2007) AKT/PKB signaling: navigating downstream. Cell 129: 1261-1274; Stephens L, et al. (1998) Protein kinase B kinases that mediate phosphatidylinositol 3,4,5-trisphosphate-dependent activation of protein kinase B. Science 279: 710-714; Stokoe D, et al. (1997) Dual role of phosphatidylinositol-3,4,5-trisphosphate in the activation of protein kinase B. Science 277: 567-570; Carpten J D, et al. (2007) A transforming mutation in the pleckstrin homology domain of AKT1 in cancer. Nature 448: 439-444). Loss of the PH domain resulted in decrease in AKT Tyr-phosphorylation upon co-expression with activated Ack1, seen in FIGS. 15, 19 and 20. Further, Ack1 interacts with RTKs which are located in the membrane (Mahajan N P, et al. (2005) Activated tyrosine kinase Ack1 promotes prostate tumorigenesis: role of Ack1 in polyubiquitination of tumor suppressor Wwox. Cancer Res 65: 10514-10523; Mahajan N P, et al. (2007) Activated Cdc42-associated kinase Ack1 promotes prostate cancer progression via androgen receptor tyrosine phosphorylation. Proc Natl Acad Sci USA 104: 8438-8443; Galisteo M L, et al. (2006) Activation of the nonreceptor protein tyrosine kinase Ack by multiple extracellular stimuli. Proc Natl Acad Sci USA 103: 9796-9801). These attributes suggest that activated Ack1 could engage AKT at the plasma membrane. To investigate the role of AKT Tyr176-phosphorylation on its cellular compartmentalization, phospho-antibodies were generated that specifically recognized Tyr176-phosphorylated AKT or pTyr176-AKT. The antibodies were extensively validated, as seen in FIGS. 26(A) and (B), also see top panels of FIGS. 27, 28 and 29; and FIG. 30. Normal prostate epithelial cells, RWPE, exhibited pTyr176-AKT expression upon treatment with EGF and heregulin ligand, seen in FIG. 26(A). The pTyr176-AKT was detected when activated Ack1 was coexpressed with AKT but not the Y176F mutant. Further, incubation of the pTyr176-AKT-antibody with phosphoAKT-Y176-peptide resulted in loss of binding to Tyr176-phosphorylated AKT, seen in FIG. 26(B). Cell fractionation studies revealed that heregulin, insulin and EGF treatment resulted in a time-dependent accumulation of pTyr176-AKT at the plasma membrane that lead to AKT activation, as seen in FIGS. 27, 28 and FIG. 30, top panels). Optimal AKT Tyr-176 phosphorylation and plasma membrane accumulation was observed at 10, 30 and 40 mins upon EGF, insulin and heregulin ligand treatments, respectively. See, FIGS. 30, 27, and 28. To assess whether EGF mediated AKT activation is dependent upon Tyr176-phosphorylation, MEF1&2KO cells expressing AKT or Y176F mutant were treated with EGF ligand. The Y176F mutant failed to translocate to the plasma membrane and become activated by EGF, seen in FIG. 31. The basal levels of pTyr176-AKT seen in cytosolic fraction, as seen in FIG. 31, panel 2, lanes 4-6) is likely to be Tyr-phosphorylated AKT3. Depletion of Ack1 by siRNA abrogated heregulin mediated AKT Tyr176-phosphorylation, plasma membrane localization and activation in MCF-7 cells, seen in FIG. 29, and MEFs (unpublished data). Further, GFP-E346K recruited dsRed-AKT but not the dsRed-Y176F mutant to the plasma membrane as assessed by immunofluorescence, seen in FIGS. 32(A) through (D) and 33(A) through (D). Taken together, these data suggest that Ack1 is a key intermediate signaling entity necessary for RTK mediated AKT Tyr176-phosphorylation.

Ack1 facilitates AKT plasma membrane localization and activation.

Because Ack1/AKT interaction was unaffected by LY294002 treatment, seen in FIG. 4(B), AKT Tyr176-phosphorylation was assessed to determine whether it could occur upon inhibition of PI3K activity. First, LY294002 treatment neither affected endogenous AKT Tyr176-phosphorylation nor its membrane localization, FIG. 34. Second, in contrast to Ack1 knockdown, depletion of PI3K 110α subunit by siRNA did not inhibit pTyr176-AKT levels in MCF7 cells treated with insulin, seen in FIG. 35. However, Ser473 phosphorylation of AKT was reduced upon knockdown of either Ack1 or PI3K, suggesting existence of two distinct pathways of AKT activation. Third, membrane fraction of AKT was phosphorylated at Ser473 even in the presence of LY294002 when coexpressed with activated Ack1 in serum starved MEF1&2KO cells, seen in FIG. 36, panel 2). To determine whether Tyr-phosphorylated AKT can translocate to the plasma membrane in the absence of PIP3, AKT point mutant R25C that binds PIP3 inefficiently (Franke T F, et al. (1995) The protein kinase encoded by the Akt proto-oncogene is a target of the PDGF-activated phosphatidylinositol 3-kinase. Cell 81: 727-736) was generated, seen in FIG. 37. The R25C mutant was Tyr-phosphorylated and recruited to membrane when coexpressed with activated Ack1, in the absence of ligand, as seen in FIGS. 38(A) and (B). Interestingly, in contrast to AKT which bound PIP3, Tyr-phosphorylated AKT bound another membrane phospholipid, phosphatidic acid (PA), seen in FIGS. 39(A) through (H). Combined together, the data indicates that RTK/Ack1 pathway could directly facilitate AKT plasma membrane localization and activation and a fraction of AKT that is Tyr176-phosphorylated can translocate to the membrane and undergo Ser473-phosphorylation even when PI3K is inhibited.

AKT Tyr176-phosphorylation suppresses expression of apoptotic genes and promotes mitotic progression.

Earlier studies observe that Ack1 translocates to the nucleus upon it's Tyr-phosphorylation (Mahajan N P, et al. (2007) Activated Cdc42-associated kinase Ack1 promotes prostate cancer progression via androgen receptor tyrosine phosphorylation. Proc Natl Acad Sci USA 104: 8438-8443). The localization of pTyr176-AKT was assessed during Ack1 activation. Ligand treatment facilitated nuclear translocation of both endogenous pTyr284-Ack1 and pTyr176-AKT, seen in FIG. 40. FoxO subgroup of transcription factors are phosphorylated by AKT leading to rapid relocalization of FoxO proteins from nucleus to cytoplasm, thus, preventing transactivation of target genes (Manning B D, Cantley L C (2007) AKT/PKB signaling: navigating downstream. Cell 129: 1261-1274; Greer E L, Brunet A (2005) FOXO transcription factors at the interface between longevity and tumor suppression. Oncogene 24: 7410-7425; Huang H, Tindall D J (2007) Dynamic FoxO transcription factors. J Cell Sci 120: 2479-2487). FoxO proteins regulate genes involved in cell cycle arrest (e.g. p21, p27KIP1), cell death (e.g. Bim-1) and DNA repair (e.g. GADD45) (Greer E L, Brunet A (2005) FOXO transcription factors at the interface between longevity and tumor suppression. Oncogene 24: 7410-7425). Real time quantitative RT-PCR analysis revealed that in MEF 1&2KO cells co-expressing caAck and AKT, expression of p21, p27, Rim-1 and GADD45 is down regulated as opposed to the activated Ack and Y176F mutant co-expressing cells, seen in FIG. 41(A). Consistent with this observation, depletion of Ack1 protein by siRNA resulted in increased FoxO-responsive gene expression, seen in FIG. 41(B).

To further understand the molecular role of Tyr176 in cell growth, a HA-tagged myristoylated Y176F or myr-Y176F, seen in FIG. 42, was generated. As the myristoylated version of AKT is constitutively anchored at the membrane, it exhibits high levels of AKT activation, as seen by Thr308-phosphorylation, as seen in FIG. 43. MEF1&2KO cells expressing myr-Y176F exhibited significant decrease in Thr308-phosphorylation confirming that AKT Tyr176-phosphorylation is an important event for subsequent AKT activation. Further, MEF1&2KO cells expressing myr-AKT grow exponentially as observed by an increase in the number of the double-positive HA and phospho-H3 (Ser10) stained cells, indicative of cells undergoing mitosis, seen in FIGS. 44(A) through (D). In contrast, the number of double-positive myr-Y176F expressing cells remained unchanged after 24 hours, seen in FIGS. 44(A) through (D). Thus, AKT Tyr176-phosphorylation can both suppress pro-apoptotic gene transcription and promote mitotic progression.

Probasin-Ack1 transgenic mice display AKT activation and develop prostatic intraepithelial neoplasia.

Figure 2:
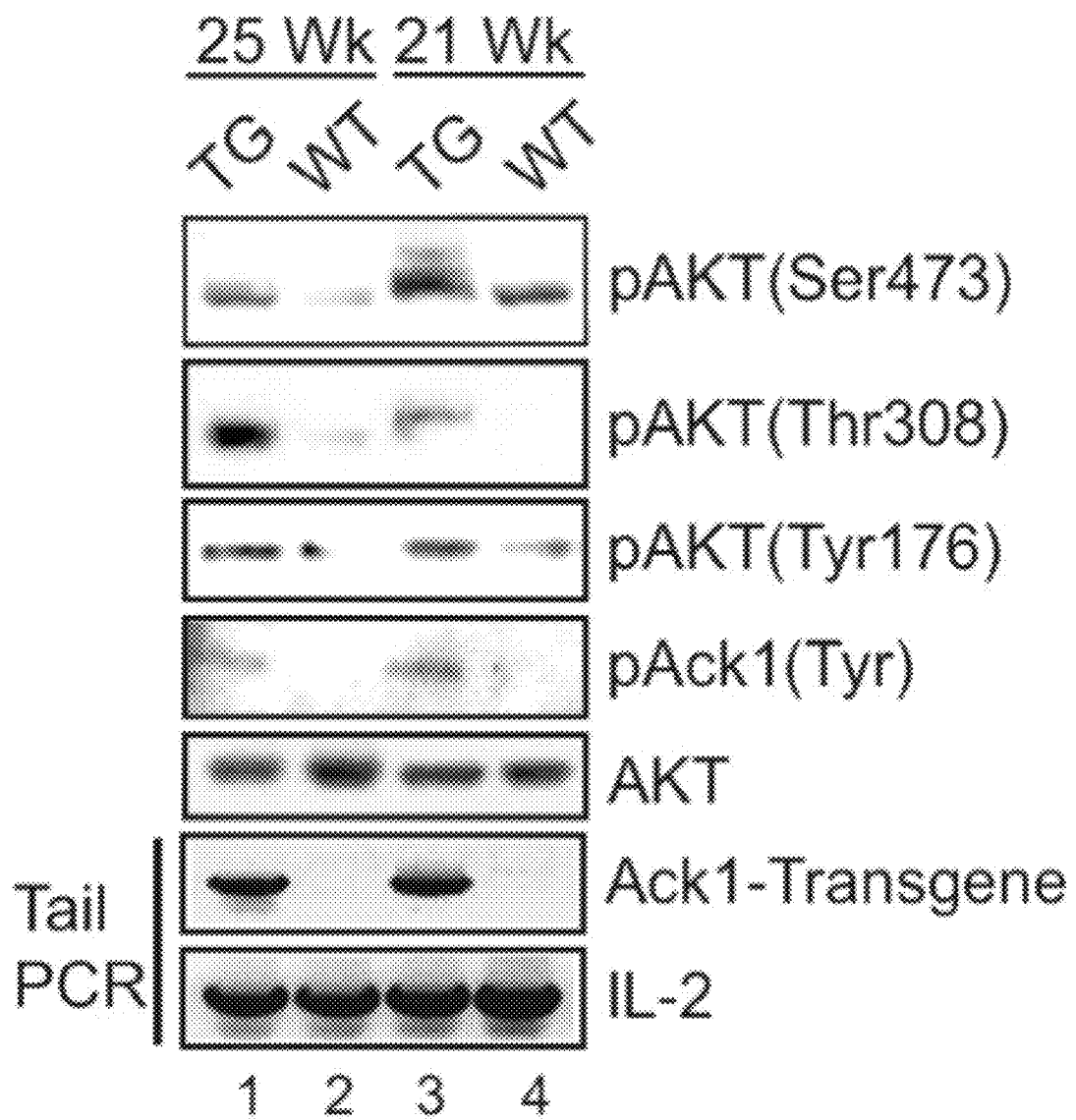
FIG. 2 is a blot of probasin-Ack1 transgenic mice displaying pTyr176-AKT and develop mPINs. Prostate lysates from 21 and 25 wk old TG and the WT siblings were IB with respective antibodies. The bottom 2 panels represent tail-PCR of these mice. IL-2 was an internal control for PCR.
Figure 46:
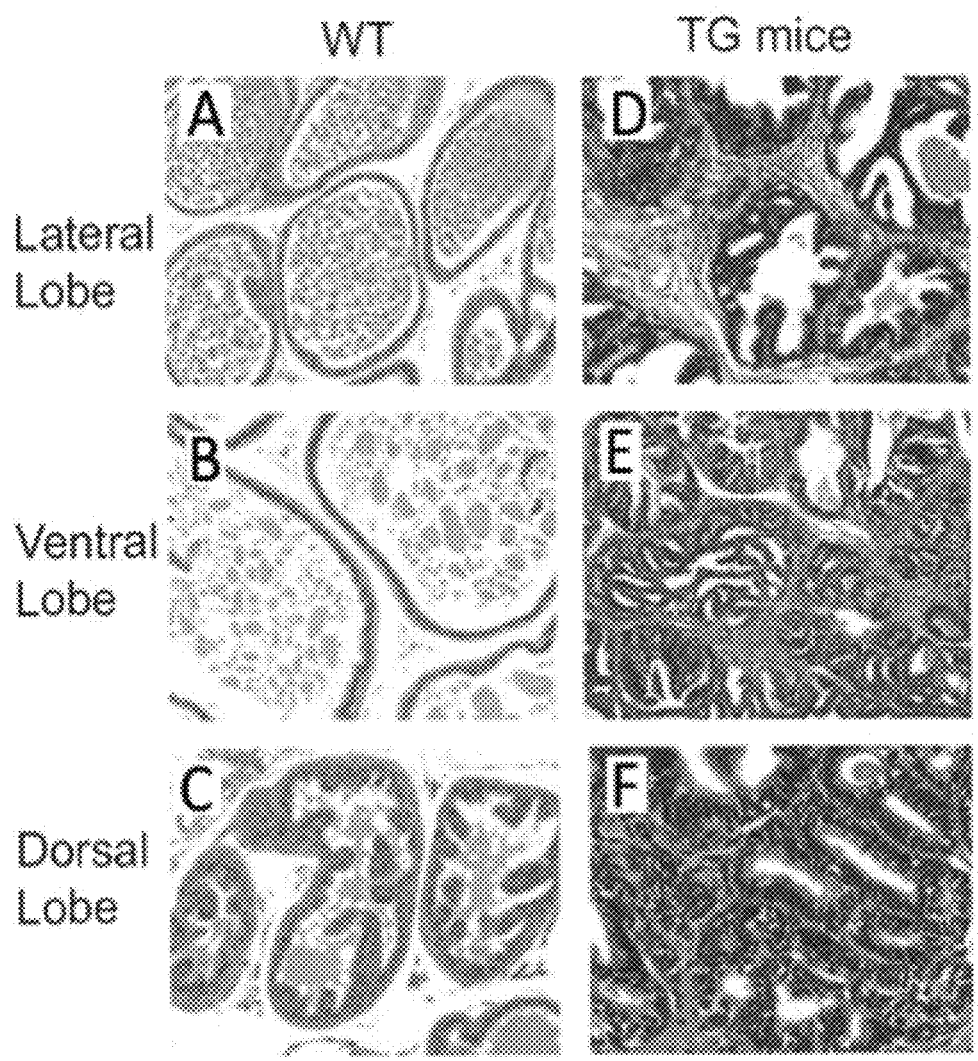

A transgenic mouse model was generated in which Myc-tagged activated Ack1 was expressed under the control of modified Probasin (PB) promoter, ARR2PB, seen in FIGS. 1(A) and (B). PB-Ack1 transgenic mice (TG) display significant increase in AKT Tyr176-phosphorylation leading to Ser473/Thr308-phosphorylation, as seen in FIG. 2, top 3 panels, and AKT substrate FOXO3a Ser318/321-phosphorylation, seen in FIG. 1(B), panel 2, in the prostates. These mice developed intraepithelial hyperplasia by 22 weeks, as seen in FIG. 45(B) as compared to FIG. 45(A), and mPINs by 44 weeks, seen in FIG. 45(C) compared to FIG. 45(A); FIGS. 46 (A) through (F). The prostate epithelium of TG mice was crowded with round to polygonal stratified nuclei, forming micropapillary projections and tufts, seen in FIG. 45(B). The acini were lined by a rim of basal cells, seen in FIG. 45(C). The areas of mPINs were easily identifiable and were characterized by prostatic acini containing intraluminal papillary structures lined by atypical cells with elongated nuclei exhibiting prominent nucleoli. Focally, the papillae merged into each other within the acini generating a cribiform pattern of growth, seen in FIGS. 46(D) through (F). Dorsal lobe exhibited an increased number of small acini lined by cells containing nuclei exhibiting prominent nucleoli and the neoplastic acini were devoid of myoepithelial cells, as seen in FIG. 46(F). Ack1 mediated AKT Tyr176-phosphorylation and activation appear to be more proximal stage initiating processes in neoplastic progression that mimic or serve as an alternative to those of PTEN loss which has been prominently emphasized in other mouse models of prostate cancer (Blanco-Aparicio C, et al. (2007) PTEN, more than the AKT pathway. Carcinogenesis 28: 1379-1386).

pTyr284-Ack1 and pTyr176-AKT expressions correlate with breast cancer progression.

To examine the role of pTyr284-Ack1 and pTyr176-AKT in breast tumor progression, an extensive tissue microarray analysis (TMA) of clinically annotated breast (n=476) tumor samples was performed. Tyr284 is the primary autophosphorylation site in Ack1 (Yokoyama N, Miller W T (2003) Biochemical properties of the Cdc42-associated tyrosine kinase ACK1. Substrate specificity, autophosphorylation, and interaction with Hck. J Biol Chem 278: 47713-47723), hence, phospho-Ack1 (Tyr284) antibodies were used to assess Ack1 activation. Immunohistochemical analysis revealed that pTyr284-Ack1 and pTyr176-AKT were expressed in both membrane and nucleus, seen in FIGS. 47(A) and (B). A significant increase in expression of pTyr284-Ack1 and pTyr176-AKT was seen when breast cancers from progressive stages were examined, i.e. normal to hyperplasia (ADH), ductal carcinoma in situ (DCIS), invasive ductal carcinoma (IDC) and lymph node metastatic (LNMM) stages, seen in FIGS. 48(A) through (H); FIGS. 49(A) and (B) and Table 2.

TABLE 2

The intensities of Tyr284-phosphorylated-Ack1 and Tyr176-phosphorylated-AKT for the trend analysis of breast cancer.

| Protein | Statistics | Normal | ADH | DCIS | IDC | LNMM |
|---|---|---|---|---|---|---|
| pAck1 Y284 | N | 52 | 31 | 38 | 126 | 39 |
| | Mean | 2 | .9 | 2.55 | 1.94 | 3.87 |
| | Median | 2 | 3 | 2 | 2 | 3 |
| | Std | 0.714 | 1.3 | 1.25 | 1.41 | 2 |
| | E | 0.1 | 0.23 | 0.20 | 0.13 | 0.32 |
| | CI Low | 1.8 | 2.43 | 2.14 | 1.7 | 3.22 |
| | CI Upper | 2. | 3. | 2. | 2. | 4. |
| pAKT Y176 | N | 45 | 39 | 38 | 11 | 37 |
| | Mean | 2. | 2. | 3. | 3. | 5. |
| | Medi | 2 | 3 | 4 | 4 | 6 |
| | Std | 0. | 0. | 1. | 2. | 1. |
| | SE | 0. | 0. | 0. | 0. | 0. |
| | CI | .1 | 2. | 3. | 3. | 4. |
| | CI | 2. | 3. | 4. | 4. | 5. |

Figure 50:
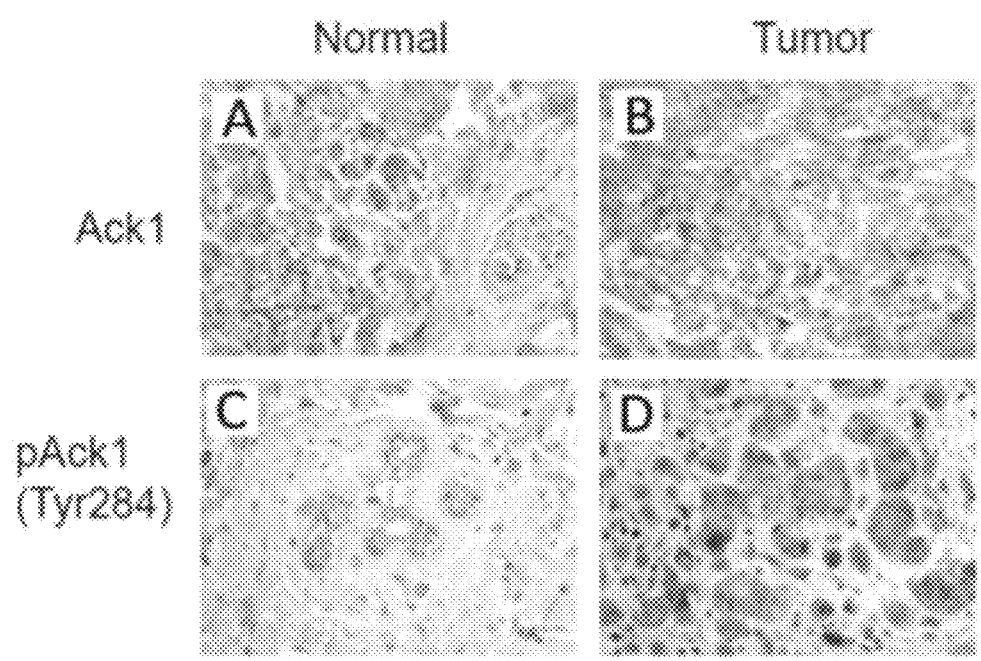

In contrast to pTyr284-Ack1, the total Ack1 levels remained unchanged between normal and tumor samples, compare FIGS. 50(A) and (B) with (C) and (D). ANOVA results indicated that both pTyr284-Ack1 and pTyr176-AKT expression differed significantly among progression stages ($p<0.0001$). When using Tukey-Kramer method to examine all pairwise differences between different stages, the expression levels of pTyr284-Ack1 and pTyr176-AKT in LNMM were significantly higher than those of all the earlier tumor stages; the expression levels were significantly lower in the normal samples when compared to those of all the later stages except for hyperplasia, seen in Tables 3 and 4.

TABLE 3

P-values of Tukey-Kramer multiple comparisons (simultaneous interference) of pTyr284-Ack1 intensity levels between all pairs of stages for breast cancer.

| pAc | Nor | ADH | DCI | IDC | LMM |
|---|---|---|---|---|---|
| Nor | | 0.03 | 0.33 | 0.99 | <0.00 |
| AD | | | 0.83 | 0.00 | 0.332 |
| DCI | | | | 0.12 | 0.000 |
| IDC | | | | | <0.00 |
| LM | | | | | |

* indicate significance at 0.05 level.

TABLE 4

P-values of Tukey-Kramer multiple comparisons (simultaneous interference) of pTyr176-AKT intensity levels between all pairs of stages for breast cancer.

| pAc | Nor | ADH | DCI | IDC | LMM |
|---|---|---|---|---|---|
| Nor | | 0.03 | 0.33 | 0.99 | <0.00 |
| AD | | | 0.83 | 0.00 | 0.332 |
| DCI | | | | 0.12 | 0.000 |
| IDC | | | | | <0.00 |
| LM | | | | | |

* indicate significance at 0.05 level.

Kaplan-Meir analyses revealed that patients with high expression of pTyr284-Ack1 and pTyr176-AKT are at a higher risk for cancer-related deaths, seen in FIGS. 51(A) and (B) and Table 5. Furthermore, expression of pTyr284-Ack1 was significantly correlated with pTyr176-AKT in situ (Spearman rank correlation coefficient $\rho=0.43$, $p<0.0001$), seen in FIG. 52.

TABLE 5

Kaplan-Meier survival estimates by Tyr284-phosphorylated Ack1 and Tyr176-phosphorylated AKT intensities for breast cancer TMA samples.

| | No. of subjects | Event | Censored |
|---|---|---|---|
| pAck1 ≤ 4 | 133 | 14% (19) | 86% (114) |
| pAck1 > 4 | 11 | 36% (4) | 64% (7) |
| pAKT ≤ 4 | 104 | 11% (11) | 89% (93) |
| pAKT > 4 | 36 | 25% (9) | 75% (27) |

Discussion

The data presented herein indicates that cells employ multiple and possibly mutually exclusive mechanisms to activate AKT. The reasons why RTKs would employ two distinct modes of AKT activation are not entirely clear. However, a fraction of AKT appears to utilize this alternative mode of activation in normal cells and prominently in cancerous cells. Even in the presence of PI3K inhibitor, ligand bound HER2/ErbB-2 or EGFR activated Ack1 which in turn Tyr-phosphorylated and activated AKT. AKT is frequently activated in pancreatic cancer which has been shown to be highly correlated to HER-2/neu overexpression (Schlieman M G, et al. (2003) Incidence, mechanism and prognostic value of activated AKT in pancreas cancer. Br J Cancer 89: 2110-2115). Moreover, many of the pancreatic cell lines and tumors expressing activated AKT had retained wild-type PTEN (Matsumoto J, et al. (2002) Differential mechanisms of constitutive Akt/PKB activation and its influence on gene expression in pancreatic cancer cells. Jpn J Cancer Res 93: 1317-1326; Sakurada A, et al. (1997) Infrequent genetic alterations of the PTEN/MMAC1 gene in Japanese patients with primary cancers of the breast, lung, pancreas, kidney, and ovary. Jpn J Cancer Res 88: 1025-1028). Pancreatic Intraepithelial Neoplasia (PanIN), pancreatic adenocarcinoma and breast tumors of MMTV-neu mice were observed exhibiting significantly higher levels of pTyr284-Ack1 and pTyr176-AKT (unpublished data). Taken collectively, the data explains AKT activation in those tumors that display amplification/activation of RTKs but have normal PI3K/PTEN levels. Based on the evidence, it is proposed that other tumors that possess somatic autoactivating mutations or amplification in non-receptor tyrosine kinases could use similar mechanisms for AKT activation.

The data shown in FIGS. 27 and 28, demonstrate that AKT in the plasma membrane is phosphorylated at Tyr 176 and mutation of this site in AKT abrogates appearance of AKT in the plasma membrane, seen in FIG. 31. Based on the evidence, the model suggests that as Ack1 signaling pathway is initiated at the plasma membrane by RTKs. Ack1 associates with growth factor-bound RTKs and is activated (Mahajan N P, et al. (2005) Activated tyrosine kinase Ack1 promotes prostate tumorigenesis: role of Ack1 in polyubiquitination of tumor suppressor Wwox. Cancer Res 65: 10514-10523; Mahajan N P, et al. (2007) Activated Cdc42-associated kinase Ack1 promotes prostate cancer progression via androgen receptor tyrosine phosphorylation. Proc Natl Acad Sci USA 104: 8438-8443). Ack1 is constitutively bound to AKT, seen in FIGS. 4(B) and 16); Activated Ack1 directly phosphorylates AKT at Tyr176, thus facilitating accumulation of Tyr176-phosphorylated AKT at the plasma membrane. Tyr176-phosphorylated AKT preferentially binds PA, a plasma membrane phospholipid as opposed to unphosphorylated AKT, see FIGS. 39(A) through (H) for details.

In contrast to AKT, pTyr176-AKT specifically binds the plasma membrane anionic phospholipid, PA, as seen in FIGS. 39(A) through (H). Tyr176-phosphorylation could induce conformational changes in the AKT PH domain to enable binding to PA. The PH domain of Son of sevenless (SOS) and PX domains of p47$^{Phox}$ have previously been shown to possess a phosphoinositide-binding pocket and a second anion binding pocket which enables them to interact with PA facilitating plasma membrane recruitment (Zhao C, et al. (2007) Phospholipase D2-generated phosphatidic acid couples EGFR stimulation to Ras activation by Sos. Nat. Cell Biol 9: 706-712; Karathanassis D, et al. (2002) Binding of the PX domain of p47(phox) to phosphatidylinositol 3,4-bisphosphate and phosphatidic acid is masked by an intramolecular interaction. Embo J 21: 5057-5068). Without being bound to any particular theory, it is likely that AKT also possesses a masked anion binding pocket, and Tyr176-phosphorylation induced conformational changes could unmask this pocket allowing it to bind PA.

In endogenous systems Ack1 associates with AKT2, seen in FIG. 4(B). The unpublised data from the inventors demonstrates significant tyrosine phosphorylation of AKT2 upon coexpression of Ack1 and AKT2 in HEK293T cells, suggesting that both AKT1 and 2 are Ack1 substrates.

This study demonstrates that Tyr176-phosphorylation is sufficient for AKT membrane localization followed by PDK1/PDK2 mediated activation, defining the upstream Ack1 kinase activity as 'PDK3'. However, it is possible other tyrosine kinases may target AKT for Tyr176-phosphorylation.

Multiple non-receptor tyrosine kinases were earlier shown to increase AKT activity (Chen R, Kim O, Yang J, Sato K, Eisenmann K M, et al. (2001) Regulation of Akt/PKB activation by tyrosine phosphorylation. J Biol Chem 276: 31858-31862; Conus N M, et al. (2002) Direct identification of tyrosine 474 as a regulatory phosphorylation site for the Akt protein kinase. J Biol Chem 277: 38021-38028), however, precise mechanism of AKT activation by any of the Tyr-modifications is not clear, nor is their role in initiation or progression of cancer. This report provides the first demonstration for a role of Tyr176-phosphorylated AKT in its compartmentalization, which allowed delineation of its critical role in AKT kinase activation, its potential to initiate neoplasia in mouse prostates and promote disease progression in human breast cancers.

Large numbers of tumors are reliant upon AKT activation for survival and growth making it an attractive target for molecular therapeutics (Cheng J Q, et al. (2005) The Akt/PKB pathway: molecular target for cancer drug discovery. Oncogene 24: 7482-7492). The assay that was used during development of AKT inhibitors was primarily based on AKT Ser473-phosphorylation. The data indicates that a new class of AKT inhibitors can be identified based on AKT Tyr176-phosphorylation. These novel inhibitors that block AKT membrane localization and activation could have major implications in cancer, diabetes and obesity research.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a biomarker for cancer, it will be apparent to those skilled in the art that variations and modifications are possible without deviating from the broad spirit and principle of the present invention. It is intended that all matters contained in the foregoing description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

What is claimed is:

1. A method of diagnosing cancer in a subject, comprising:
measuring the expression level, in a breast, prostate or pancreatic tissue or cell sample isolated from a subject, for at least one phosphorylated protein comprising a Tyrosine 176-phosphorylated AKT protein;
wherein an elevated expression level of the at least one phosphorylated protein, over a control expression level in a corresponding normal tissue or cell sample, is indicative of presence of a precancerous or cancerous lesion.

2. The method of claim 1, further comprising measuring the expression level of a Tyrosine 284-phosphorylated Ack1 protein.

3. The method of claim 1, wherein the tissue or cell sample comprises a breast tissue or cell, and wherein an elevated expression level of the at least one phosphorylated protein in the breast tissue or cell is indicative of presence of a precancerous or cancerous breast lesion.

4. The method of claim 3, wherein the elevated expression level indicates that the breast cancer is a tyrosine kinase-mediated, estrogen-independent, or heregulin-mediated cancer.

5. The method of claim 2, wherein the expression level comprises a ratio of the phosphorylated protein to the total level of the protein in the sample.

6. The method of claim 1, wherein the control expression level of the at least one phosphorylated protein in the corresponding normal tissue or cell sample is obtained from a database of protein levels from normal biological subjects.

7. The method of claim 6, wherein the database contains control levels obtained from a demographically diverse population.

8. The method of claim 1, wherein the expression level comprises an expression level in the cell membrane, cytoplasm or nucleus.

9. The method of claim 1, wherein the elevated expression level is further indicative of the stage of the cancer lesion.

10. The method of claim 1, wherein the elevated expression level is indicative of higher risk of death as compared to a subject not having an elevated expression level.

11. The method of claim 1, wherein the diagnosis is used to determine the anticancer treatment regimens for the subject.

12. The method of claim 1, wherein the protein expression level is measured with an antibody specific to the Tyrosine 176-phosphorylated AKT protein.

13. The method of claim 12, wherein the antibody comprises the amino acid sequence of SEQ ID No. 16 or an amino acid sequence having at least 90% sequence identity to SEQ ID No. 16.

14. The method of claim 1, further comprising treating the subject indicated to have presence of a precancerous or cancerous lesion.

* * * * *

SEQUENCE LISTING

<160> NUMBER OF SEQ ID NOS: 29

<210> SEQ ID NO 1
<211> LENGTH: 24
<212> TYPE: PRT
<213> ORGANISM: Homo sapiens

<400> SEQUENCE: 1

Val Lys Glu Lys Ala Thr Gly Arg Tyr Tyr Ala Met Lys Ile Leu Lys
1               5                   10                  15

Lys Glu Val Ile Val Ala Lys Asp
            20

<210> SEQ ID NO 2
<211> LENGTH: 24
<212> TYPE: PRT
<213> ORGANISM: Bos taurus

<400> SEQUENCE: 2

Val Lys Glu Lys Ala Thr Gly Arg Tyr Tyr Ala Met Lys Ile Leu Lys
1               5                   10                  15

-continued

Lys Glu Val Ile Val Ala Lys Asp
            20

<210> SEQ ID NO 3
<211> LENGTH: 24
<212> TYPE: PRT
<213> ORGANISM: Canus familiaris

<400> SEQUENCE: 3

Val Lys Glu Lys Ala Thr Gly Arg Tyr Tyr Ala Met Lys Ile Leu Lys
1               5                   10                  15

Lys Glu Val Ile Val Ala Lys Asp
            20

<210> SEQ ID NO 4
<211> LENGTH: 24
<212> TYPE: PRT
<213> ORGANISM: Mus musculus

<400> SEQUENCE: 4

Val Lys Glu Lys Ala Thr Gly Arg Tyr Tyr Ala Met Lys Ile Leu Lys
1               5                   10                  15

Lys Glu Val Ile Val Ala Lys Asp
            20

<210> SEQ ID NO 5
<211> LENGTH: 24
<212> TYPE: PRT
<213> ORGANISM: Rattus norvegicus

<400> SEQUENCE: 5

Val Lys Glu Lys Ala Thr Gly Arg Tyr Tyr Ala Met Lys Ile Leu Lys
1               5                   10                  15

Lys Glu Val Ile Val Ala Lys Asp
            20

<210> SEQ ID NO 6
<211> LENGTH: 24
<212> TYPE: PRT
<213> ORGANISM: Xenopus laevis

<400> SEQUENCE: 6

Val Lys Glu Lys Ala Thr Gly Arg Tyr Tyr Ala Met Lys Ile Leu Lys
1               5                   10                  15

Lys Glu Val Ile Val Ala Lys Asp
            20

<210> SEQ ID NO 7
<211> LENGTH: 24
<212> TYPE: PRT
<213> ORGANISM: Danio rerio

<400> SEQUENCE: 7

Val Lys Glu Lys Ala Thr Gly Lys Tyr Tyr Ala Met Lys Ile Leu Lys
1               5                   10                  15

Lys Glu Val Ile Val Ala Lys Asp
            20

<210> SEQ ID NO 8
<211> LENGTH: 24
<212> TYPE: PRT
<213> ORGANISM: Aedes aegypti

<400> SEQUENCE: 8

-continued

Cys Arg Glu Lys Thr Thr Ala Lys Leu Tyr Ala Ile Lys Ile Leu Lys
1               5                   10                  15

Lys Glu Val Ile Val Gln Lys Asp
            20

<210> SEQ ID NO 9
<211> LENGTH: 24
<212> TYPE: PRT
<213> ORGANISM: Drosophila melanogaster

<400> SEQUENCE: 9

Cys Arg Glu Lys Ala Thr Ala Lys Leu Tyr Ala Ile Lys Ile Leu Lys
1               5                   10                  15

Lys Glu Val Ile Ile Gln Lys Asp
            20

<210> SEQ ID NO 10
<211> LENGTH: 24
<212> TYPE: PRT
<213> ORGANISM: Bombyx mori

<400> SEQUENCE: 10

Ser Arg Glu Lys Gly Thr Gly Lys Leu Tyr Ala Met Lys Ile Leu Lys
1               5                   10                  15

Lys His Leu Ile Ile Gln Lys Asp
            20

<210> SEQ ID NO 11
<211> LENGTH: 24
<212> TYPE: PRT
<213> ORGANISM: Caenorhabditis elegans

<400> SEQUENCE: 11

Cys Lys Glu Lys Arg Thr Gln Lys Leu Tyr Ala Ile Lys Ile Leu Lys
1               5                   10                  15

Lys Asp Val Ile Ile Ala Arg Glu
            20

<210> SEQ ID NO 12
<211> LENGTH: 24
<212> TYPE: PRT
<213> ORGANISM: Saccharomyces cerevisiae

<400> SEQUENCE: 12

Val Lys Lys Lys Asp Thr Gln Arg Ile Tyr Ala Met Lys Val Leu Ser
1               5                   10                  15

Lys Lys Val Ile Val Lys Lys Asn
            20

<210> SEQ ID NO 13
<211> LENGTH: 24
<212> TYPE: PRT
<213> ORGANISM: Homo sapiens

<400> SEQUENCE: 13

Val Lys Glu Lys Ala Thr Gly Arg Tyr Tyr Ala Met Lys Ile Leu Lys
1               5                   10                  15

Lys Glu Val Ile Val Ala Lys Asp
            20

<210> SEQ ID NO 14
<211> LENGTH: 24

```
<212> TYPE: PRT
<213> ORGANISM: Homo sapiens

<400> SEQUENCE: 14

Val Arg Glu Lys Ala Thr Gly Arg Tyr Tyr Ala Met Lys Ile Leu Arg
1               5                   10                  15

Lys Glu Val Ile Ile Ala Lys Asp
            20

<210> SEQ ID NO 15
<211> LENGTH: 24
<212> TYPE: PRT
<213> ORGANISM: Homo sapiens

<400> SEQUENCE: 15

Val Arg Glu Lys Ala Ser Gly Lys Tyr Tyr Ala Met Lys Ile Leu Lys
1               5                   10                  15

Lys Glu Val Ile Ile Ala Lys Asp
            20

<210> SEQ ID NO 16
<211> LENGTH: 11
<212> TYPE: PRT
<213> ORGANISM: Artificial
<220> FEATURE:
<223> OTHER INFORMATION: Immunogenic phosphopeptide detector for AKT

<400> SEQUENCE: 16

Ala Thr Gly Arg Tyr Tyr Ala Met Lys Ile Leu
1               5                   10

<210> SEQ ID NO 17
<211> LENGTH: 11
<212> TYPE: PRT
<213> ORGANISM: Artificial
<220> FEATURE:
<223> OTHER INFORMATION: Immunogenic non-phosphopeptide detector for AKT

<400> SEQUENCE: 17

Ala Thr Gly Arg Tyr Tyr Ala Met Lys Ile Leu
1               5                   10

<210> SEQ ID NO 18
<211> LENGTH: 22
<212> TYPE: DNA
<213> ORGANISM: Artificial
<220> FEATURE:
<223> OTHER INFORMATION: Forward DNA primer for p27/Kip1

<400> SEQUENCE: 18
tcaaacgtga gagtgtctaa cg                                          22

<210> SEQ ID NO 19
<211> LENGTH: 20
<212> TYPE: DNA
<213> ORGANISM: Artificial
<220> FEATURE:
<223> OTHER INFORMATION: Reverse DNA primer for p27/Kip1

<400> SEQUENCE: 19
ccgggccgaa gagatttctg                                             20

<210> SEQ ID NO 20
<211> LENGTH: 18
<212> TYPE: DNA
<213> ORGANISM: Artificial
```

```
<220> FEATURE:
<223> OTHER INFORMATION: Forward DNA primer for p27

<400> SEQUENCE: 20
tgttccgcac aggagcaa                                                  18

<210> SEQ ID NO 21
<211> LENGTH: 17
<212> TYPE: DNA
<213> ORGANISM: Artificial
<220> FEATURE:
<223> OTHER INFORMATION: Reverse DNA primer for p27

<400> SEQUENCE: 21
tgagcgcatc gcaatca                                                   17

<210> SEQ ID NO 22
<211> LENGTH: 20
<212> TYPE: DNA
<213> ORGANISM: Artificial
<220> FEATURE:
<223> OTHER INFORMATION: Forward DNA primer for Bim

<400> SEQUENCE: 22
cccggagata cggattgcac                                                20

<210> SEQ ID NO 23
<211> LENGTH: 20
<212> TYPE: DNA
<213> ORGANISM: Artificial
<220> FEATURE:
<223> OTHER INFORMATION: Reverse DNA primer for Bim

<400> SEQUENCE: 23
gcctcgcggt aatcatttgc                                                20

<210> SEQ ID NO 24
<211> LENGTH: 20
<212> TYPE: DNA
<213> ORGANISM: Artificial
<220> FEATURE:
<223> OTHER INFORMATION: Forward DNA primer for Gadd 45

<400> SEQUENCE: 24
agaccgaaag gatggacacg                                                20

<210> SEQ ID NO 25
<211> LENGTH: 19
<212> TYPE: DNA
<213> ORGANISM: Artificial
<220> FEATURE:
<223> OTHER INFORMATION: Reverse DNA primer for Gadd 45

<400> SEQUENCE: 25
tgactccgag ccttgctga                                                 19

<210> SEQ ID NO 26
<211> LENGTH: 20
<212> TYPE: DNA
<213> ORGANISM: Artificial
<220> FEATURE:
<223> OTHER INFORMATION: Forward DNA primer for Hprt1

<400> SEQUENCE: 26
cacaggacta gaacacctgc                                                20
```

```
<210> SEQ ID NO 27
<211> LENGTH: 19
<212> TYPE: DNA
<213> ORGANISM: Artificial
<220> FEATURE:
<223> OTHER INFORMATION: Reverse DNA primer for Hprt

<400> SEQUENCE: 27
gctggtgaaa aggacctct                                                  19

<210> SEQ ID NO 28
<211> LENGTH: 18
<212> TYPE: DNA
<213> ORGANISM: Artificial
<220> FEATURE:
<223> OTHER INFORMATION: Forward DNA primer for ACTB

<400> SEQUENCE: 28
gtgggcatgg gtcagaag                                                   18

<210> SEQ ID NO 29
<211> LENGTH: 18
<212> TYPE: DNA
<213> ORGANISM: Artificial
<220> FEATURE:
<223> OTHER INFORMATION: Reverse DNA primer for ACTB

<400> SEQUENCE: 29
tccatcacga tgccagtg                                                   18
```